US008207193B2

(12) United States Patent
Ford et al.

(10) Patent No.: US 8,207,193 B2
(45) Date of Patent: Jun. 26, 2012

(54) QUINICLIDINE DERIVATIVES OF (HETERO) ARYLCYCLOHEPTANECARBOXYLIC ACID AS MUSCARINIC RECEPTOR ANTAGONISTS

(75) Inventors: Rhonan Ford, Loughborough (GB); Andrew Mather, Loughborough (GB); Antonio Mete, Loughborough (GB)

(73) Assignee: Astrazeneca AB, Sodertalje (SE)

( * ) Notice: Subject to any disclaimer, the term of this patent is extended or adjusted under 35 U.S.C. 154(b) by 414 days.

(21) Appl. No.: 12/514,509

(22) PCT Filed: Nov. 13, 2007

(86) PCT No.: PCT/GB2007/004350
§ 371 (c)(1),
(2), (4) Date: May 12, 2009

(87) PCT Pub. No.: WO2008/059245
PCT Pub. Date: May 22, 2008

(65) Prior Publication Data
US 2010/0029713 A1 Feb. 4, 2010

Related U.S. Application Data

(60) Provisional application No. 60/865,667, filed on Nov. 14, 2006, provisional application No. 60/869,384, filed on Dec. 11, 2006.

(51) Int. Cl.
A61K 31/439 (2006.01)
C07D 453/02 (2006.01)
A61P 11/00 (2006.01)

(52) U.S. Cl. ........................................ 514/305; 546/133
(58) Field of Classification Search .................. 514/305; 546/133
See application file for complete search history.

(56) References Cited

U.S. PATENT DOCUMENTS

| 2,404,588 A | 7/1946 | Martin et al. |
| 4,579,854 A | 4/1986 | Iwakuma et al. |
| 5,482,934 A | 1/1996 | Calatayud et al. |
| 2002/0169208 A1 | 11/2002 | Druzgala et al. |
| 2002/0173536 A1 | 11/2002 | Noe et al. |
| 2005/0222144 A1 | 10/2005 | Konetzki et al. |
| 2010/0029713 A1 | 2/2010 | Ford et al. |
| 2011/0172237 A1* | 7/2011 | Bull et al. ................. 514/252.04 |
| 2011/0190309 A1* | 8/2011 | Ford et al. ................. 514/252.04 |

FOREIGN PATENT DOCUMENTS

| DE | 2104179 C3 | 10/1980 |
| DE | 4129535 A1 | 3/1992 |
| DE | 10216333 A1 | 10/2003 |
| EP | 1785421 A1 | 5/2007 |
| EP | 1894568 A1 | 3/2008 |
| FR | 2155927 | 10/1971 |
| FR | 2123519 | 1/1972 |
| FR | 2168881 | 1/1972 |
| FR | 2208649 | 12/1972 |
| GB | 1320069 | 6/1973 |
| WO | WO-92/05147 A1 | 4/1992 |
| WO | 98/04517 A1 | 2/1998 |
| WO | 98/21183 A1 | 5/1998 |
| WO | 01/04118 A2 | 1/2001 |
| WO | WO-02/00679 A2 | 1/2002 |
| WO | 02/053564 A2 | 7/2002 |

(Continued)

OTHER PUBLICATIONS

Casarosa et al., The Journal of pharmacology and experimental therapeutics, Apr. 2010) vol. 333, No. 1, pp. 201-209.* Navratil et al., Journal of Radioanalytical and Nuclear Chemistry (2004), 262(2), 429-432.*
Cazzola, M., et al., "Ultra long-acting $\beta_2$-agonists in development for asthma and chronic obstructive pulmonary disease," *Expert Opin. Investig. Drugs* (2005), vol. 14, No. 7, pp. 775-783.
Lee, A.M., et al., "Selective muscarinic receptor antagonists for airway diseases," *Current Opinion in Pharmacology* (2001), vol. 1, pp. 223-229.
Database Beilstein [Online] 1-17 Beilstein Institute for Organic Chemistry, Frankfurt-Main, DE; XP002469597 Database accession No . BRN :1558578& Boll . Chim . Farm . 103,1964,576-582 abstract.
Medicinal Chemistry Research (1992), 2(6) 384-93.
R .R . Mikhlina et al : "Synthesis and 1-17 cholinolytic properties of esters of 3-hydroxyquiniclidiner" Pharmaceutical Chemistry Journal, vol. 15, No. 8, 1981, pp. 5169-572, XP002469746 NeKluwer Academic Publishers-Consultants Bureau abstract ; example IX.
Hackam et al. 'Translation of Research Evidence from Animals to Humans' Journal of the American Medical Association (2006); vol. 296; No. 14; pp. 1731-1732.
Jordan et al. 'Tamoxifen: A Most Unlikely Pioneering Medicine' Nature Reviews: Drug Discovery (2003); vol. 2; pp. 205-213.

*Primary Examiner* — Niloofar Rahmani
(74) *Attorney, Agent, or Firm* — Astrazeneca AB

(57) ABSTRACT

The invention provides compounds of formula (I) wherein $R^4$ is a group of formula (II) or (IIIa) or (IIIb) and $R^1$, $R^2$, $R^3$, $R^5$, a, b and X are as defined in the specification, a process for their preparation, pharmaceutical compositions containing them, a process for preparing pharmaceutical compositions, their use in therapy and intermediates of use in their preparation (I), (II), (IIIa), (IIIb).

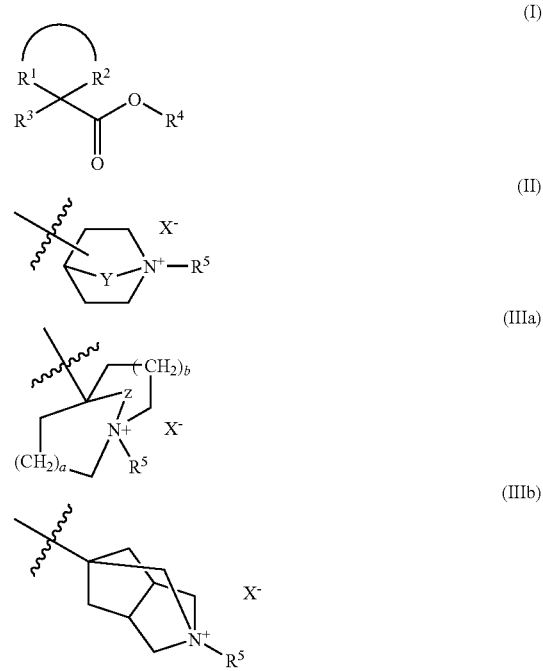

15 Claims, No Drawings

FOREIGN PATENT DOCUMENTS

| | | | |
|---|---|---|---|
| WO | WO-02/076933 | A1 | 10/2002 |
| WO | WO-02/088167 | A1 | 11/2002 |
| WO | 02/096855 | A2 | 12/2002 |
| WO | WO-03/042164 | A1 | 5/2003 |
| WO | 03/087094 | A2 | 10/2003 |
| WO | WO-2004/032921 | A1 | 4/2004 |
| WO | 2004/096800 | A2 | 11/2004 |
| WO | 2005/000815 | A2 | 1/2005 |
| WO | WO-2005/025555 | A2 | 3/2005 |
| WO | WO-2005/041980 | A1 | 5/2005 |
| WO | 2006/035303 | A1 | 4/2006 |
| WO | 2006/048225 | A1 | 5/2006 |
| WO | WO-2006/046916 | A1 | 5/2006 |
| WO | 2006/066928 | A1 | 6/2006 |
| WO | 2006/112778 | A1 | 10/2006 |
| WO | 2007/015664 | A1 | 2/2007 |
| WO | 2007/015667 | A1 | 2/2007 |
| WO | 2007/017669 | A1 | 2/2007 |
| WO | 2007/017670 | A1 | 2/2007 |
| WO | 2007/018461 | A1 | 2/2007 |
| WO | 2007/027134 | A1 | 3/2007 |
| WO | 2007/068929 | A1 | 6/2007 |
| WO | 2007/123465 | A1 | 11/2007 |
| WO | 2008/010765 | A1 | 1/2008 |
| WO | 2008/017824 | A1 | 2/2008 |
| WO | 2008/017827 | A2 | 2/2008 |
| WO | 2008/023157 | A1 | 2/2008 |
| WO | 2008/059239 | A1 | 5/2008 |
| WO | WO-2008/059245 | A1 | 5/2008 |
| WO | 2008/075005 | A1 | 6/2008 |
| WO | 2008/075006 | A1 | 6/2008 |
| WO | 2008/075026 | A1 | 6/2008 |
| WO | 2008/096093 | A1 | 8/2008 |
| WO | 2008/096094 | A1 | 8/2008 |
| WO | 2008/096111 | A1 | 8/2008 |
| WO | 2008/096121 | A1 | 8/2008 |
| WO | 2008/096126 | A1 | 8/2008 |
| WO | 2008/096127 | A2 | 8/2008 |
| WO | 2008/096128 | A1 | 8/2008 |
| WO | 2008/096129 | A1 | 8/2008 |
| WO | 2008/096136 | A1 | 8/2008 |
| WO | 2008/096143 | A1 | 8/2008 |
| WO | 2008/096149 | A2 | 8/2008 |
| WO | 2008/099186 | A1 | 8/2008 |
| WO | 2008/104790 | A1 | 9/2008 |
| WO | 2008/149053 | A1 | 12/2008 |
| WO | 2008/149110 | A1 | 12/2008 |
| WO | 2009/098448 | A1 | 8/2009 |
| WO | 2009/098453 | A1 | 8/2009 |
| WO | 2009/098455 | A1 | 8/2009 |
| WO | 2009/138707 | A1 | 11/2009 |
| WO | 2009/139707 | A1 | 11/2009 |
| WO | 2009/139708 | A1 | 11/2009 |
| WO | 2009/139709 | A1 | 11/2009 |
| WO | 2009/139710 | A1 | 11/2009 |
| WO | WO-2009/138707 | A1 | 11/2009 |
| WO | WO-2009/139708 | A1 | 11/2009 |
| WO | 2009/153536 | A1 | 12/2009 |
| WO | 2009/154554 | A1 | 12/2009 |
| WO | 2009/154555 | A1 | 12/2009 |
| WO | 2010/015792 | A1 | 2/2010 |
| WO | 2010/018352 | A1 | 2/2010 |
| WO | 2010/019097 | A1 | 2/2010 |
| WO | 2010/019098 | A1 | 2/2010 |
| WO | 2010/019099 | A1 | 2/2010 |

* cited by examiner

QUINICLIDINE DERIVATIVES OF (HETERO) ARYLCYCLOHEPTANECARBOXYLIC ACID AS MUSCARINIC RECEPTOR ANTAGONISTS

This patent is a US National Stage under 35 U.S.C. §371 of International Application No. PCT/GB2007/004350 (filed 13 Nov. 2007; published as WO2008/059245 (22 May 2008), which, in turn, claims priority under 35 U.S.C. §119(e) to U.S. Provisional Patent Application Nos. 60/865,667 (filed 14 Nov. 2006) and 60/869,384 (filed 11 Dec. 2006). The entire text of each of the above-referenced patent applications is incorporated by reference into this patent.

The present invention relates to cycloalkyl-substituted alkyl esters of polycyclic amino alcohols, a process for their preparation, pharmaceutical compositions containing them, a process for preparing pharmaceutical compositions, their use in therapy and intermediates of use in their preparation.

Muscarinic receptors are a G-protein coupled receptor (GPCR) family having five family members $M_1$, $M_2$, $M_3$, $M_4$ and $M_5$. Of the five muscarinic subtypes, three ($M_1$, $M_2$ and $M_3$) are known to exert physiological effects on human lung tissue.

Parasympathetic nerves are the main pathway for reflex bronchoconstriction in human airways and mediate airway tone by releasing acetylcholine onto muscarinic receptors. Airway tone is increased in patients with respiratory disorders such as asthma and chronic obstructive pulmonary disease (COPD), and for this reason muscarinic receptor antagonists have been developed for use in treating airway diseases. Muscarinic receptor antagonists, often called anticholinergics in clinical practice, have gained widespread acceptance as a first-line therapy for individuals with COPD, and their use has been extensively reviewed in the literature (e.g. Lee et al, Current Opinion in Pharmacology 2001, 1, 223-229).

When used to treat respiratory disorders, muscarinic receptor antagonists are typically administered by inhalation. However, when administered by inhalation a significant proportion of the muscarinic receptor antagonist is often absorbed into the systemic circulation resulting in reported side effects such as dry mouth. Additionally, the majority of muscarinic antagonists have a relatively short duration of action requiring that they be administered several times a day. Such a multiple-daily dosing regime is not only inconvenient to the patient but also creates a significant risk of inadequate treatment due to patient non-compliance associated with the frequent repeat dosing schedule.

There therefore remains a need for novel compounds that are capable of blocking muscarinic receptors. In particular, a need exists for new muscarinic antagonists that have high potency and reduced systemic side effects when administered by inhalation. Moreover, a need exists for new muscarinic antagonists that exhibit a long duration of action when dosed by inhalation, and which are amenable to either once or twice daily dosing.

WO 98/04517 describes arylcyclopropane, arylcyclobutane, arylcyclopentane and arylcyclohexane carboxylic esters having antimuscarinic activity on the urinary bladder smooth muscle.

In accordance with the present invention there is provided a compound of formula (I):

wherein $R^1$ and $R^2$ together with the carbon atom to which they are both directly attached form a 7 membered aliphatic carbocyclic ring which may be optionally substituted by one or more substituents independently selected from halogen, hydroxyl, $C_{1-6}$ alkoxy, $NH_2$, $NH(C_{1-6}$ alkyl), $N(C_{1-6}$ alkyl$)_2$ and $C_{1-6}$ alkyl which $C_{1-6}$ alkyl may be optionally substituted by one or more substituents independently selected from halogen and hydroxyl;

$R^3$ represents phenyl or a 5 to 6 membered heteroaryl ring, each of which may be optionally substituted by one or more substituents independently selected from halogen, cyano, nitro, SH, $S(O)_{0-2}R^9$, $NR^{10}R^{11}$, $S(O)_2NR^{12}R^{13}$, $C(O)NR^{14}R^{15}$, $C(O)_2R^{16}$, $NR^{17}S(O)_2R^{18}$, $NR^{19}C(O)R^{20}$, $NR^{21}C(O)_2R^{22}$, $NR^{23}C(O)NR^{24}R^{25}$, $OR^{26}$ and $C_{1-6}$ alkyl which $C_{1-6}$ alkyl may be optionally substituted by one or more substituents independently selected from halogen, hydroxyl, $C_{1-6}$ alkoxy, $NH_2$, $NH(C_{1-6}$ alkyl) and $N(C_{1-6}$ alkyl$)_2$;

$R^4$ represents a group of formula (II) or (IIIa) or (IIIb);

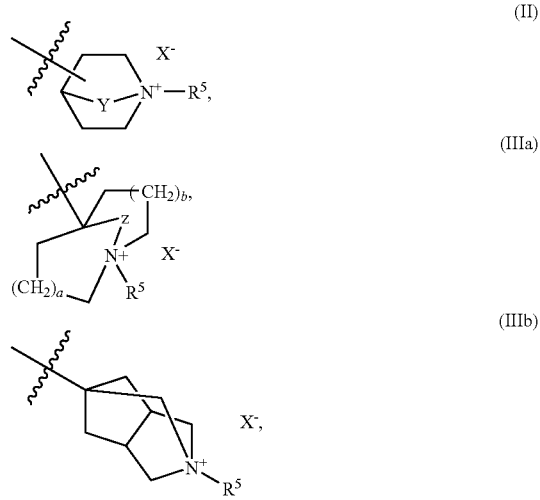

wherein

Y is $-CH_2-$, $-CH_2CH_2-$ or $-CH_2CH_2CH_2-$ and the substitution on the ring in group (II) may be in the 3 or 4 positions;

a is 1 or 2;

b is 1 or 2;

Z is $-CH_2-$;

$R^5$ represents a group of formula (IV)

wherein
w is 0 or 1;
$R^6$ represents $C_{1-4}$ alkylene optionally substituted by one or more substituents independently selected from halogen, hydroxyl, $C_{1-6}$ alkoxy, $NH_2$, $NH(C_{1-6}$ alkyl) and $N(C_{1-6}$ alkyl)$_2$;
when w is 0, y is 0; when w is 1, y is 0 or 1;
Q represents O, $S(O)_{0-2}$, $NR^8$, —$CONR^8$—, —$SO_2NR^8$—, —$NR^8CO$—, —$NR^8SO_2$—, —OC(O)—, —C(O)O—, —HC=CH— or ethynylene;
$R^7$ represents a cyclic group $Cyc^1$ or a $C_{1-4}$ alkyl group which $C_{1-4}$ alkyl group may be optionally substituted by one or more substituents independently selected from halogen, hydroxyl, $C_{1-4}$ alkoxy, $NH_2$, $NH(C_{1-4}$ alkyl), $N(C_{1-4}$ alkyl)$_2$, a cyclic group $Cyc^2$ and —O$Cyc^2$; and $R^7$ may additionally represent hydrogen when Q represents O, $NR^8$, —$CONR^8$—, —$SO_2NR^8$—, —C(O)O—, —HC=CH— or ethynylene;
$Cyc^1$ and $Cyc^2$ each independently represent aryl, heteroaryl, a 3 to 8 membered aliphatic carbocyclic ring or a 4 to 8 membered aliphatic heterocyclic ring, each of which may be optionally substituted by one or more substituents independently selected from halogen, cyano, nitro, SH, $S(O)_{0-2}R^9$, $NR^{10}R^{11}$, $S(O)_2NR^{12}R^{13}$, $C(O)NR^{14}R^{15}$, $C(O)_2R^{16}$, $NR^{17}S(O)_2R^{18}$, $NR^{19}C(O)R^{20}$, $NR^{21}C(O)_2R^{22}$, $NR^{23}C(O)NR^{24}R^{25}$, $OR^{26}$, phenyl and $C_{1-6}$ alkyl which phenyl or $C_{1-6}$ alkyl may be optionally substituted by one or more substituents independently selected from halogen, hydroxyl, $C_{1-6}$ alkoxy, $NH_2$, $NH(C_{1-6}$ alkyl) and $N(C_{1-6}$ alkyl)$_2$;
$R^8$ represents hydrogen or $C_{1-6}$ alkyl;
$R^9$ and $R^{18}$ each independently represent $C_{1-6}$ alkyl, which $C_{1-6}$ alkyl may be optionally substituted by one or more substituents independently selected from halogen, hydroxyl, $C_{1-6}$ alkoxy, $NH_2$, $NH(C_{1-6}$ alkyl) and $N(C_{1-6}$ alkyl)$_2$; and $R^{10}$, $R^{11}$, $R^{12}$, $R^{13}$, $R^{14}$, $R^{15}$, $R^{16}$, $R^{17}$, $R^{19}$, $R^{20}$, $R^{21}$, $R^{22}$, $R^{23}$, $R^{24}$, $R^{25}$ and $R^{26}$ each independently represent hydrogen or $C_{1-6}$ alkyl, which $C_{1-6}$ alkyl may be optionally substituted by one or more substituents independently selected from halogen, hydroxyl, $C_{1-6}$ alkoxy, $NH_2$, $NH(C_{1-6}$ alkyl) and $N(C_{1-6}$ alkyl)$_2$; or any of $R^{10}$ and $R^{11}$, $R^{12}$ and $R^{13}$, $R^{14}$ and $R^{15}$ or $R^{24}$ and $R^{25}$, together with the nitrogen atom to which they are both attached, may form a 4 to 8 membered aliphatic heterocyclic ring, which heterocyclic ring may be to optionally substituted by one or more substituents independently selected from halogen, hydroxyl and $C_{1-6}$ alkyl, which $C_{1-6}$ alkyl may be optionally substituted by one or more substituents independently selected from halogen and hydroxyl;
and X represents a pharmaceutically acceptable anion of a mono or polyvalent acid.

The compounds of formula (I) comprise an anion X associated with the positive charge on the quaternary nitrogen atom. The anion X may be any pharmaceutically acceptable anion of a mono or polyvalent (e.g. bivalent) acid. In an embodiment of the invention X may be an anion of a mineral acid, for example chloride, bromide, iodide, sulfate, nitrate or phosphate; or an anion of a suitable organic acid, for example acetate, maleate, fumarate, citrate, oxalate, succinate, tartrate, methanesulphonate, p-toluenesulphonate, benzenesulphonate or napadisylate (naphthalene-1,5-disulfonate) (e.g. a heminapadisylate).

It will be understood that certain compounds of the present invention may exist in solvated, for example hydrated, as well as unsolvated forms. It is to be understood that the present invention encompasses all such solvated forms. Certain compounds of formula (I) are capable of existing in stereoisomeric forms. It will be understood that the invention encompasses all geometric and optical isomers of the compounds of formula (I) and mixtures thereof including racemates. Tautomers and mixtures thereof also form an aspect of the present invention.

In the context of the present specification the term 'Heteroaryl' denotes aromatic ring systems comprising at least one heteroatom selected from the group consisting of nitrogen, oxygen and sulfur, and includes monocyclic and bicyclic heteroaromatic rings. Examples of 5 to 6 membered heteroaryl rings according to the present invention include thienyl, furanyl, pyridinyl, pyrimidinyl, pyrazinyl, pyridazinyl, thiazolyl, oxazolyl, oxadiazolyl, imidazolyl, isoxazolyl, isothiazolyl, pyrazolyl and triazolyl. Examples of bicyclic heteroaromatic rings include fused bicyclic ring systems wherein both rings are aromtaic or, alternatively, one ring is aromatic and the other ring is non-aromatic. In 6,6- or 6,5- fused bicyclic ring systems wherein one ring is aromatic and the other ring is non-aromatic, the non-aromatic ring may be substituted by oxo (=O) such that a ketone, amide or urea functionality is formed in the ring. Unless otherwise stated, heteroaryl groups may be linked through carbon or nitrogen. Examples of 5 to 6 membered heteroaryl rings according to the present invention include thienyl, furanyl, pyridinyl, pyrimidinyl, pyrazinyl, pyridazinyl, thiazolyl, oxazolyl, oxadiazolyl, imidazolyl, isoxazolyl, isothiazolyl, pyrazolyl and triazolyl. Examples of bicyclic heteroaromatic rings include indolyl, indazolyl, quinolinyl, isoquinolinyl, quinazolinyl and quinoxalinyl.

The term 'Aliphatic heterocyclic ring' denotes non-aromatic monocyclic and bicyclic rings comprising at least one heteroatom selected from the group consisting of nitrogen, oxygen and sulfur. Examples of 4 to 8 membered aliphatic heterocyclic rings according to the present invention include pyrrolidinyl, piperidinyl, piperazinyl, morpholinyl, homopiperazinyl, homopiperidinyl and azetidinyl.

Aryl denotes aromatic carbocyclic rings, for example phenyl or naphthyl. The term 'aliphatic carbocyclic ring' denotes non-aromatic carbocyclic rings, both monocyclic and bicyclic. Examples of 3 to 8 membered aliphatic carbocyclic rings are cyclopropyl, cyclobutyl, cyclopentyl and cyclohexyl. The term cycloalkyl denotes saturated monocyclic carbocyclic rings. Cycloalkyl groups are monocyclic, for example cyclopentyl or cyclohexyl. Halogen is for example, fluorine, chlorine or bromine.

Unless otherwise stated, in the context of the present specification alkyl groups and moieties may be straight or branched chain and include, for example, methyl, ethyl, n-propyl, iso-propyl or tert-butyl. The term alkylene denotes bivalent alkyl groups, e.g. —$CH_2$—, —$CH_2CH_2$—, and —$CH(CH_3)CH_2$—. In the context of the present specification alkylene groups may incorporate cycloalkyl rings, e.g. an example of a $C_4$ alkylene is

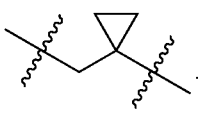

In the context of the present specification, where it is stated that a group may be optionally substituted with one or more substituents the group may be unsubstituted or substituted; when substituted the group will generally be substituted with one, two or three substituents. In general, a hydroxyl moiety will not be attached to a carbon atom which is adjacent to a nitrogen atom.

In an embodiment of the invention, $R^1$ and $R^2$ together with the carbon atom to which they are both directly attached form a 7 membered cycloalkyl ring, which cycloalkyl ring may be optionally substituted by one or more substituents independently selected from halogen, hydroxyl, $C_{1-4}$ alkoxy, $NH_2$, $NH(C_{1-4}$ alkyl), $N(C_{1-4}$ alkyl$)_2$ and $C_{1-4}$ alkyl which $C_{1-4}$ alkyl may be optionally substituted by one or more substituents independently selected from halogen and hydroxyl.

In an embodiment of the invention, $R^1$ and $R^2$ together with the carbon atom to which they are both directly attached form a 7 membered cycloalkyl ring, which cycloalkyl ring may be optionally substituted by one or more substituents independently selected from halogen, hydroxyl and $C_{1-4}$ alkyl.

In an embodiment of the invention, $R^1$ and $R^2$ together with the carbon atom to which they are both directly attached form a group of formula (VIII)

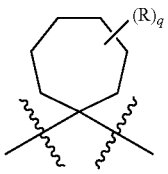

(VIII)

wherein q is 0, 1, 2, 3, 4, 5 or 6; and each R independently represents halogen, hydroxyl, $C_{1-4}$ alkoxy, $NH_2$, $NH(C_{1-4}$ alkyl), $N(C_{1-4}$ alkyl$)_2$ and $C_{1-4}$ alkyl which $C_{1-4}$ alkyl may be optionally substituted by one or more substituents independently selected from halogen and hydroxyl. When the cycloalkyl ring is substituted by more than one substituent R, carbon atoms in the cycloalkyl ring may optionally carry one or two substituents. In a further aspect of this embodiment q is 0, 1 or 2; and each R independently represents halogen, hydroxyl or $C_{1-4}$ alkyl. In a still further aspect of this embodiment, q is 0.

In an embodiment of the invention $R^3$ represents phenyl or thienyl, which phenyl or thienyl may be optionally substituted by one or more substituents independently selected from halogen, hydroxyl, $C_{1-4}$ alkoxy, $NH_2$, $NH(C_{1-4}$ alkyl), $N(C_{1-4}$ alkyl$)_2$, $OCF_3$ and $C_{1-4}$ alkyl which $C_{1-4}$ alkyl may be optionally substituted by one or more substituents independently selected from halogen and hydroxyl. In a further aspect of this embodiment, $R^3$ represents phenyl or thienyl, which phenyl or thienyl may be optionally substituted by one or more substituents independently selected from halogen, hydroxyl, $C_{1-4}$ alkyl, OMe, $CF_3$ and $OCF_3$. In a still further aspect of this embodiment, $R^3$ represents an unsubstituted phenyl or unsubstituted thienyl.

In an embodiment of the invention $R^3$ represents phenyl, which phenyl may be optionally substituted by one or more substituents independently selected from halogen, hydroxyl, $C_{1-4}$ alkoxy, $NH_2$, $NH(C_{1-4}$ alkyl), $N(C_{1-4}$ alkyl$)_2$, $OCF_3$ and $C_{1-4}$ alkyl which $C_{1-4}$ alkyl may be optionally substituted by one or more substituents independently selected from halogen and hydroxyl. In a further aspect of this embodiment, $R^3$ represents phenyl, which phenyl may be optionally substituted by one or more substituents independently selected from halogen, hydroxyl, $C_{1-4}$ alkyl, OMe, $CF_3$ and $OCF_3$. In a still further aspect of this embodiment $R^3$ represents an unsubstituted phenyl.

In an embodiment of the invention, $R^1$ and $R^2$ together with the carbon atom to which they are both directly attached form an unsubstituted 7-membered cycloalkyl ring, and $R^3$ represents unsubstituted phenyl.

In an embodiment of the invention, $R^4$ represents a group of formula (II).

In an embodiment of the invention, $R^4$ represents a group of formula (II), Y is $-CH_2-$ or $-CH_2CH_2-$, and the substitution on the ring in group (II) is in the 3 position.

In an embodiment of the invention, $R^4$ represents a group of formula (IIa),

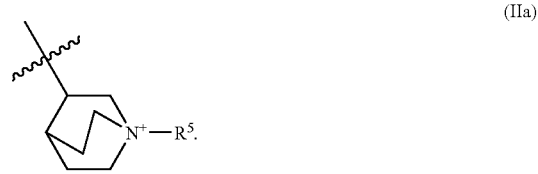

(IIa)

In an embodiment of the invention, $R^4$ represents a group of formula (IIIa).

In an embodiment of the invention, $R^4$ represents a group of formula (IIIa), a is 1, and b is 1.

In an embodiment of the invention, $R^4$ represents a group of formula (IIIb).

In an embodiment of the present invention, there is provided a compound of formula (IX), wherein $R^3$ represents phenyl or thienyl and $R^5$ and X are as defined in formula (I)

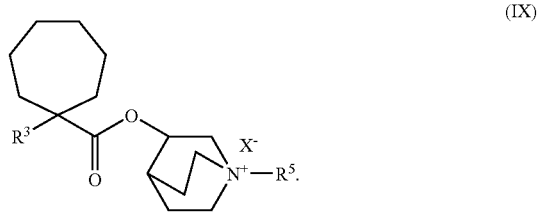

(IX)

In compounds of formula (I), $R^5$ represents a group of formula (IV)

(IV)

In an embodiment of the invention w is 0 and y is 0.
In an embodiment of the invention w is 1 and $R^6$ represents $C_{1-4}$ alkylene.

In an embodiment of the invention w is 1, $R^6$ represents $C_{1-4}$ alkylene, and y is 0.

In an embodiment of the invention, w is 1, $R^6$ represents $C_{1-4}$ alkylene, y is 1 and Q represents O, —CONH— or —C(O)O—.

In an embodiment of the invention, w is 1, $R^6$ represents $C_{1-4}$ alkylene, y is 1 and Q represents O or —CONH—.

In an embodiment of the invention, w is 1, $R^6$ represents $C_{1-4}$ alkylene, y is 1 and Q represents —CONH— or —C(O)O—.

In an embodiment of the invention, $R^7$ represents a cyclic group $Cyc^1$ or a $C_{1-4}$ alkyl group optionally substituted by a cyclic group $Cyc^2$.

In an embodiment of the invention $Cyc^1$ and $Cyc^2$ represent phenyl or a 5 to 6 membered heteroaryl, which phenyl or 5 to 6 membered heteroaryl may be optionally substituted by one or more substituents independently selected from halogen, hydroxyl, $C_{1-4}$ alkoxy, $NH_2$, $NH(C_{1-4}$ alkyl), $N(C_{1-4}$ alkyl$)_2$, $OCF_3$, phenyl and $C_{1-4}$ alkyl, which phenyl or $C_{1-4}$ alkyl may be optionally substituted by one or more substituents independently selected from halogen and hydroxyl. Examples of 5 to 6 membered heteroaryl groups according to this embodiment include isoxazolyl and furanyl.

In an embodiment of the invention $Cyc^1$ represents phenyl, naphthyl, a 5 to 6 membered heteroaryl or a 4 to 8 membered aliphatic heterocyclic ring, which phenyl, naphthyl, 5 to 6 membered heteroaryl or 4 to 8 membered aliphatic heterocyclic ring may be optionally substituted by one or more substituents independently selected from halogen, hydroxyl, $C_{1-4}$ alkoxy, $NH_2$, $NH(C_{1-4}$ alkyl), $N(C_{1-4}$ alkyl$)_2$, $OCF_3$, phenyl and $C_{1-4}$ alkyl, which phenyl or $C_{1-4}$ alkyl may be optionally substituted by one or more substituents independently selected from halogen and hydroxyl. Examples of 5 to 6 membered heteroaryl groups according to this embodiment include isoxazolyl, pyrazinyl, pyridazinyl and furanyl. Examples of 4 to 8 membered aliphatic heterocyclic rings according to this embodiment include pyrrolidinyl and morpholinyl.

In an embodiment of the invention $Cyc^2$ represents phenyl or a 5 to 6 membered heteroaryl, which phenyl or 5 to 6 membered heteroaryl may be optionally substituted by one or more substituents independently selected from halogen, hydroxyl, $C_{1-4}$ alkoxy, $NH_2$, $NH(C_{1-4}$ alkyl), $N(C_{1-4}$ alkyl$)_2$, $OCF_3$, phenyl and $C_{1-4}$ alkyl, which phenyl or $C_{1-4}$ alkyl may be optionally substituted by one or more substituents independently selected from halogen and hydroxyl. Examples of 5 to 6 membered heteroaryl groups according to this embodiment include isoxazolyl and furanyl.

In an embodiment of the invention, $R^5$ represents $C_{1-4}$ alkyl, which $C_{1-4}$ alkyl may be optionally substituted by one or more substituents independently selected from halogen, hydroxyl, $C_{1-4}$ alkoxy, phenyl, naphthyl, furanyl, thienyl and phenoxy, which $C_{1-4}$ alkoxy, phenyl, naphthyl, furanyl, thienyl or phenoxy group may be optionally substituted by one or more substituents independently selected from halogen, hydroxyl, cyano, $C_{1-4}$ alkoxy, $NH_2$, $NH(C_{1-4}$ alkyl), $N(C_{1-4}$ alkyl$)_2$, $OCF_3$ and $C_{1-4}$ alkyl which $C_{1-4}$ alkyl may be optionally substituted by one or more substituents independently selected from halogen and hydroxyl.

In an embodiment of the invention, $R^5$ represents $C_{1-4}$ alkyl, which $C_{1-4}$ alkyl may be optionally substituted by one or more substituents independently selected from halogen, hydroxyl, $C_{1-4}$ alkoxy, phenyl, furanyl and phenoxy, which phenyl, furanyl or phenoxy group may be optionally substituted by one or more substituents independently selected from halogen, hydroxyl, $C_{1-4}$ alkoxy, $NH_2$, $NH(C_{1-4}$ alkyl), $N(C_{1-4}$ alkyl$)_2$, $OCF_3$ and $C_{1-4}$ alkyl which $C_{1-4}$ alkyl may be optionally substituted by one or more substituents independently selected from halogen and hydroxyl.

In an embodiment of the invention, $R^5$ represents $C_{1-4}$ alkyl which $C_{1-4}$ alkyl may be optionally substituted by phenyl, furanyl or phenoxy, which phenyl, furanyl or phenoxy group may be optionally substituted by one or more substituents independently selected from halogen, hydroxyl, $C_{1-4}$ alkyl, OMe, $CF_3$ and $OCF_3$.

In an embodiment of the invention, $R^5$ represents

—$C_{1-4}$alkylene-Q-$R^7$;

wherein Q is O, —CONH— or —C(O)O—;
$R^7$ represents hydrogen, $Cyc^1$ or a $C_{1-4}$ alkyl group which $C_{1-4}$ alkyl group may be optionally substituted by one or more substituents independently selected from halogen, hydroxyl, phenyl and phenoxy, which phenyl and phenoxy may be optionally substituted by one or more substituents independently selected from halogen, hydroxyl, cyano, $C_{1-4}$ alkoxy and $OCF_3$; and
$Cyc^1$ represents phenyl, a 5 to 6 membered heteroaryl ring or a 4 to 8 membered aliphatic heterocyclic ring, each of which may be optionally substituted with one or more substituents independently selected from halogen, hydroxyl, $C_{1-4}$ alkoxy, $NH_2$, $NH(C_{1-4}$ alkyl), $N(C_{1-4}$ alkyl$)_2$, phenyl and $C_{1-4}$ alkyl which phenyl and $C_{1-4}$ alkyl may be optionally substituted by one or more substituents independently selected from halogen and hydroxyl.

In an embodiment of the invention, $R^5$ represents —$C_{1-4}$ alkylene-Q-$Cyc^1$;
wherein Q is —CONH—; and $Cyc^1$ is a 5 to 6 membered heteroaryl optionally substituted with one or more substituents independently selected from halogen, hydroxyl, $C_{1-4}$ alkoxy, $NH_2$, $NH(C_{1-4}$ alkyl), $N(C_{1-4}$ alkyl$)_2$, phenyl and $C_{1-4}$ alkyl which phenyl or $C_{1-4}$ alkyl may be optionally substituted by one or more substituents independently selected from halogen and hydroxyl. Examples of a 5 to 6 membered heteroaryl according to this embodiment include isoxazolyl, pyrazinyl and pyridazinyl.

In an embodiment of the invention, $R^5$ represents —$CH_2$-Q-$Cyc^1$;
wherein Q is —CONH—; and $Cyc^1$ is a 5 to 6 membered heteroaryl optionally substituted with one or more substituents independently selected from halogen, hydroxyl, $C_{1-4}$ alkoxy, $NH_2$, $NH(C_{1-4}$ alkyl), $N(C_{1-4}$ alkyl$)_2$, phenyl and $C_{1-4}$ alkyl which phenyl or $C_{1-4}$ alkyl may be optionally substituted by one or more substituents independently selected from halogen and hydroxyl. Examples of a 5 to 6 membered heteroaryl according to this embodiment include isoxazolyl, pyrazinyl and pyridazinyl.

In an embodiment of the invention, $R^5$ represents —$CH_2$-Q-$Cyc^1$;
wherein Q is —CONH—; and $Cyc^1$ is a 5 to 6 membered heteroaryl optionally substituted with $C_{1-4}$ alkyl. Examples of a 5 to 6 membered heteroaryl according to this embodiment include isoxazolyl, pyrazinyl and pyridazinyl.

In an embodiment of the invention, $R^5$ represents —$C_{1-4}$ alkylene-Q-$Cyc^1$;
wherein Q is —CONH—; $Cyc^1$ is a 5 membered heteroaryl optionally substituted with one or more substituents independently selected from halogen and $C_{1-4}$ alkyl. An example of a 5 membered heteroaryl according to this embodiment is isoxazolyl.

In an embodiment of the invention, $R^8$ is hydrogen.

In an embodiment of the invention, $R^9$ and $R^{18}$ each independently represent $C_{1-4}$ alkyl, which $C_{1-4}$ alkyl may be optionally substituted by one or more substituents independently selected from halogen and hydroxyl. In an embodiment of the invention, $R^9$ and $R^{18}$ each independently represent $C_{1-4}$ alkyl.

In an embodiment of the invention, $R^{10}$, $R^{11}$, $R^{12}$, $R^{13}$, $R^{14}$, $R^{15}$, $R^{16}$, $R^{17}$, $R^{19}$, $R^{20}$, $R^{21}$, $R^{22}$, $R^{23}$, $R^{24}$, $R^{25}$ and $R^{26}$ each independently represent hydrogen or $C_{1-4}$ alkyl, which $C_{1-4}$ alkyl may be optionally substituted by one or more substituents independently selected from halogen and hydroxyl. In an embodiment of the invention, $R^{10}$, $R^{11}$, $R^{12}$, $R^{13}$, $R^{14}$, $R^{15}$, $R^{16}$, $R^{17}$, $R^{19}$, $R^{20}$, $R^{21}$, $R^{22}$, $R^{23}$, $R^{24}$, $R^{25}$ and $R^{26}$ each independently represent hydrogen or $C_{1-4}$ alkyl.

A further aspect of the present invention provides a compound of formula (X)

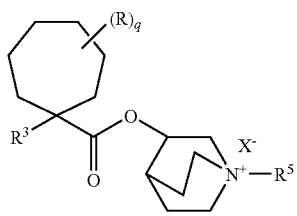

(X)

wherein q is 0, 1 or 2; each R independently represents halogen, hydroxyl or $C_{1-4}$ alkyl; $R^3$ represents phenyl, which phenyl may be optionally substituted by one or more substituents independently selected from halogen, hydroxyl, $C_{1-4}$ alkyl, OMe, $CF_3$ and $OCF_3$; $R^5$ represents $C_{1-4}$ alkyl which $C_{1-4}$ alkyl may be optionally substituted by phenyl, furanyl or phenoxy, which phenyl, furanyl or phenoxy group may be optionally substituted by one or more substituents independently selected from halogen, hydroxyl, $C_{1-4}$ alkyl, OMe, $CF_3$ and $OCF_3$; and X represents a pharmaceutically acceptable anion of a mono or polyvalent acid.

A further aspect of the present invention provides a compound of formula (XI)

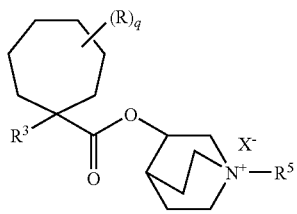

(XI)

wherein q is 0, 1 or 2; each R independently represents halogen, hydroxyl or $C_{1-4}$ alkyl; $R^3$ represents phenyl, which phenyl may be optionally substituted by one or more substituents independently selected from halogen, hydroxyl, $C_{1-4}$ alkyl, OMe, $CF_3$ and $OCF_3$;
$R^5$ represents $C_{1-4}$ alkyl, which $C_{1-4}$ alkyl may be optionally substituted by one or more substituents independently selected from halogen, hydroxyl, $C_{1-4}$ alkoxy, phenyl, naphthyl, furanyl, thienyl and phenoxy, which $C_{1-4}$ alkoxy, phenyl, naphthyl, furanyl, thienyl or phenoxy group may be optionally substituted by one or more substituents independently selected from halogen, hydroxyl, cyano, $C_{1-4}$ alkoxy, $NH_2$, $NH(C_{1-4}$ alkyl), $N(C_{1-4}$ alkyl$)_2$, $OCF_3$ and $C_{1-4}$ alkyl which $C_{1-4}$ alkyl may be optionally substituted by one or more substituents independently selected from halogen and hydroxyl;

and X represents a pharmaceutically acceptable anion of a mono or polyvalent acid.

A further aspect of the present invention provides a compound of formula (XII)

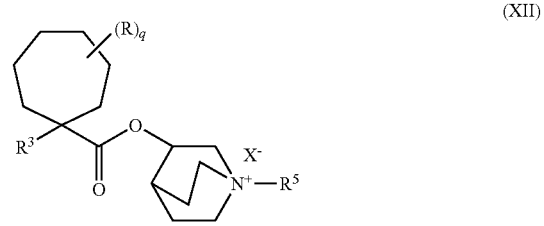

(XII)

wherein q is 0, 1 or 2; each R independently represents halogen, hydroxyl or $C_{1-4}$ alkyl; $R^3$ represents phenyl, which phenyl may be optionally substituted by one or more substituents independently selected from halogen, hydroxyl, $C_{1-4}$ alkyl, OMe, $CF_3$ and $OCF_3$; $R^5$ represents —$C_{1-4}$ alkylene-Q-$Cyc^1$; wherein Q is —CONH—; $Cyc^1$ is a 5 membered heteroaryl optionally substituted with one or more substituents independently selected from halogen and $C_{1-4}$ alkyl; and X represents a pharmaceutically acceptable anion of a mono or polyvalent acid.

A further aspect of the present invention provides a compound of formula (XIII)

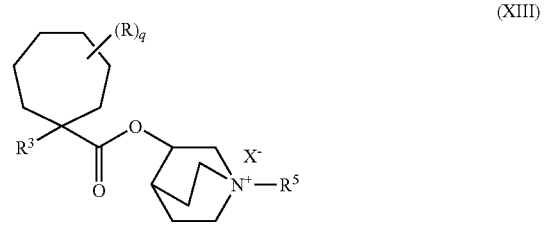

(XIII)

wherein q is 0, 1 or 2; each R independently represents halogen, hydroxyl or $C_{1-4}$ alkyl; $R^3$ represents phenyl, which phenyl may be optionally substituted by one or more substituents independently selected from halogen, hydroxyl, $C_{1-4}$ alkyl, OMe, $CF_3$ and $OCF_3$;
$R^5$ represents —$C_{1-4}$ alkylene-Q-$R^7$;
Q is O, —CONH— or —C(O)O—;
$R^7$ represents hydrogen, $Cyc^1$ or a $C_{1-4}$ alkyl group which $C_{1-4}$ alkyl group may be optionally substituted by one or more substituents independently selected from halogen, hydroxyl, phenyl and phenoxy, which phenyl and phenoxy may be optionally substituted by one or more substituents independently selected from halogen, hydroxyl, cyano, $C_{1-4}$ alkoxy and $OCF_3$; and
$Cyc^1$ represents phenyl, a 5 to 6 membered heteroaryl ring or a 4 to 8 membered aliphatic heterocyclic ring, each of which may be optionally substituted with one or more substituents independently selected from halogen, hydroxyl, $C_{1-4}$ alkoxy, $NH_2$, $NH(C_{1-4}$ alkyl), $N(C_{1-4}$ alkyl$)_2$, phenyl and $C_{1-4}$ alkyl which phenyl and $C_{1-4}$ alkyl may be optionally substituted by one or more substituents independently selected from halogen and hydroxyl; and X represents a pharmaceutically acceptable anion of a mono or polyvalent acid.

Compounds of the present invention wherein $R^4$ represents a group of formula (IIa) contain a chiral centre at the 3-position on the quinuclidinyl ring, i.e. at the position marked with an asterix (*) in the representation of formula (IIa) herein below.

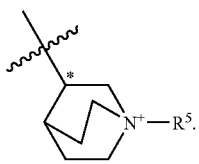

(IIa)

In an embodiment of the present invention, $R^4$ represents a group of formula (IIa) wherein the stereochemical configuration at the 3-position of the quinuclidinyl ring is (R), as designated by the Cahn-Ingold-Prelog system. The (R) stereoisomer of this embodiment may be present as a mixture with the (S) stereoisomer. For example, the (R) stereoisomer may be present in a racemic (1:1) mixture with the (S) stereoisomer. However, a further aspect of this embodiment provides an optically pure compound of formula (I) wherein $R^4$ represents a group of formula (IIa) and wherein the stereochemical configuration at the 3-position of the quinuclidinyl ring is (R).

In the context of the present specification, the term optically pure is defined in terms of enantiomeric excess (e.e.), which is calculated from the ratio of the difference between the amounts of the respective enantiomers present and the sum of these amounts, expressed as a percentage. To illustrate, a preparation containing 95% of one enantiomer and 5% of another enantiomer has an enantiomeric excess (e.e.) of 90% [i.e. (95-5)/(95+5)×100]. An optically pure compound according to the present invention has an e.e. of at least 90%. In an embodiment of the invention, an optically pure compound has an e.e. of at least 95%. In a further embodiment of the invention, an optically pure compound has an e.e. of at least 98%.

In a further embodiment the present invention provides a compound of formula (IX) as defined herein above, wherein the stereochemical configuration at the 3-position of the quinuclidinyl ring is (R). In a further aspect of this embodiment the compound of formula (IX) is optically pure.

In a further embodiment the present invention provides a compound of formula (X) as defined herein above, wherein the stereochemical configuration at the 3-position of the quinuclidinyl ring is (R). In a further aspect of this embodiment the compound of formula (X) is optically pure.

In a further embodiment the present invention provides a compound of formula (XI) as defined herein above, wherein the stereochemical configuration at the 3-position of the quinuclidinyl ring is (R). In a further aspect of this embodiment the compound of formula (XI) is optically pure.

In a further embodiment the present invention provides a compound of formula (XII) as defined herein above, wherein the stereochemical configuration at the 3-position of the quinuclidinyl ring is (R). In a further aspect of this embodiment the compound of formula (XII) is optically pure.

In a further embodiment the present invention provides a compound of formula (XIII) as defined herein above, wherein the stereochemical configuration at the 3-position of the quinuclidinyl ring is (R). In a further aspect of this embodiment the compound of formula (XIII) is optically pure.

In an embodiment of the present invention, $R^5$ does not represent methyl.

In an embodiment of the present invention, $R^5$ does not represent methyl or unsubstituted benzyl.

In an embodiment of the present invention, $R^5$ does not represent methyl, unsubstituted benzyl or a substituted benzyl.

In an embodiment of the present invention, there is provided a compound of formula (IB),

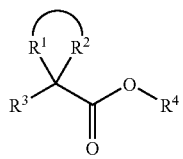

(IB)

wherein $R^1$ and $R^2$ together with the carbon atom to which they are both directly attached form a 7 membered aliphatic carbocyclic ring which may be optionally substituted by one or more substituents independently selected from halogen, hydroxyl, $C_{1-6}$ alkoxy, $NH_2$, $NH(C_{1-6}$ alkyl), $N(C_{1-6}$ alkyl$)_2$ and $C_{1-6}$ alkyl which $C_{1-6}$ alkyl may be optionally substituted by one or more substituents independently selected from halogen and hydroxyl;

$R^3$ represents phenyl or a 5 to 6 membered heteroaryl ring, each of which may be optionally substituted by one or more substituents independently selected from halogen, cyano, nitro, SH, $S(O)_{0-2}R^9$, $NR^{10}R^{11}$, $S(O)_2NR^{12}R^{13}$, $C(O)NR^{14}R^{15}$, $C(O)_2R^{16}$, $NR^{17}S(O)_2R^{18}$, $NR^{19}C(O)R^{20}$, $NR^{21}C(O)_2R^{22}$, $NR^{23}C(O)NR^{24}R^{25}$, $OR^{26}$ and $C_{1-6}$ alkyl which $C_{1-6}$ alkyl may be optionally substituted by one or more substituents independently selected from halogen, hydroxyl, $C_{1-6}$ alkoxy, $NH_2$, $NH(C_{1-6}$ alkyl) and $N(C_{1-6}$ alkyl$)_2$;

$R^4$ represents a group of formula (II) or (IIIa) or (IIIb);

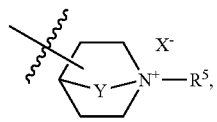

(II)

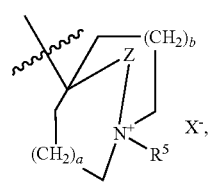

(IIIa)

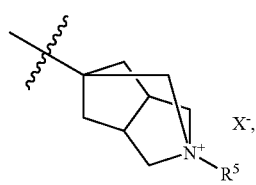

(IIIb)

wherein

Y is —$CH_2$—, —$CH_2CH_2$— or —$CH_2CH_2CH_2$— and the substitution on the ring in group (II) may be in the 3 or 4 positions;

a is 1 or 2;

b is 1 or 2;

Z is —$CH_2$—;

$R^5$ represents a group of formula (IV)

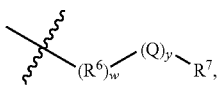

(IV)

wherein
w is 0 or 1;
$R^6$ represents $C_{1-4}$ alkylene optionally substituted by one or more substituents independently selected from halogen, hydroxyl, $C_{1-6}$ alkoxy, $NH_2$, $NH(C_{1-6}$ alkyl) and $N(C_{1-6}$ alkyl)$_2$;
when w is 0, y is 0; when w is 1, y is 0 or 1;
Q represents O, $S(O)_{0-2}$, $NR^8$, —$CONR^8$—, —$SO_2NR^8$—, —$NR^8CO$—, —$NR^8SO_2$—, —$OC(O)$—, —$C(O)O$—, —C≡C— or ethynylene;
$R^7$ represents a cyclic group $Cyc^1$ or a $C_{1-4}$ alkyl group optionally substituted by one or more substituents independently selected from halogen, hydroxyl, $C_{1-4}$ alkoxy, $NH_2$, $NH(C_{1-4}$ alkyl), $N(C_{1-4}$ alkyl)$_2$ and a cyclic group $Cyc^2$;
$Cyc^1$ and $Cyc^2$ represent aryl, heteroaryl, a 3 to 8 membered aliphatic carbocyclic ring or a 4 to 8 membered aliphatic heterocyclic ring, each of which may be optionally substituted by one or more substituents independently selected from halogen, cyano, nitro, SH, $S(O)_{0-2}R^9$, $NR^{10}R^{11}$, $S(O)_2NR^{12}R^{13}$, $C(O)NR^{14}R^{15}$, $C(O)_2R^{16}$, $NR^{17}S(O)_2R^{18}$, $NR^{19}C(O)R^{20}$, $NR^{21}C(O)_2R^{22}$, $NR^{23}C(O)NR^{24}R^{25}$, $OR^{26}$, phenyl and $C_{1-6}$ alkyl which phenyl or $C_{1-6}$ alkyl may be optionally substituted by one or more substituents independently selected from halogen, hydroxyl, $C_{1-6}$ alkoxy, $NH_2$, $NH(C_{1-6}$ alkyl) and $N(C_{1-6}$ alkyl)$_2$;
$R^8$ represents hydrogen or $C_{1-6}$ alkyl;
$R^9$ and $R^{18}$ each independently represent $C_{1-6}$ alkyl, which $C_{1-6}$ alkyl may be optionally substituted by one or more substituents independently selected from halogen, hydroxyl, $C_{1-6}$ alkoxy, $NH_2$, $NH(C_{1-6}$ alkyl) and $N(C_{1-6}$ alkyl)$_2$; and $R^{10}$, $R^{11}$, $R^{12}$, $R^{13}$, $R^{14}$, $R^{15}$, $R^{16}$, $R^{17}$, $R^{19}$, $R^{20}$, $R^{21}$, $R^{22}$, $R^{23}$, $R^{24}$, $R^{25}$ and $R^{26}$ each independently represent hydrogen or $C_{1-6}$ alkyl, which $C_{1-6}$ allyl may be optionally substituted by one or more substituents independently selected from halogen, hydroxyl, $C_{1-6}$ alkoxy, $NH_2$, $NH(C_{1-6}$ alkyl) and $N(C_{1-6}$ alkyl)$_2$; or any of $R^{10}$ and $R^{11}$, $R^{12}$ and $R^{13}$, $R^{14}$ and $R^{15}$ or $R^{24}$ and $R^{25}$, together with the nitrogen atom to which they are both attached, may form a 4 to 8 membered aliphatic heterocyclic ring, which heterocyclic ring may be optionally substituted by one or more substituents independently selected from halogen, hydroxyl and $C_{1-6}$ alkyl, which $C_{1-6}$ alkyl may be optionally substituted by one or more substituents independently selected from halogen and hydroxyl;
and X represents a pharmaceutically acceptable anion of a mono or polyvalent acid.

For compounds of formula (IB), embodiments of the invention include those wherein each of $R^1$, $R^2$, $R^3$ and $R^4$, are as defined herein above in embodiments of the invention concerning compounds of formula (I).

In an embodiment of the invention, the compound of formula (I) is selected from:
(3R)-1-Methyl-3-{[(1-phenylcycloheptyl)carbonyl]oxy}-1-azoniabicyclo[2.2.2]octane X,
(3R)-1-(3-Phenoxypropyl)-3-{[(1-phenylcycloheptyl)carbonyl]oxy}-1-azoniabicyclo[2.2.2]octane X,
(3R)-1-[2-(Isoxazol-3-ylamino)-2-oxoethyl]-3-{[(1-phenylcycloheptyl)carbonyl]oxy}-1-azoniabicyclo[2.2.2]octane X,
(3R)-1-(4-Fluorobenzyl)-3-{[(1-phenylcycloheptyl)carbonyl]oxy}-1-azoniabicyclo[2.2.2]octane X,
(3R)-1-Benzyl-3-{[(1-phenylcycloheptyl)carbonyl]oxy}-1-azoniabicyclo[2.2.2]octane X,
(3R)-3-{[(1-Phenylcycloheptyl)carbonyl]oxy}-1-[3-(trifluoromethoxy)benzyl]-1-azoniabicyclo[2.2.2]octane X,
(3R)-1-(3,4-Difluorobenzyl)-3-{[(1-phenylcycloheptyl)carbonyl]oxy}-1-azoniabicyclo[2.2.2]octane X,
(3R)-3-{[(1-Phenylcycloheptyl)carbonyl]oxy}-1-{[5-(trifluoromethyl)-2-furyl]methyl}-1-azoniabicyclo[2.2.2]octane X,
(3R)-1-(3-Methoxybenzyl)-3-{[(1-phenylcycloheptyl)carbonyl]oxy}-1-azoniabicyclo[2.2.2]octane X,
(3R)-1-(2-Phenoxyethyl)-3-{[(1-phenylcycloheptyl)carbonyl]oxy}-1-azoniabicyclo[2.2.2]octane X,
(3R)-1-[2-(Benzyloxy)ethyl]-3-{[(1-phenylcycloheptyl)carbonyl]oxy}-1-azoniabicyclo[2.2.2]octane X,
(3R)-1-[2-(Isoxazol-3-ylamino)-2-oxoethyl]-3-({[1-(2-thienyl)cycloheptyl]carbonyl}oxy)-1-azoniabicyclo[2.2.2]octane X,
(3R)-1-(2-Oxo-2-pyrrolidin-1-ylethyl)-3-{[(1-phenylcycloheptyl)carbonyl]oxy}-1-azoniabicyclo[2.2.2]octane X,
(3R)-1-(2-Morpholin-4-yl-2-oxoethyl)-3-{[(1-phenylcycloheptyl)carbonyl]oxy}-1-azoniabicyclo[2.2.2]octane X,
(3R)-1-[2-Oxo-2-(pyrazin-2-ylamino)ethyl]-3-{[(1-phenylcycloheptyl)carbonyl]oxy}-1-azoniabicyclo[2.2.2]octane X,
(3R)-1-[2-Oxo-2-(pyridazin-3-ylamino)ethyl]-3-{[(1-phenylcycloheptyl)carbonyl]oxy}-1-azoniabicyclo[2.2.2]octane X,
(3R)-1-{2-Oxo-2-[(2-phenoxyethyl)amino]ethyl}-3-{[(1-phenylcycloheptyl)carbonyl]oxy}-1-azoniabicyclo[2.2.2]octane X,
(3R)-1-[2-(3-Fluorophenyl)-2-oxoethyl]-3-{[(1-phenylcycloheptyl)carbonyl]oxy}-1-azoniabicyclo[2.2.2]octane X,
(3R)-1-{2-[(5-Methylisoxazol-3-yl)amino]-2-oxoethyl}-3-{[(1-phenylcycloheptyl)carbonyl]oxy}-1-azoniabicyclo[2.2.2]octane X,
(3R)-1-{2-[(6-Chloropyridazin-3-yl)amino]-2-oxoethyl}-3-{[(1-phenylcycloheptyl)carbonyl]oxy}-1-azoniabicyclo[2.2.2]octane X,
(3R)-1-{2-[(3-Fluorophenyl)amino]-2-oxoethyl}-3-{[(1-phenylcycloheptyl)carbonyl]oxy}-1-azoniabicyclo[2.2.2]octane X,
(3R)-1-[2-(2-Naphthyl)ethyl]-3-{[(1-phenylcycloheptyl)carbonyl]oxy}-1-azoniabicyclo[2.2.2]octane X,
(3R)-1-[2-(3-Methoxyphenyl)ethyl]-3-{[(1-phenylcycloheptyl)carbonyl]oxy}-1-azoniabicyclo[2.2.2]octane X,
(3R)-1-[2-(5-Methyl-2-thienyl)ethyl]-3-{[(1-phenylcycloheptyl)carbonyl]oxy}-1-azoniabicyclo[2.2.2]octane X,
(3R)-3-{[(1-Phenylcycloheptyl)carbonyl]oxy}-1-(2-phenylethyl)-1-azoniabicyclo[2.2.2]octane X,
(3R)-3-{[(1-Phenylcycloheptyl)carbonyl]oxy}1-{2-[3-(trifluoromethyl)phenyl]ethyl}-1-azoniabicyclo[2.2.2]octane X,
(3R)-1-[2-(1,3-Benzodioxol-5-yl)ethyl]-3-{[(1-phenylcycloheptyl)carbonyl]oxy}-1-azoniabicyclo[2.2.2]octane X,
(3R)-1-[2-(4-Cyanophenyl)ethyl]-3-{[(1-phenylcycloheptyl)carbonyl]oxy}-1-azoniabicyclo[2.2.2]octane X,
(3R)-1-[2-(1,3-Dioxo-1,3-dihydro-2H-isoindol-2-yl)ethyl]-3-{[(1-phenylcycloheptyl)carbonyl]oxy}-1-azoniabicyclo[2.2.2]octane X,
(3R)-1-{2-[(6-Chloropyrazin-2-yl)amino]-2-oxoethyl}-3-{[(1-phenylcycloheptyl)carbonyl]oxy}-1-azoniabicyclo[2.2.2]octane X, (3R)-1-{[1-(4-Chlorophenyl)cyclopropyl]methyl}-3-{[(1-phenylcycloheptyl)carbonyl]oxy}-1-azoniabicyclo[2.2.2]octane X, (3R)-1-{2-[(5-Methylpyrazin-2-yl)amino]-2-oxoethyl}-3-{[(1-phenylcycloheptyl)carbonyl]oxy}-1-azoniabicyclo[2.2.2]octane X, (3R)-1-(Carboxymethyl)-3-{[(1-phenylcycloheptyl)carbonyl]oxy}-1-azoniabicyclo[2.2.2]octane X, (3R)-1-[2-(3-Chlorophenyl)ethyl]-3-{[(1-phenylcycloheptyl)carbonyl]oxy}-1-azoniabicyclo[2.2.2]octane X, (3R)-1-(2-Amino-2-oxoethyl)-3-{[(1-phenylcycloheptyl)carbonyl]oxy}-1-azoniabicyclo[2.2.2]octane X, (3R)-1-{2-Oxo-2-[(3-phenylpropyl)amino]ethyl}-3-{[(1-phenylcycloheptyl)carbonyl]oxy}-1-azoniabicyclo[2.2.2]octane X, and (3R)-1-[2-(3-Chloro-4-methoxyphenyl)ethyl]-3-{[(1-phenylcycloheptyl)carbonyl]oxy}-1-azoniabicyclo[2.2.2]octane X, (3R)-1-{2-[(3-Methylisoxazol-5-yl)amino]-2-oxoethyl}-3-{[(1-phenylcycloheptyl)carbonyl]oxy}-1-azoniabicyclo[2.2.2]octane X;

wherein X represents a pharmaceutically acceptable anion of a mono or polyvalent acid. Pharmaceutically acceptable anions according to this embodiment include chloride, bromide and iodide.

In a further aspect, the present invention provides a process for the preparation of compounds of formula (I), which comprises reacting a compound of formula (XIV) wherein $R^1$, $R^2$ and $R^3$ are as defined in formula (I), or a $C_{1-6}$alkyl ester, acid anhydride or acid halide thereof,

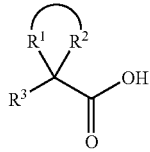
(XIV)

with a compound of formula (XV) or formula (XVIa) or formula (XVIb), wherein Y, Z, a and b are as defined in formula (I) and the hydroxyl group in (XV) is at the 3 or 4 position

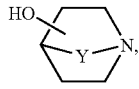
(XV)

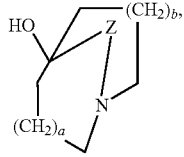
(XVIa)

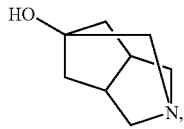
(XVIb)

to yield a compound of formula (Va) or (Vb) or (Vc)

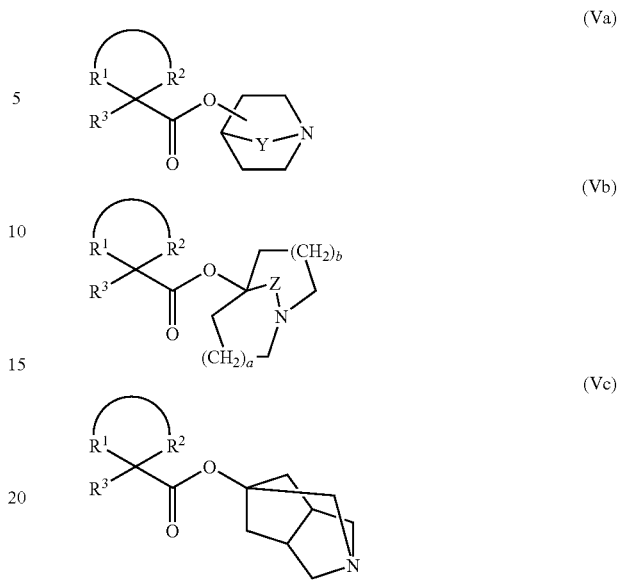

wherein $R^1$, $R^2$ and $R^3$ are as defined in claim 1 and subsequently reacting (Va) or (Vb) or (Vc) with a compound $R^5$-LG, wherein LG is a leaving group (e.g. halogen) and $R^5$ is as defined in formula (I): and optionally converting the compound to a further compound of formula (I), forming a pharmaceutically acceptable salt with an anion of a mono or polyvalent acid.

The reaction of compound (XIV) (or $C_{1-6}$alkyl ester thereof) with compound (XV) or (XVIa) or (XVIb) may be conveniently conducted in the presence of a suitable solvent such as heptane, toluene or dichloromethane at a temperature in the range of 0 to 100° C. In one embodiment of the invention, compound (XIV) may conveniently take the form of an acid halide (e.g. chloride) as may be prepared by reacting the acid with a suitable reagent (e.g. thionyl chloride or oxalyl chloride) in a suitable solvent such as dichloromethane or toluene, at a temperature in the range of 0 to 100° C.

The reaction of compounds (V) and $R^5$-LG may be conveniently conducted in the presence of a suitable solvent such as dichloromethane or acetonitrile at a temperature in the range of 0 to 100° C.

Compounds of formula (XIV) may be conveniently prepared by addition of an organometallic compound $R^3$Met (XVII), wherein $R^3$ is as defined in formula (I) and Met is a suitable metal, with a compound of formula $R^1R^2C(=O)$ (XVIII) wherein $R^1$ and $R^2$ are as defined in formula (I), to form alcohol $R^1R^2R^3$COH (XIX). Alcohol (XIX) may then be converted to an alkyl ether and the alkyl ether subsequently converted to acid (XIV) by treating the alkyl ether with an alkali metal and quenching with $CO_2$. The acid (XIV) may optionally be converted to its $C_{1-6}$alkyl ester, acid anhydride or acid halide.

The reaction of compounds (XVII) and (XVIII) may be conveniently conducted in the presence of a suitable solvent such as tetrahydrofuran or diethyl ether at a temperature in the range of −20° C. to 100° C. In compounds of structure $R^3$Met (XVII) Met may be lithium, sodium, potassium or magnesium halide. Conversion of the alcohol $R^1R^2R^3$COH (XIX) to its alkyl ether may conveniently be performed by treatment with a compound $C_{1-6}$alkyl-LG wherein LG is a leaving group (e.g. halogen), in a suitable solvent such as dichloromethane, tetrahydrofuran, or acetonitrile with a suitable base such as triethylamine, diisopropylethylamine or sodium hydride at a temperature range of 0° C. to 90° C. The resulting alkyl ether may then be conveniently converted to a structure of formula (XIV) by treatment with a mixture of sodium and potassium in a solvent such as diethyl ether at a temperature in the range of 0° C. to −80° C. and quenching with $CO_2$. Further elaboration of the acid may be performed to furnish a $C_{1-6}$alkyl ester by treatment with a $C_{1-6}$alcohol in a solvent such as methanol with an acid catalyst such as toluenesulfonic acid or by treatment of the acid with TMS-diazomethane or diazomethane in a solvent mixture such as tetrahydrofuran/methanol. Further elaboration of the acid may be performed to furnish an acid anhydride or acid halide by treatment with oxalyl chloride or sulfonyl chloride in a solvent such as dichloromethane at a temperature in the range of −20° C. to 40° C.

Compounds (XV), (XVIa) and (XVIb) are either commercially available or may be made by methods according or analogous to those described in the literature; see for example EP188255, Leonard et. al. J. Org. Chem. 1963, 28, 1499, and U.S. Pat. No. 5,318,977.

It will be appreciated by those skilled in the art that in the processes of the present invention certain functional groups such as hydroxyl, carboxyl or amino groups in the starting reagents or intermediate compounds may need to be protected by protecting groups. Thus, the preparation of the compounds of formula (I) may involve at a certain stage the removal of one or more protecting groups. The protection and deprotection of functional groups is described in 'Protective Groups in Organic Synthesis', 2nd edition, T. W. Greene and P. G. M. Wuts, Wiley-Interscience (1991) and 'Protecting Groups', P. J. Kocienski, Georg Thieme Verlag (1994).

The compounds of the present invention display beneficial pharmaceutical properties. For example, the compounds of the invention display higher potencies than analogous compounds containing cyclopentyl, cyclohexyl and cyclooctyl rings. Moreover, the compounds also display higher plasma protein binding than analogous compounds comprising cyclohexyl and cyclopentyl rings. Higher plasma protein binding may be an advantageous property for compounds administered via inhalation as it can lessen the impact of any systemic effect the compound may have.

Compounds of formula (Va) and (Vb) and (Vc) have not been prepared previously. Moreover, these non-quaternised compounds also display activity as anticholinergic agents and are of interest for use in treating conditions of the urinary tract, such as overactive bladder. Accordingly, the present invention further provides a compound of formula (V), or an acid addition salt thereof

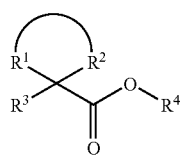

(V)

wherein
$R^1$ and $R^2$ together with the carbon atom to which they are both directly attached form a 7 membered aliphatic carbocyclic ring which may be optionally substituted by one or more substituents independently selected from halogen, hydroxyl, $C_{1-6}$ alkoxy, $NH_2$, $NH(C_{1-6}$ alkyl), $N(C_{1-6}$ alkyl)$_2$ and $C_{1-6}$ alkyl which $C_{1-6}$ alkyl may be optionally substituted by one or more substituents independently selected from halogen and hydroxyl;

$R^3$ represents phenyl or a 5 to 6 membered heteroaryl ring, each of which may be optionally substituted by one or more substituents independently selected from halogen, cyano, nitro, SH, $S(O)_{0-2}R^9$, $NR^{10}R^{11}$, $S(O)_2NR^{12}R^{13}$, $C(O)NR^{14}R^{15}$, $C(O)_2R^{16}$, $NR^{17}S(O)_2R^{18}$, $NR^{19}C(O)R^{20}$, $NR^{21}C(O)_2R^{22}$, $NR^{23}C(O)NR^{24}R^{25}$, $OR^{26}$ and $C_{1-6}$ alkyl which $C_{1-6}$ alkyl may be optionally substituted by one or more substituents independently selected from halogen, hydroxyl, $C_{1-6}$ alkoxy, $NH_2$, $NH(C_{1-6}$ alkyl) and $N(C_{1-6}$ alkyl)$_2$;

$R^4$ represents a group of formula (VI) or (VIIa) or (VIIb);

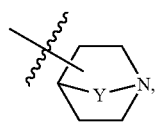

(VI)

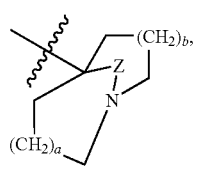

(VIIb)

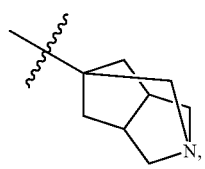

(VIIb)

wherein
Y is —$CH_2$—, —$CH_2CH_2$— or —$CH_2CH_2CH_2$— and the substitution on the ring in group (VI) may be in the 3 or 4 positions;
a is 1 or 2;
b is 1 or 2; and
Z is —$CH_2$—

For compounds of formula (V), embodiments of the invention include those wherein each of $R^1$, $R^2$, $R^3$ and $R^4$ are as defined herein above in embodiments of the invention concerning compounds of formula (I).

Acid addition salts of compounds of formula (V) include the hydrochloride, hydrobromide, phosphate, acetate, fumarate, maleate, tartrate, citrate, oxalate, methanesulphonate or p-toluenesulphonate salt.

Compounds of formula (V) according to the present invention include:
(3R)-3-{[(1-Phenylcycloheptyl)carbonyl]oxy}-1-azabicyclo[2.2.2]octane, and
(3R)-3-{[(1-Thienylcycloheptyl)carbonyl]oxy}-1-azabicyclo[2.2.2]octane
and pharmaceutically acceptable acid addition salts thereof.

The compounds of the invention have activity as pharmaceuticals, in particular as anticholinergic agents including muscarinic receptor (M1, M2, and M3) antagonists, in particular M3 antagonists. Diseases and conditions which may be treated with the compounds include:

1. respiratory tract: obstructive diseases of the airways including: asthma, including bronchial, allergic, intrinsic, extrinsic, exercise-induced, drug-induced (including aspirin and NSAID-induced) and dust-induced asthma, both intermittent and persistent and of all severities, and other causes of airway hyper-responsiveness; chronic obstructive pulmonary disease (COPD); bronchitis, including infectious and eosinophilic bronchitis; emphysema; bronchiectasis; cystic fibrosis; sarcoidosis; farmer's lung and related diseases; hypersensitivity pneumonitis; lung fibrosis, including cryptogenic fibrosing alveolitis, idiopathic interstitial pneumonias, fibrosis complicating anti-neoplastic therapy and chronic infection, including tuberculosis and aspergillosis and other fungal infections; complications of lung transplantation; vasculitic and thrombotic disorders of the lung vasculature, and pulmonary hypertension; antitussive activity including treatment of chronic cough associated with inflammatory and secretory conditions of the airways, and iatrogenic cough; acute and chronic rhinitis including rhinitis medicamentosa, and vasomotor rhinitis; perennial and seasonal allergic rhinitis including rhinitis nervosa (hay fever); nasal polyposis; acute viral infection including the common cold, and infection due to respiratory syncytial virus, influenza, coronavirus (including SARS) and adenovirus;

2. bone and joints: arthritides associated with or including osteoarthritis/osteoarthrosis, both primary and secondary to, for example, congenital hip dysplasia; cervical and lumbar spondylitis, and low back and neck pain; rheumatoid arthritis and Still's disease; seronegative spondyloarthropathies including ankylosing spondylitis, psoriatic arthritis, reactive arthritis and undifferentiated spondarthropathy; septic arthritis and other infection-related arthopathies and bone disorders such as tuberculosis, including Potts' disease and Poncet's syndrome; acute and chronic crystal-induced synovitis including urate gout, calcium pyrophosphate deposition disease, and calcium apatite related tendon, bursal and synovial inflammation; Behcet's disease; primary and secondary Sjogren's syndrome; systemic sclerosis and limited scleroderma; systemic lupus erythematosus, mixed connective tissue disease, and undifferentiated connective tissue disease; inflammatory myopathies including dermatomyositits and polymyositis; polymalgia rheumatica; juvenile arthritis including idiopathic inflammatory arthritides of whatever joint distribution and associated syndromes, and rheumatic fever and its systemic complications; vasculitides including giant cell arteritis, Takayasu's arteritis, Churg-Strauss syndrome, polyarteritis nodosa, microscopic polyarteritis, and vasculitides associated with viral infection, hypersensitivity reactions, cryoglobulins, and paraproteins; low back pain; Familial Mediterranean fever, Muckle-Wells syndrome, and Familial Hibernian Fever, Kikuchi disease; drug-induced arthalgias, tendonititides, and myopathies;

3. pain and connective tissue remodelling of musculoskeletal disorders due to injury [for example sports injury] or disease: althitides (for example rheumatoid arthritis, osteoarthritis, gout or crystal arthropathy), other joint disease (such as intervertebral disc degeneration or temporomandibular joint degeneration), bone remodelling disease (such as osteoporosis, Paget's disease or osteonecrosis), polychondritits, scleroderma, mixed connective tissue disorder, spondyloarthropathies or periodontal disease (such as periodontitis);

4. skin: psoriasis, atopic dermatitis, contact dermatitis or other eczematous dermatoses, and delayed-type hypersensitivity reactions; phyto- and photodermatitis; seborrhoeic dermatitis, dermatitis herpetiformis, lichen planus, lichen sclerosus et atrophica, pyoderma gangrenosum, skin sarcoid, discoid lupus erythematosus, pemphigus, pemphigoid, epidermolysis bullosa, urticaria, angioedema, vasculitides, toxic erythemas, cutaneous eosinophilias, alopecia areata, male-pattern baldness, Sweet's syndrome, Weber-Christian syndrome, erythema multiforme; cellulitis, both infective and non-infective; panniculitis; cutaneous lymphomas, non-melanoma skin cancer and other dysplastic lesions; drug-induced disorders including fixed drug eruptions;

5. eyes: blepharitis; conjunctivitis, including perennial and vernal allergic conjunctivitis; iritis; anterior and posterior uveitis; choroiditis; autoimmune; degenerative or inflammatory disorders affecting the retina; ophthalmitis including sympathetic ophthalmitis; sarcoidosis; infections including viral, fungal, and bacterial;

6. gastrointestinal tract: glossitis, gingivitis, periodontitis; oesophagitis, including reflux; eosinophilic gastro-enteritis, mastocytosis, Crohn's disease, colitis including ulcerative colitis, proctitis, pruritis ani; coeliac disease, irritable bowel syndrome, and food-related allergies which may have effects remote from the gut (for example migraine, rhinitis or eczema);

7. abdominal: hepatitis, including autoimmune, alcoholic and viral; fibrosis and cirrhosis of the liver; cholecystitis; pancreatitis, both acute and chronic;

8. genitourinary: nephritis including interstitial and glomerulonephritis; nephrotic syndrome; cystitis including acute and chronic (interstitial) cystitis and Hunner's ulcer; acute and chronic urethritis, prostatitis, epididymitis, oophoritis and salpingitis; vulvo-vaginitis; Peyronie's disease; erectile dysfunction (both male and female);

9. allograft rejection: acute and chronic following, for example, transplantation of kidney, heart, liver, lung, bone marrow, skin or cornea or following blood transfusion; or chronic graft versus host disease;

10. CNS: Alzheimer's disease and other dementing disorders including CJD and nvCJD; amyloidosis; multiple sclerosis and other demyelinating syndromes; cerebral atherosclerosis and vasculitis; temporal arteritis; myasthenia gravis; acute and chronic pain (acute, intermittent or persistent, whether of central or peripheral origin) including visceral pain, headache, migraine, trigeminal neuralgia, atypical facial pain, joint and bone pain, pain arising from cancer and tumor invasion, neuropathic pain syndromes including diabetic, post-herpetic, and HIV-associated neuropathies; neurosarcoidosis; central and peripheral nervous system complications of malignant, infectious or autoimmune processes;

11. other auto-immune and allergic disorders including Hashimoto's thyroiditis, Graves' disease, Addison's disease, diabetes mellitus, idiopathic thrombocytopaenic purpura, eosinophilic fasciitis, hyper-IgE syndrome, antiphospholipid syndrome;

12. other disorders with an inflammatory or immunological component; including acquired immune deficiency syndrome (AIDS), leprosy, Sezary syndrome, and paraneoplastic syndromes;

13. cardiovascular: atherosclerosis, affecting the coronary and peripheral circulation; pericarditis; myocarditis, inflammatory and auto-immune cardiomyopathies including myocardial sarcoid; ischaemic reperfusion injuries; endocarditis, valvulitis, and aortitis including infective (for example syphilitic); vasculitides; disorders of the proximal and peripheral veins including phlebitis and thrombosis, including deep vein thrombosis and complications of varicose veins;

14. oncology: treatment of common cancers including prostate, breast, lung, ovarian, pancreatic, bowel and colon, stomach, skin and brain tumors and malignancies affecting the bone marrow (including the leukaemias) and lymphoproliferative systems, such as Hodgkin's and non-Hodgkin's lymphoma; including the prevention and treatment of metastatic disease and tumour recurrences, and paraneoplastic syndromes; and, 15. gastrointestinal tract: Coeliac disease, proctitis, eosinopilic gastro-enteritis, mastocytosis, Crohn's disease, ulcerative colitis, microscopic colitis, indeterminant colitis, irritable bowel disorder, irritable bowel syndrome, non-inflammatory diarrhea, food-related allergies which have effects remote from the gut, e.g., migraine, rhinitis and eczema.

Accordingly, the present invention further provides a compound of formula (I), as hereinbefore defined for use in therapy.

In another aspect, the invention provides the use of a compound of formula (I), as hereinbefore defined, in the manufacture of a medicament for use in therapy.

In the context of the present specification, the term "therapy" also includes "prophylaxis" unless there are specific indications to the contrary. The terms "therapeutic" and "therapeutically" should be construed accordingly.

A further aspect of the invention provides a method of treating a disease state in a mammal suffering from, or at risk of, said disease, which comprises administering to a mammal in need of such treatment a therapeutically effective amount of a compound of formula (I) as hereinbefore defined.

The present invention also provides a compound of formula (I) as hereinbefore defined, for treating chronic obstructive pulmonary disease (COPD) (such as irreversible COPD).

The present invention also provides a compound of formula (I) as hereinbefore defined, for treating asthma.

The present invention also provides the use of a compound of formula (I) as hereinbefore defined, in the treatment of chronic obstructive pulmonary disease (COPD) (such as irreversible COPD).

The present invention also provides the use of a compound of formula (I) as hereinbefore defined, in the treatment of asthma.

The present invention also provides the use of a compound of formula (I) as hereinbefore defined, in the manufacture of a medicament for use in the treatment of chronic obstructive pulmonary disease (COPD) (such as irreversible COPD).

The present invention also provides the use of a compound of formula (I) as hereinbefore defined, in the manufacture of a medicament for use in the treatment of asthma.

The present invention further provides a method of treating chronic obstructive pulmonary disease (COPD) (such as irreversible COPD), in a warm-blooded animal, such as man, which comprises administering to a mammal in need of such treatment an effective amount of a compound of formula (I) as hereinbefore defined.

The present invention further provides a method of treating asthma in a warm-blooded animal, such as man, which comprises administering to a mammal in need of such treatment an effective amount of a compound of formula (I) as hereinbefore defined.

In order to use a compound of the invention for the therapeutic treatment of a warm-blooded animal, such as man, said ingredient is normally formulated in accordance with standard pharmaceutical practice as a pharmaceutical composition.

Therefore in another aspect the present invention provides a pharmaceutical composition that comprises a compound of the invention as hereinbefore defined and a pharmaceutically acceptable adjuvant, diluent or carrier. In a further aspect the present invention provides a process for the preparation of said composition, which comprises mixing active ingredient with a pharmaceutically acceptable adjuvant, diluent or carrier. Depending on the mode of administration, the pharmaceutical composition will, for example, comprise from 0.05 to 99% w (percent by weight), such as from 0.05 to 80% w, for example from 0.10 to 70% w, such as from 0.10 to 50% w, of active ingredient, all percentages by weight being based on total composition.

The pharmaceutical compositions of this invention may be administered in standard manner for the disease condition that it is desired to treat, for example by topical (such as to the lung and/or airways or to the skin), oral, rectal or parenteral administration. For these purposes the compounds of this invention may be formulated by means known in the art into the form of, for example, aerosols, dry powder formulations, tablets, capsules, syrups, powders, granules, aqueous or oily solutions or suspensions, (lipid) emulsions, dispersible powders, suppositories, ointments, creams, drops and sterile injectable aqueous or oily solutions or suspensions.

A suitable pharmaceutical composition of this invention is one suitable for oral administration in unit dosage form, for example a tablet or capsule, which contains between 0.1 mg and 1 g of active ingredient.

In another aspect a pharmaceutical composition of the invention is one suitable for intravenous, subcutaneous or intramuscular injection. Each patient may receive, for example, an intravenous, subcutaneous or intramuscular dose of 0.01 mgkg$^{-1}$ to 100 mgkg$^{-1}$ of the compound, for example in the range of 0.1 mgkg$^{-1}$ to 20 mgkg$^{-1}$ of this invention, the composition being administered 1 to 4 times per day. The intravenous, subcutaneous and intramuscular dose may be given by means of a bolus injection. Alternatively the intravenous dose may be given by continuous infusion over a period of time. Alternatively each patient will receive a daily oral dose, which is approximately equivalent to the daily parenteral dose, the composition being administered 1 to 4 times per day Another suitable pharmaceutical composition of this invention is one suitable for inhaled administration, inhalation being a particularly useful method for administering the compounds of the invention when treating respiratory diseases such as chronic obstructive pulmonary disease (COPD) or asthma. When administered by inhalation the compounds of formula (I) may be used effectively at doses in the µg range, for example 0.1 to 500 µg, 0.1 to 50 µg, 0.1 to 40 µg, 0.1 to 30 µg, 0.1 to 20 µg, 0.1 to 10 µg, 5 to 10 µg, 5 to 50 µg, 5 to 40 µg, 5 to 30 µg, 5 to 20 µg, 5 to 10 µg, 10 to 50 µg, 10 to 40 µg, 10 to 30 µg, or 10 to 20 µg of active ingredient.

In an embodiment of the invention, there is provided a pharmaceutical composition comprising a compound of the invention as hereinbefore defined, in association with a pharmaceutically acceptable adjuvant, diluent or carrier, which is formulated for inhaled administration.

When administered by inhalation, metered dose inhaler devices may be used to administer the active ingredient, dispersed in a suitable propellant and with or without additional excipients such as ethanol, surfactants, lubricants or stabilising agents. Suitable propellants include hydrocarbon, chlorofluorocarbon and hydrofluoroalkane (e.g. heptafluoroalkane) propellants, or mixtures of any such propellants. Preferred propellants are P134a and P227, each of which may be used alone or in combination with other propellants and/or surfactant and/or other excipients. Nebulised aqueous suspensions or, preferably, solutions may also be employed, with or without a suitable pH and/or tonicity adjustment, either as a unit-dose or multi-dose formulations.

Dry powder inhalers may be used to administer the active ingredient, alone or in combination with a pharmaceutically acceptable carrier, in the later case either as a finely divided powder or as an ordered mixture. The dry powder inhaler may be single dose or multi-dose and may utilise a dry powder or a powder-containing capsule.

Metered dose inhaler, nebuliser and dry powder inhaler devices are well known and a variety of such devices are available.

The invention further relates to combination therapies wherein a compound of the invention or a pharmaceutical composition or formulation comprising a compound of the invention, is administered concurrently or sequentially or as a combined preparation with another therapeutic agent or agents, for the treatment of one or more of the conditions listed.

In particular, for the treatment of the inflammatory diseases such as (but not restricted to) rheumatoid arthritis, osteoarthritis, asthma, allergic rhinitis, chronic obstructive pulmonary disease (COPD), psoriasis, and inflammatory bowel disease, the compounds of the invention may be combined with agents listed below.

Non-steroidal anti-inflammatory agents (hereinafter NSAIDs) including non-selective cyclo-oxygenase COX-1/COX-2 inhibitors whether applied topically or systemically (such as piroxicam, diclofenac, propionic acids such as naproxen, flurbiprofen, fenoprofen, ketoprofen and ibuprofen, fenamates such as mefenamic acid, indomethacin, sulindac, azapropazone, pyrazolones such as phenylbutazone, salicylates such as aspirin); selective COX-2 inhibitors (such as meloxicam, celecoxib, rofecoxib, valdecoxib, lumarocoxib, parecoxib and etoricoxib); cyclo-oxygenase inhibiting nitric oxide donors (CINODs); glucocorticosteroids (whether administered by topical, oral, intramuscular, intravenous, or intra-articular routes); methotrexate; leflunomide; hydroxychloroquine; d-penicillamine; auranofin or other parenteral or oral gold preparations; analgesics; diacerein; intra-articular therapies such as hyaluronic acid derivatives; and nutritional supplements such as glucosamine.

The present invention still further relates to the combination of a compound of the is invention together with a cytokine or agonist or antagonist of cytokine function, (including agents which act on cytokine signalling pathways such as modulators of the SOCS system) including alpha-, beta-, and gamma-interferons; insulin-like growth factor type I (IGF-1); interleukins (IL) including IL1 to 17, and interleukin antagonists or inhibitors such as anakinra; tumour necrosis factor alpha (TNF-α) inhibitors such as anti-TNF monoclonal antibodies (for example infliximab; adalimumab, and CDP-870) and TNF receptor antagonists including immunoglobulin molecules (such as etanercept) and low-molecular-weight agents such as pentoxyfylline.

In addition the invention relates to a combination of a compound of the invention with a monoclonal antibody targeting B-Lymphocytes (such as CD20 (rituximab), MRA-aIL16R and T-Lymphocytes, CTLA4-Ig, HuMax Il-15).

The present invention still further relates to the combination of a compound of the invention with a modulator of chemokine receptor function such as an antagonist of CCR1, CCR2, CCR2A, CCR2B, CCR3, CCR4, CCR5, CCR6, CCR7, CCR8, CCR9, CCR10 and CCR11 (for the C—C family); CXCR1, CXCR2, CXCR3, CXCR4 and CXCR5 (for the C—X—C family) and $CX_3CR1$ for the C—$X_3$—C family.

The present invention further relates to the combination of a compound of the invention with an inhibitor of matrix metalloprotease (MMPs), i.e., the stromelysins, the collagenases, and the gelatinases, as well as aggrecanase; especially collagenase-1 (MMP-1), collagenase-2 (MMP-8), collagenase-3 (MMP-13), stromelysin-1 (MMP-3), stromelysin-2 (MMP-10), and stromelysin-3 (MMP-11) and MMP-9 and MMP-12, including agents such as doxycycline.

The present invention still further relates to the combination of a compound of the invention and a leukotriene biosynthesis inhibitor, 5-lipoxygenase (5-LO) inhibitor or 5-lipoxygenase activating protein (FLAP) antagonist such as; zileuton; ABT-761; fenleuton; tepoxalin; Abbott-79175; Abbott-85761; a N-(5-substituted)-thiophene-2-alkylsulfonamide; 2,6-di-tert-butylphenolhydrazones; a methoxytetrahydropyrans such as Zeneca ZD-2138; the compound SB-210661; a pyridinyl-substituted 2-cyanonaphthalene compound such as L-739,010; a 2-cyanoquinoline compound such as L-746,530; or an indole or quinoline compound such as MK-591, MK-886, and BAY x 1005.

The present invention further relates to the combination of a compound of the invention and a receptor antagonist for leukotrienes (LT) B4, LTC4, LTD4, and LTE4 selected from the group consisting of the phenothiazin-3-1s such as L-651,392; amidino compounds such as CGS-25019c; benzoxalamines such as ontazolast; benzenecarboximidamides such as BIIL 284/260; and compounds such as zafirlukast, ablukast, montelukast, pranlukast, verlulkast (MK-679), RG-12525, Ro-245913, iralukast (CGP 45715A), and BAY x 7195.

The present invention still further relates to the combination of a compound of the invention and a phosphodiesterase (PDE) inhibitor such as a methylxanthanine including theophylline and aminophylline; a selective PDE isoenzyme inhibitor including a PDE4 inhibitor an inhibitor of the isoform PDE4D, or an inhibitor of PDE5.

The present invention further relates to the combination of a compound of the invention and a histamine type 1 receptor antagonist such as cetirizine, loratadine, desloratadine, fexofenadine, acrivastine, terfenadine, astemizole, azelastine, levocabastine, chlorpheniramine, promethazine, cyclizine, or mizolastine; applied orally, topically or parenterally.

The present invention still further relates to the combination of a compound of the invention and a proton pump inhibitor (such as omeprazole) or a gastroprotective histamine type 2 receptor antagonist.

The present invention further relates to the combination of a compound of the invention and an antagonist of the histamine type 4 receptor.

The present invention still further relates to the combination of a compound of the invention and an alpha-1/alpha-2 adrenoceptor agonist vasoconstrictor sympathomimetic agent, such as propylhexedrine, phenylephrine, phenylpropanolamine, ephedrine, pseudoephedrine, naphazoline hydrochloride, oxymetazoline hydrochloride, tetrahydrozoline hydrochloride, xylometazoline hydrochloride, tramazoline hydrochloride or ethylnorepinephrine hydrochloride.

The present invention still further relates to the combination of a compound of the invention and a beta-adrenoceptor agonist (including beta receptor subtypes 1-4) such as isoprenaline, salbutamol, formoterol, salmeterol, terbutaline, orciprenaline, bitolterol mesylate, pirbuterol, or indacaterol or a chiral enantiomer thereof.

The present invention further relates to the combination of a compound of the invention and a chromone, such as sodium cromoglycate or nedocromil sodium.

The present invention still further relates to the combination of a compound of the invention with a glucocorticoid, such as flunisolide, triamcinolone acetonide, beclomethasone dipropionate, budesonide, fluticasone propionate, ciclesonide or mometasone furoate.

The present invention further relates to the combination of a compound of the invention with an agent that modulates a nuclear hormone receptor such as PPARs.

The present invention still further relates to the combination of a compound of the invention together with an immunoglobulin (Ig) or Ig preparation or an antagonist or antibody modulating Ig function such as anti-IgE (for example omalizumab).

The present invention further relates to the combination of a compound of the invention and another systemic or topically-applied anti-inflammatory agent, such as thalidomide or a derivative thereof, a retinoid, dithranol or calcipotriol.

The present invention still further relates to the combination of a compound of the invention and combinations of aminosalicylates and sulfapyridine such as sulfasalazine, mesalazine, balsalazide, and olsalazine; and immunomodulatory agents such as the thiopurines, and corticosteroids such as budesonide.

The present invention further relates to the combination of a compound of the invention together with an antibacterial agent such as a penicillin derivative, a tetracycline, a macrolide, a beta-lactam, a fluoroquinolone, metronidazole, an inhaled aminoglycoside; an antiviral agent including acyclovir, famciclovir, valaciclovir, ganciclovir, cidofovir, amantadine, rimantadine, ribavirin, zanamavir and oseltamavir; a protease inhibitor such as indinavir, nelfinavir, ritonavir, and saquinavir; a nucleoside reverse transcriptase inhibitor such as didanosine, lamivudine, stavudine, zalcitabine or zidovudine; or a non-nucleoside reverse transcriptase inhibitor such as nevirapine or efavirenz.

The present invention still further relates to the combination of a compound of the invention and a cardiovascular agent such as a calcium channel blocker, a beta-adrenoceptor blocker, an angiotensin-converting enzyme (ACE) inhibitor, an angiotensin-2 receptor antagonist; a lipid lowering agent such as a statin or a fibrate; a modulator of blood cell morphology such as pentoxyfylline; thrombolytic, or an anticoagulant such as a platelet aggregation inhibitor.

The present invention further relates to the combination of a compound of the invention and a CNS agent such as an antidepressant (such as sertraline), an anti-Parkinsonian drug (such as deprenyl, L-dopa, ropinirole, pramipexole, a MAOB inhibitor such as selegine and rasagiline, a comP inhibitor such as tasmar, an A-2 inhibitor, a dopamine reuptake inhibitor, an NMDA antagonist, a nicotine agonist, a dopamine agonist or an inhibitor of neuronal nitric oxide synthase), or an anti-Alzheimer's drug such as donepezil, rivastigmine, tacrine, a COX-2 inhibitor, propentofylline or metrifonate.

The present invention still further relates to the combination of a compound of the invention and an agent for the treatment of acute or chronic pain, such as a centrally or peripherally-acting analgesic (for example an opioid or derivative thereof), carbamazepine, phenytoin, sodium valproate, amitryptiline or other anti-depressant agent-s, paracetamol, or a non-steroidal anti-inflammatory agent.

The present invention further relates to the combination of a compound of the invention together with a parenterally or topically-applied (including inhaled) local anaesthetic agent such as lignocaine or a derivative thereof.

A compound of the present invention can also be used in combination with an anti-osteoporosis agent including a hormonal agent such as raloxifene, or a biphosphonate such as alendronate.

The present invention still further relates to the combination of a compound of the invention together with a: (i) tryptase inhibitor; (ii) platelet activating factor (PAF) antagonist; (iii) interleukin converting enzyme (ICE) inhibitor; (iv) IMPDH inhibitor; (v) adhesion molecule inhibitors including VLA-4 antagonist; (vi) cathepsin; (vii) kinase inhibitor such as an inhibitor of tyrosine kinase (such as Btk, Itk, Jak3 or MAP, for example Gefitinib or Imatinib mesylate), a serine/threonine kinase (such as an inhibitor of a MAP kinase such as p38, JNK, protein kinase A, B or C, or IKK), or a kinase involved in cell cycle regulation (such as a cylin dependent kinase); (viii) glucose-6 phosphate dehydrogenase inhibitor; (ix) kinin-B1.- or B2.-receptor antagonist; (x) anti-gout agent, for example colchicine; (xi) xanthine oxidase inhibitor, for example allopurinol; (xii) uricosuric agent, for example probenecid, sulfinpyrazone or benzbromarone; (xiii) growth hormone secretagogue; (xiv) transforming growth factor (TGFβ); (xv) platelet-derived growth factor (PDGF); (xvi) fibroblast growth factor for example basic fibroblast growth factor (bFGF); (xvii) granulocyte macrophage colony stimulating factor (GM-CSF); (xviii) capsaicin cream; (xix) tachykinin NK1 or NK3 receptor antagonist such as NKP-608C, SB-233412 (talnetant) or D-4418; (xx) elastase inhibitor such as UT-77 or ZD-0892; (xxi) TNF-alpha converting enzyme inhibitor (TACE); (xxii) induced nitric oxide synthase (iNOS) inhibitor; (xxiii) chemoattractant receptor-homologous molecule expressed on TH2 cells, (such as a CRTH2 antagonist); (xxiv) inhibitor of P38; (xxv) agent modulating the function of Toll-like receptors (TLR), (xxvi) agent modulating the activity of purinergic receptors such as P2X7; or (xxvii) inhibitor of transcription factor activation such as NFkB, API, or STATS.

A compound of the invention can also be used in combination with an existing therapeutic agent for the treatment of cancer, for example suitable agents include:

(i) an antiproliferative/antineoplastic drug or a combination thereof, as used in medical oncology, such as an alkylating agent (for example cis-platin, carboplatin, cyclophosphamide, nitrogen mustard, melphalan, chlorambucil, busulphan or a nitrosourea); an antimetabolite (for example an antifolate such as a fluoropyrimidine like 5-fluorouracil or tegafur, raltitrexed, methotrexate, cytosine arabinoside, hydroxyurea, gemcitabine or paclitaxel); an antitumour antibiotic (for example an anthracycline such as adriamycin, bleomycin, doxorubicin, daunomycin, epirubicin, idarubicin, mitomycin-C, dactinomycin or mithramycin); an antimitotic agent (for example a vinca alkaloid such as vincristine, vinblastine, vindesine or vinorelbine, or a taxoid such as taxol or taxotere); or a topoisomerase inhibitor (for example an epipodophyllotoxin such as etoposide, teniposide, amsacrine, topotecan or a camptothecin);

(ii) a cytostatic agent such as an antioestrogen (for example tamoxifen, toremifene, raloxifene, droloxifene or iodoxyfene), an oestrogen receptor down regulator (for example fulvestrant), an antiandrogen (for example bicalutamide, flutamide, nilutamide or cyproterone acetate), a LHRH antagonist or LHRH agonist (for example goserelin, leuprorelin or buserelin), a progestogen (for example megestrol acetate), an aromatase inhibitor (for example as anastrozole, letrozole, vorazole or exemestane) or an inhibitor of 5α-reductase such as finasteride;

(iii) an agent which inhibits cancer cell invasion (for example a metalloproteinase inhibitor like marimastat or an inhibitor of urokinase plasminogen activator receptor function);

(iv) an inhibitor of growth factor function, for example: a growth factor antibody (for example the anti-erbb2 antibody trastuzumab, or the anti-erbb1 antibody cetuximab [C225]), a farnesyl transferase inhibitor, a tyrosine kinase inhibitor or a serine/threonine kinase inhibitor, an inhibitor of the epidermal growth factor family (for example an EGFR family tyrosine kinase inhibitor such as N-(3-chloro-4-fluorophenyl)-7-methoxy-6-(3-morpholinopropoxy)quinazolin-4-amine (gefitinib, AZD1839), N-(3-ethynylphenyl)-6,7-bis(2-methoxyethoxy) quinazolin- 4-amine (erlotinib, OSI-774) or 6-acrylamido-N-(3-chloro-4-fluorophenyl)-7-(3-morpholinopropoxy) quinazolin-4-amine (CI 1033)), an inhibitor of the platelet-derived growth factor family, or an inhibitor of the hepatocyte growth factor family;

(v) an antiangiogenic agent such as one which inhibits the effects of vascular endothelial growth factor (for example the anti-vascular endothelial cell growth factor antibody bevacizumab, a compound disclosed in WO 97/22596, WO 97/30035, WO 97/32856 or WO 98/13354), or a compound that works by another mechanism (for example linomide, an inhibitor of integrin αvβ3 function or an angiostatin);

(vi) a vascular damaging agent such as combretastatin A4, or a compound disclosed in WO 99/02166, WO 00/40529, WO 00/41669, WO 01/92224, WO 02/04434 or WO 02/08213;

(vii) an agent used in antisense therapy, for example one directed to one of the targets listed above, such as ISIS 2503, an anti-ras antisense;

(viii) an agent used in a gene therapy approach, for example approaches to replace aberrant genes such as aberrant p53 or aberrant BRCA1 or BRCA2, GDEPT (gene-directed enzyme pro-drug therapy) approaches such as those using cytosine deaminase, thymidine kinase or a bacterial nitroreductase enzyme and approaches to increase patient tolerance to chemotherapy or radiotherapy such as multi-drug resistance gene therapy; or (ix) an agent used in an immunotherapeutic approach, for example ex-vivo and in-vivo approaches to increase the immunogenicity of patient tumour cells, such as transfection with cytokines such as interleukin 2, interleukin 4 or granulocyte-macrophage colony stimulating factor, approaches to decrease T-cell anergy, approaches using transfected immune cells such as cytokine-transfected dendritic cells, approaches using cytokine-transfected tumour cell lines and approaches using anti-idiotypic antibodies.

In a further embodiment the present invention provides a pharmaceutical product comprising, in combination, a first active ingredient which is a compound of formula (I) as hereinbefore described, and at least one further active ingredient selected from:— a phosphodiesterase inhibitor,
a β2. adrenoceptor agonist,
a modulator of chemokine receptor function,
an inhibitor of kinase function,
a protease inhibitor,
a steroidal glucocorticoid receptor agonist, and a
a non-steroidal glucocorticoid receptor agonist.

The pharmaceutical product according to this embodiment may, for example, be a pharmaceutical composition comprising the first and further active ingredients in admixture. Alternatively, the pharmaceutical product may, for example, comprise the first and further active ingredients in separate pharmaceutical preparations suitable for simultaneous, sequential or separate administration to a patient in need thereof.

The pharmaceutical product of this embodiment is of particular use in treating respiratory diseases such as asthma, COPD or rhinitis.

Examples of a phosphodiesterase inhibitor that may be used in the pharmaceutical product according to this embodiment include a PDE4 inhibitor such as an inhibitor of the isoform PDE4D, a PDE3 inhibitor and a PDE5 inhibitor. Examples include the compounds
(Z)-3-(3,5-dichloro-4-pyridyl)-2-[4-(2-indanyloxy-5-methoxy-2-pyridyl]propenenitrile, N-[9-amino-4-oxo-1-phenyl-3,4,6,7-tetrahydropyrrolo[3,2,1-jk][1,4]benzodiazepin-3(R)— yl]pyridine-3-carboxamide (CI-1044)

3-(benzyloxy)-1-(4-fluorobenzyl)-N-[3-(methylsulphonyl) phenyl]-1H-indole-2-carboxamide, (1S-exo)-5-[3-(bicyclo[2.2.1]hept-2-yloxy)-4-methoxyphenyl]tetrahydro-2(1H)-pyrimidinone (Atizoram), N-(3,5-dichloro-4-pyridinyl)-2-[1-(4-fluorobenzyl)-5-hydroxy-1H-indol-3-yl]-2-oxoacetamide (AWL-12-281), β-[3-(cyclopentyloxy)-4-methoxyphenyl]-1,3-dihydro-1,3-dioxo-2H-isoindole-2-propanamide (CDC-801), N-[9-methyl-4-oxo-1-phenyl-3,4,6,7-tetrahydropyrrolo[3,2,1-jk][1,4]benzodiazepin-3 (R)-yl]pyridine-4-carboxamide (CI-1018), cis-[4-cyano-4-(3-cyclopentyloxy-4-methoxyphenyl)cyclohexane-1-carboxylic acid (Cilomilast)

8-amino-1,3-bis(cyclopropylmethyl)xanthine (Cipamfylline)

N-(2,5-dichloro-3-pyridinyl)-8-methoxy-5-quinolinecarboxamide (D-4418), 5-(3,5-di-tert-butyl-4-hydroxybenzylidene)-2-iminothiazolidin-4-one (Darbufelone), 2-methyl-1-[2-(1-methylethyl)pyrazolo[1,5-a]pyridin-3-yl]-1-propanone (Ibudilast), 2-(2,4-dichlorophenylcarbonyl)-3-ureidobenzofuran-6-yl methanesulphonate (Lirimilast), (−)-(R)-5-(4-methoxy-3-propoxyphenyl)-5-methyloxazolidin-2-one (Mesopram), (−)-cis-9-ethoxy-8-methoxy-2-methyl-1,2,3,4,4a,10b-hexahydro-6-(4-diisopropylaminocarbonylphenyl)-benzo[c][1,6]naphthyridine (Pumafentrine), 3-(cyclopropylmethoxy)-N-(3,5-dichloro-4-pyridyl)-4-(difluoromethoxy)benzamide (Roflumilast), the N-oxide of Roflumilast, 5,6-diethoxybenzo[b]thiophene-2-carboxylic acid (Tibenelast)

2,3,6,7-tetrahydro-2-(mesitylimino)-9,10-dimethoxy-3-methyl-4H-pyrimido[6,1-a]isoquinolin-4-one (trequinsin) and 3-[[3-(cyclopentyloxy)-4-methoxyphenyl]-methyl]-N-ethyl-8-(1-methylethyl)-3H-purine-6-amine (V-11294A).

Examples of a β₂-adrenoceptor agonist that may be used in the pharmaceutical product according to this embodiment include metaproterenol, isoproterenol, isoprenaline, albuterol, salbutamol (e.g. as sulphate), formoterol (e.g. as fumarate), salmeterol (e.g. as xinafoate), terbutaline, orciprenaline, bitolterol (e.g. as mesylate), pirbuterol or indacaterol. The β₂-adrenoceptor agonist of this embodiment may be a long-acting β₂-agonists, for example salmeterol (e.g. as xinafoate), formoterol (e.g. as fumarate), bambuterol (e.g. as hydrochloride), carmoterol (TA 2005, chemically identified as 2(1H)-Quinolone, 8-hydroxy-5-[1-hydroxy-2-[[2-(4-methoxy-phenyl)-1-methylethyl]-amino]ethyl]-monohydrochloride, [R-(R*,R*)] also identified by Chemical Abstract Service Registry Number 137888-11-0 and disclosed in U.S. Pat. No. 4,579,854), indacaterol (CAS no 312753-06-3; QAB-149), formanilide derivatives e.g. 3-(4-{[6-({(2R)-2-[3-(formylamino)-4-hydroxyphenyl]-2-hydroxyethyl}amino)hexyl]oxy}-butyl)-benzenesulfonamide as disclosed in WO 2002/76933, benzenesulfonamide derivatives e.g. 3-(4-{[6-({(2R)-2-hydroxy-2-[4-hydroxy-3-(hydroxy-methyl)phenyl]ethyl}amino)-hexyl]oxy}butyl) benzenesulfonamide as disclosed in WO 2002/88167, aryl aniline receptor agonists as disclosed in WO 2003/042164 and WO 2005/025555, indole derivatives as disclosed in WO 2004/032921 and US 2005/222144, and compounds GSK 159797, GSK 159802, GSK 597901, GSK 642444 and GSK 678007.

Examples of a modulator of chemokine receptor function that may be used in the pharmaceutical product according to this embodiment include a CCR1 receptor antagonist.

Examples of an inhibitor of kinase function that may be used in the pharmaceutical product according to this embodiment include a p38 kinase inhibitor and an IKK inhibitor.

Examples of a protease inhibitor that may be used in the pharmaceutical product according to this embodiment include an inhibitor of neutrophil elastase or an inhibitor of MMP12.

Examples of a steroidal glucocorticoid receptor agonist that may be used in the pharmaceutical product according to this embodiment include budesonide, fluticasone (e.g. as propionate ester), mometasone (e.g. as furoate ester), beclomethasone (e.g. as 17-propionate or 17,21-dipropionate esters), ciclesonide, loteprednol (as e.g. etabonate), etiprednol (as e.g. dicloacetate), triamcinolone (e.g. as acetonide), flunisolide, zoticasone, flumoxonide, rofleponide, butixocort (e.g. as propionate ester), prednisolone, prednisone, tipredane, steroid esters e.g. 6α,9α-difluoro-17α-[(2-furanylcarbonyl)oxy]-11β-hydroxy-16α-methyl-3-oxo-androsta-1,4-diene-17β-carbothioic acid S-fluoromethyl ester, 6α,9α-difluoro-11β-hydroxy-16α-methyl-3-oxo-17α-propionyloxy-androsta-1,4-diene-17β-carbothioic acid S-(2-oxo-tetrahydro-furan-3 S-yl) ester and 6α,9α-difluoro-11β-hydroxy-16α-methyl-17α-[(4-methyl-1,3-thiazole-5-carbonyl)oxy]-3-oxo-androsta-1,4-diene-17β-carbothioic acid S-fluoromethyl ester, steroid esters according to DE 4129535, steroids according to WO 2002/00679, WO 2005/041980, or steroids GSK 870086, GSK 685698 and GSK 799943.

Examples of a modulator of a non-steroidal glucocorticoid receptor agonist that may be used in the pharmaceutical product according to this embodiment include those described in WO2006/046916.

The present invention will now be illustrated with the following non-limiting Examples.

In the examples the NMR spectra were measured on a Varian Unity Inova spectrometer at a proton frequency of either 300 or 400 MHz. The MS spectra were measured on either an Agilent 1100 MSD G1946D spectrometer or a Hewlett Packard HP1100 MSD G1946A spectrometer. Preparative HPLC separations were performed using a Waters Symmetry® or Xterra® column using 0.1% aqueous trifluoroacetic acid: acetonitrile, 0.1% aqueous ammonia: acetonitrile or 0.1% ammonium acetate: acetonitrile as the eluent. SCX and NH$_2$ resin were obtained from Varian Incorporated. IUPAC names were generated using the ACDLabs Name Computer Program.

EXAMPLE 1

(3R)-3-{[(1-Phenylcycloheptyl)carbonyl]oxy}-1-azabicyclo[2.2.2]octane a) 1-Phenylcycloheptanol

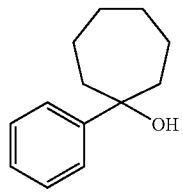

To magnesium (1.2 g) in anhydrous tetrahydrofuran (60 mL) under an environment of nitrogen was added a crystal of iodine followed by bromobenzene (7.85 g) at such a rate that the reaction maintained a steady reflux. The reaction mixture was stirred for 20 minutes then cycloheptanone (4.48 g) was added with care. After stirring for 10 minutes saturated aqueous ammonium chloride (10 mL) was added and the reaction was partitioned between water (100 mL) and isohexane (100 mL). The organic layer was dried (MgSO$_4$) and evaporated to afford the sub-titled compound (7.6 g) as an oil.

$^1$H NMR (299.946 MHz, CDCl$_3$) δ 7.53-7.47 (m, 2H), 7.36-7.29 (m, 2H), 7.26-7.19 (m, 1H), 2.07 (ddd, 2H), 1.97-1.50 (m, 1H).

b) 1-Methoxy-1-phenylcycloheptane

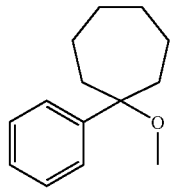

1-Phenylcycloheptanol (Example 1a) (7.6 g) was dissolved in tetrahydrofuran (100 mL) and sodium hydride (60% in oil, 2.0 g) added. The reaction was stirred at 60° C. for 5 minutes and iodomethane (7.1 g) added. The mixture was maintained at 60° C. overnight and then further quantities of sodium hydride (60% in oil, 2.0 g) and iodomethane (7.1 g) were added and the reaction was refluxed for 70 hours. The reaction mixture was partitioned between water (100 mL) and isohexane (100 mL) and the organic layer separated, dried (MgSO$_4$) and evaporated to afford the sub-titled compound (11.31 g).

$^1$H NMR (299.946 MHz, CDCl$_3$) δ 7.43-7.37 (m, 2H), 7.37-7.30 (m, 2H), 7.24-7.19 (m, 1H), 2.98 (s, 3H), 2.12-1.88 (m, 4H), 1.88-1.45 (m, 8H).

c) 1-Phenylcycloheptanecarboxylic Acid

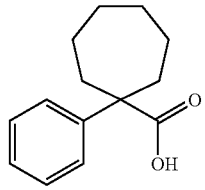

Potassium (2.62 g) and sodium (0.52 g) were heated together at 120° C. in mineral oil under an environment of nitrogen for 30 minutes and then cooled to room temperature. The oil was removed and replaced with ether (100 mL) and 1-methoxy-1-phenylcycloheptane (Example 1b) (4.9 g) was added and the reaction was stirred under nitrogen overnight at room temperature. The reaction was cooled to −78° C. and solid carbon dioxide (~20 g) was added with stirring. The reaction was allowed to warm to room temperature and water (150 mL) was added carefully under a environment of nitrogen. The aqueous layer was separated, neutralised with concentrated hydrochloric acid and extracted with diethyl ether (150 mL). The organic layer was dried (MgSO$_4$) and evaporated afford to the sub-titled compound (4.15 g) as an oil.

$^1$H NMR (299.946 MHz, CDCl$_3$) δ 7.40-7.20 (m, 5H), 2.49-2.35 (m, 2H), 2.16-2.03 (m, 2H), 1.76-1.47 (m, 8H).

d) Methyl 1-phenylcycloheptanecarboxylate

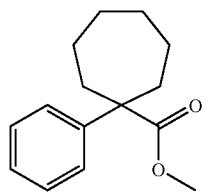

1-Phenylcycloheptanecarboxylic acid (Example 1c) (4.15 g) was refluxed in methanol (150 mL) and concentrated hydrochloric acid (5 mL) for 24 hours. The solvent was evaporated and the residue was dissolved in ether (100 mL) which was washed with water (100 mL), saturated sodium bicarbonate (50 mL) and water (100 mL), dried (MgSO$_4$) and evaporated to afford the sub-titled compound (3.5 g) as an oil.

$^1$H NMR (299.946 MHz, CDCl$_3$) δ 7.37-7.18 (m, 5H), 3.63 (s, 3H), 2.47-2.35 (m, 2H), 2.08-1.97 (m, 2H), 1.70-1.48 (m, 8H).

EXAMPLE 1

(3R)-3-{[(1-Phenylcycloheptyl)carbonyl]oxy}-1-azabicyclo[2.2.2]octane

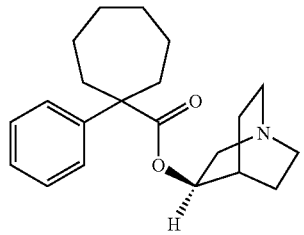

Methyl 1-phenylcycloheptanecarboxylate (Example 1d) (1.0 g) and (R)-quinuclidin-3-ol (commercially available from Acros Organics)[1], (0.39 g) were refluxed in heptane (50 mL) containing sodium (~5 mg) in a Dean and Stark apparatus for 24 hours. Heptane (20 mL) was replaced with toluene (20 mL) and the reflux was continued for 3 days. The reaction was partitioned between water (50 mL) and ether (50 mL) and the ether layer was separated, dried (MgSO$_4$) and evaporated. The crude product was purified by column chromatography on silica eluting with ethyl acetate/triethylamine (99/1) to afford the titled compound (0.83 g) as an oil.[1] The amount of minor (S) isomer present in the (R)— quinuclidin-3-ol was estimated using chiral HPLC to be less than 0.5%.

m/e 328 [M+H]$^+$ $^1$H NMR (299.946 MHz, CDCl$_3$) δ 7.35-7.27 (m, 4H), 7.23-7.16 (m, 1H), 4.78-4.71 (m, 1H), 3.12 (ddd, 1H), 2.79-2.32 (m, 7H), 2.16-1.98 (m, 2H), 1.91-1.80 (m, 1H), 1.70-1.34 (m, 12H).

EXAMPLE 2

(3R)-1-Methyl-3-{[(1-phenylcycloheptyl)carbonyl]oxy}-1-azoniabicyclo[2.2.2]octane Iodide

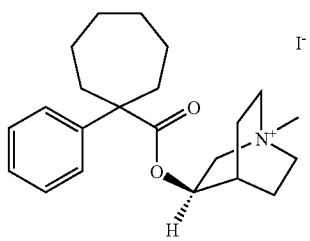

To (3R)-3-{[(1-phenylcycloheptyl)carbonyl]oxy}-1-azabicyclo[2.2.2]octane (Example 1) (0.78 g) in acetonitrile (30 mL) was added iodomethane (0.8 mL). After standing overnight, the solvent was removed and the residue was dried under high vacuum then triturated with ether to afford the titled compound (847 mg).

m/e 342 [M]$^+$ $^1$H NMR (299.947 MHz, DMSO-D$_6$) δ 7.39-7.29 (m, 4H), 7.28-7.21 (m, 1H), 5.07-4.99 (m, 1H), 3.83 (ddd, 1H), 3.44-3.19 (m, 4H), 3.19-3.04 (m, 1H), 2.94 (s, 3H), 2.46-2.24 (m, 2H), 2.23-2.08 (m, 2H), 2.03-1.76 (m, 3H), 1.75-1.41 (m, 10H).

EXAMPLE 3

(3R)-1-(3-Phenoxypropyl)-3-{[(1-phenylcycloheptyl)carbonyl]oxy}-1-azoniabicyclo[2.2.2]octane Bromide

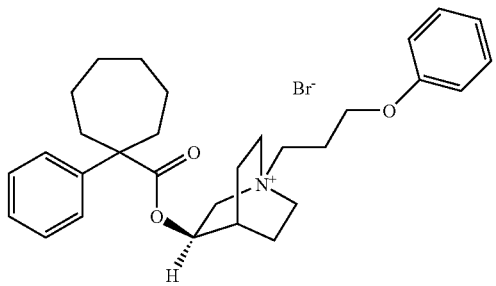

To (3R)-3-{[(1-phenylcycloheptyl)carbonyl]oxy}-1-azabicyclo[2.2.2]octane (Example 1) (0.15 g) in acetonitrile (2 mL) was added 3-phenoxypropyl bromide (0.197 g). The reaction was stirred at 80° C. for 36 hours and the acetonitrile was removed. The solid was triturated twice with ethyl acetate/iso-hexane filtered and dried to afford the titled compound (140 mg).

m/e 462 [M]$^+$ $^1$H NMR (299.947 MHz, DMSO-D$_6$) δ 7.45-7.19 (m, 7H), 7.03-6.90 (m, 3H), 5.07 (s, 1H), 4.02 (t, 2H), 3.96-3.82 (m,

1H), 3.54-3.27 (m, 3H), 3.19 (d, 1H), 3.12-2.92 (m, 1H), 2.45-2.25 (m, 4H), 2.24-1.79 (m, 7H), 1.78-1.41 (m, 10H).

EXAMPLE 4

(3R)-1-[2-(Isoxazol-3-ylamino)-2-oxoethyl]-3-{[(1-phenylcycloheptyl)carbonyl]oxy}-1-azoniabicyclo[2.2.2]octane Bromide a) 2-Bromo-N-isoxazol-3-yl-acetamide

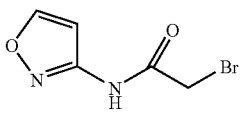

3-Aminoisoxazole (1.14 g) was dissolved in dichloromethane (50 mL) and potassium carbonate (3.74 g) was added. Bromoacetyl chloride (1.12 mL) was added slowly with stirring and the suspension was stirred overnight. The reaction was washed with water (2×50 mL), dried and evaporated. The product was recrystallised from dichloromethane/isohexane to afford the sub-titled compound (2.3 g).

$^1$H NMR (299.946 MHz, CDCl$_3$) δ 8.94 (s, 1H), 8.34 (s, 1H), 7.06 (s, 1H), 4.03 (s, 2H).

(3R)-1-[2-(Isoxazol-3-ylamino)-2-oxoethyl]-3-{[(1-phenylcycloheptyl)carbonyl]oxy}-1-azoniabicyclo[2.2.2]octane Bromide

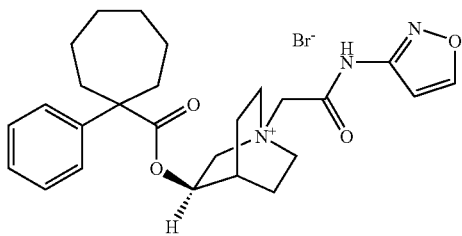

To (3R)-3-{[(1-phenylcycloheptyl)carbonyl]oxy}-1-azabicyclo[2.2.2]octane (Example 1) (0.12 g) in acetonitrile (3 mL) was added 2-bromo-N-isoxazol-3-yl-acetamide (Example 4a) (75 mg). The reaction was stirred at room temperature overnight and the acetonitrile was removed under reduced pressure. The solid was recrystallised twice with ethyl acetate, filtered and dried to afford the titled compound (140 mg).

m/e 452 [M]$^+$ $^1$H NMR (299.947 MHz, DMSO-D$_6$) δ 11.76 (s, 1H), 8.90 (dd, 1H), 7.44-7.21 (m, 5H), 6.90 (s, 1H), 5.12 (t, 1H), 4.42 (s, 2H), 4.17-4.05 (m, 1H), 3.73-3.50 (m, 4H), 3.47-3.21 (m, 1H), 2.44-2.26 (m, 2H), 2.26-2.07 (m, 2H), 2.07-1.85 (m, 2H), 1.83-1.69 (m, 1H), 1.68-1.41 (m, 10H).

EXAMPLE 5

(3R)-1-(4-Fluorobenzyl)-3-{[(1-phenylcycloheptyl)carbonyl]oxy}-1-azoniabicyclo[2.2.2]octane Bromide

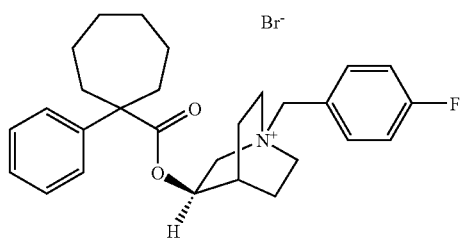

To (3R)-3-{[(1-phenylcycloheptyl)carbonyl]oxy}-1-azabicyclo[2.2.2]octane (Example 1) (0.1 g) in acetonitrile (5 mL) was added 4-fluorobenzyl bromide (0.15 mL). The reaction was stirred at room temperature overnight and the acetonitrile was removed under reduced pressure. The solid was recrystallised with ethyl acetate/isohexane, filtered, washed with ethyl acetate/isohexane and dried to afford the titled compound (120 mg).

m/e 436 [M]$^+$ $^1$H NMR (299.947 MHz, DMSO-D$_6$) δ 7.55 (dd, 2H), 7.42-7.18 (m, 7H), 5.11-5.00 (m, 1H), 4.51 (d, 1H), 4.45 (d, 1H), 3.87-3.73 (m, 1H), 3.47-3.21 (m, 3H), 3.20-3.08 (m, 1H), 3.08-2.90 (m, 1H), 2.42-2.19 (m, 2H), 2.18-2.03 (m, 2H), 2.01-1.76 (m, 2H), 1.75-1.61 (m, 1H), 1.61-1.39 (m, 10H).

EXAMPLE 6

(3R)-1-Benzyl-3-{[(1-phenylcycloheptyl)carbonyl]oxy}-1-azoniabicyclo[2.2.2]octane Bromide

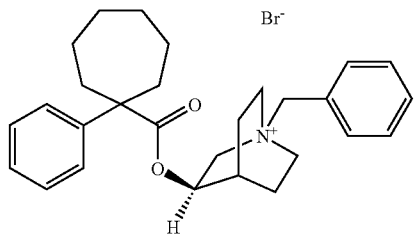

To (3R)-3-{[(1-phenylcycloheptyl)carbonyl]oxy}-1-azabicyclo[2.2.2]octane (Example 1) (0.1 g) in acetonitrile (5 mL) was added benzyl bromide (0.15 mL). The reaction was stirred at room temperature overnight and the acetonitrile was removed under reduced pressure. The solid was recrystallised with ethyl acetate/isohexane, filtered, washed with a small amount of ethyl acetate/isohexane and dried to afford the titled compound (145 mg).

m/e 418 [M]$^+$ $^1$H NMR (299.947 MHz, DMSO-D$_6$) δ 7.60-7.45 (m, 5H), 7.37-7.13 (m, 5H), 5.12-4.98 (m, 1H), 4.51 (d, 1H), 4.44 (d, 1H), 3.88-3.76 (m, 1H), 3.48-3.26 (m, 3H), 3.18 (d, 1H), 3.10-2.93 (m, 1H), 2.40-2.19 (m, 2H), 2.18-2.03 (m, 2H), 2.01-1.77 (m, 2H), 1.76-1.61 (m, 1H), 1.61-1.43 (m, 10H).

EXAMPLE 7

(3R)-3-{[(1-Phenylcycloheptyl)carbonyl]oxy}-1-[3-(trifluoromethoxy)benzyl]-1-azoniabicyclo[2.2.2]octane Bromide

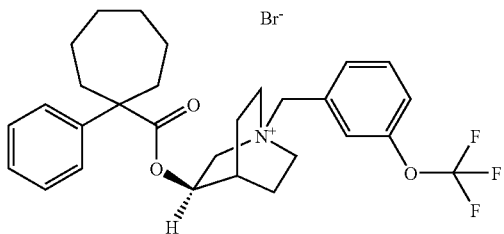

To (3R)-3-{[(1-Phenylcycloheptyl)carbonyl]oxy}-1-azabicyclo[2.2.2]octane (Example 1) (0.1 g) in acetonitrile (5 mL) was added 3-trifluoromethoxybenzyl bromide (0.15 mL). The reaction was stirred at room temperature overnight and the acetonitrile was removed under reduced pressure. The solid was recrystallised with ethyl acetate/isohexane, filtered, washed with ethyl acetate/isohexane and dried to afford the sub-titled compound (160 mg).

m/e 502 [M]$^+$ $^1$H NMR (299.947 MHz, DMSO-D$_6$) δ 7.44 (t, 1H), 7.36-7.17 (m, 3H), 7.17-7.01 (m, 5H), 5.12-5.02 (m, 1H), 4.49 (d, 1H), 4.43 (d, 1H), 3.92-3.78 (m, 1H), 3.51-3.28 (m, 3H), 3.20 (d, 1H), 3.12-2.94 (m, 1H), 2.46-2.20 (m, 2H), 2.19-2.05 (m, 2H), 2.04-1.80 (m, 2H), 1.78-1.62 (m, 1H), 1.61-1.45 (m, 10H).

EXAMPLE 8

(3R)-1-(3,4-Difluorobenzyl)-3-{[(1-phenylcycloheptyl)carbonyl]oxy}-1-azoniabicyclo[2.2.2]octane Bromide

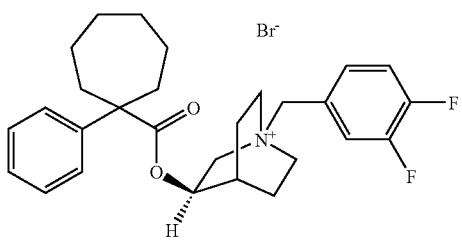

To (3R)-3-{[(1-phenylcycloheptyl)carbonyl]oxy}-1-azabicyclo[2.2.2]octane (Example 1) (0.1 g) in acetonitrile (5 mL) was added 3,4-difluorobenzyl bromide (0.15 mL). The reaction was stirred at room temperature overnight and the acetonitrile was removed under reduced pressure. The solid was recrystallised with ethyl acetate/isohexane, filtered, washed with ethyl acetate/isohexane and dried to afford the titled compound (100 mg).

m/e 454 [M]$^+$ $^1$H NMR (299.947 MHz, DMSO-D$_6$) δ 7.70-7.55 (m, 2H), 7.42-7.19 (m, 6H), 5.11-5.03 (m, 1H), 4.51 (d, 1H), 4.47 (s, 1H), 3.86-3.74 (m, 1H), 3.48-3.25 (m, 3H), 3.15 (d, 1H), 3.10-2.95 (m, 1H), 2.44-2.21 (m, 2H), 2.19-2.05 (m, 2H), 2.03-1.76 (m, 2H), 1.75-1.60 (m, 1H), 1.61-1.44 (m, 10H).

EXAMPLE 9

(3R)-3-{[(1-Phenylcycloheptyl)carbonyl]oxy}-1-{[5-(trifluoromethyl)-2-furyl]methyl}-1-azoniabicyclo[2.2.2]octane Bromide

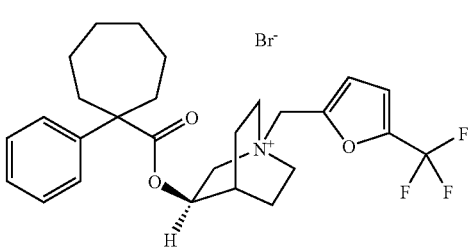

To (3R)-3-{[(1-phenylcycloheptyl)carbonyl]oxy}-1-azabicyclo[2.2.2]octane (Example 1) (0.1 g) in acetonitrile (2.5 mL) was added 2-trifluoromethyl-5-bromomethyl furan (0.12 mL). The reaction was stirred at room temperature overnight and the acetonitrile was removed under reduced pressure. The solid was recrystallised with ethyl acetate/isohexane, filtered, washed with ethyl acetate/isohexane and dried to afford the sub-titled compound (47 mg).

m/e 476 [M]$^+$ $^1$H NMR (299.947 MHz, DMSO-D$_6$) δ 7.43-7.39 (m, 1H), 7.37-7.20 (m, 5H), 7.06 (d, 1H), 5.10-5.02 (m, 1H), 4.69 (s, 2H), 3.94-3.82 (m, 1H), 3.51-3.27 (m, 3H), 3.22 (d, 1H), 3.16-2.99 (m, 1H), 2.43-2.22 (m, 2H), 2.21-2.07 (m, 2H), 2.04-1.80 (m, 2H), 1.79-1.65 (m, 1H), 1.64-1.38 (m, 10H).

EXAMPLE 10

(3R)-1-(3-Methoxybenzyl)-3-{[(1-phenylcycloheptyl)carbonyl]oxy}-1-azoniabicyclo[2.2.2]octane Bromide

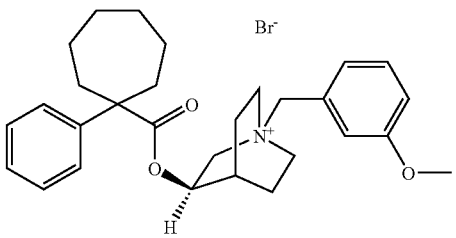

To (3R)-3-{[(1-phenylcycloheptyl)carbonyl]oxy}-1-azabicyclo[2.2.2]octane (Example 1) (0.1 g) in acetonitrile (5 mL) was added 3-methoxybenzyl bromide (0.15 mL). The reaction was stirred at room temperature overnight and the acetonitrile was removed under reduced pressure. The residue was dissolved in ethyl acetate and precipitated with isohexane, and the supernatant containing unreacted benzyl bromide was carefully separated. The residue was dried to afford the sub-titled compound (52 mg).

m/e 448 [M]$^+$ $^1$H NMR (299.947 MHz, DMSO-D$_6$) δ 7.44 (t, 1H), 7.36-7.17 (m, 5H), 7.17-7.01 (m, 3H), 5.12-5.02 (m, 1H), 4.49 (d,

1H), 4.43 (d, 1H), 3.92-3.78 (m, 1H), 3.80 (s, 3H), 3.51-3.28 (m, 3H), 3.20 (d, 1H), 3.12-2.94 (m, 1H), 2.46-2.20 (m, 2H), 2.19-2.05 (m, 2H), 2.04-1.80 (m, 2H), 1.78-1.62 (m, 1H), 1.61-1.45 (m, 10H).

EXAMPLE 11

(3R)-1-(2-Phenoxyethyl)-3-{[(1-phenylcycloheptyl)carbonyl]oxy}-1-azoniabicyclo[2.2.2]octane bromide

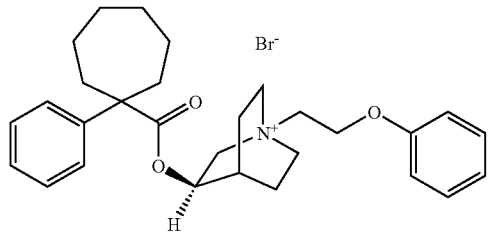

The titled compound was prepared by a procedure analogous to the method of Example 3, using (3R)-3-{[(1-phenylcycloheptyl)carbonyl]oxy}-1-azabicyclo[2.2.2]octane (Example 1) and 2-phenoxyethyl bromide.

m/e 448 [M]+

$^1$H NMR (299.947 MHz, DMSO-D$_6$) δ 7.45-7.12 (m, 7H), 7.10-6.90 (m, 3H), 5.14-4.99 (m, 1H), 4.49-4.33 (m, 2H), 4.09-3.92 (m, 1H), 3.81-3.64 (m, 1H), 3.63-3.44 (m, 2H), 3.23-3.05 (m, 1H), 2.44-2.22 (m, 4H), 2.22-2.06 (m, 2H), 2.04-1.82 (m, 4H), 1.79-1.65 (m, 2H), 1.65-1.41 (m, 8H).

EXAMPLE 12

(3R)-1-[2-(Benzyloxy)ethyl]-3-{[(1-phenylcycloheptyl)carbonyl]oxy}-1-azoniabicyclo[2.2.2]octane Bromide

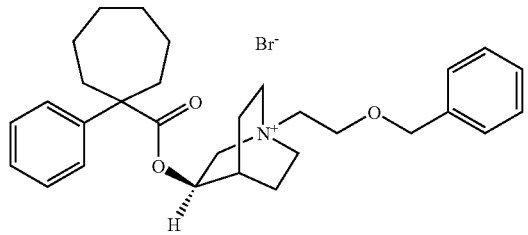

The titled compound was prepared by a procedure analogous to the method of Example 3, using (3R)-3-{[(1-phenylcycloheptyl)carbonyl]oxy}-1-azabicyclo[2.2.2]octane (Example 1) and [(2-bromoethoxy)methyl]benzene.

m/e 462 [M]+

$^1$H NMR (399.826 MHz, DMSO-D$_6$) δ 7.41-7.28 (m, 9H), 7.26-7.21 (m, 1H), 5.09-5.02 (m, 1H), 4.51 (s, 2H), 3.98-3.88 (m, 2H), 3.87-3.74 (m, 1H), 3.52-3.46 (m, 2H), 3.45-3.37 (m, 2H), 3.16-3.04 (m, 1H), 2.41-2.23 (m, 3H), 2.19-2.08 (m, 2H), 2.03-1.80 (m, 4H), 1.77-1.63 (m, 2H), 1.63-1.41 (m, 8H).

EXAMPLE 13

(3R)-1-[2-(Isoxazol-3-ylamino)-2-oxoethyl]-3-({[1-(2-thienyl)cycloheptyl]carbonyl}oxy)-1-azoniabicyclo[2.2.2]octane Bromide a) 1-[5-(Trimethylsilyl)-2-thienyl]cycloheptanol

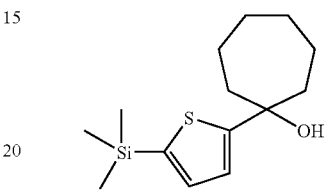

To 1,4 dibromothiophene (8.46 g) in ether (125 mL) was added butyl lithium in hexane (14 mL of 2.5 M solution) at −78° C. under nitrogen. After 15 minutes chlorotrimethylsilane (3.8 g) was added. The reaction was allowed to warm to room temperature stirred for 30 minutes and cooled back to −78° C. Butyl lithium in hexane (14 mL of 2.5 M solution) was added and after 15 minutes cycloheptanone (3.93 g) was added. The reaction was allowed to warm to room temperature and stirred overnight. Water (50 mL) was added and the product was extracted into isohexane (2×250 mL) which was dried and evaporated to afford 1-[5-(Trimethylsilyl)-2-thienyl]cycloheptanol (9.4 g).

$^1$H NMR (299.946 MHz, CDCl$_3$) δ 7.08 (d, 1H), 7.03 (d, 1H), 2.21-1.98 (m, 4H), 1.90 (s, 1H), 1.85-1.40 (m, 8H), 0.30 (s, 9H).

b) [5-(1-Methoxycycloheptyl)-2-thienyl](trimethyl)silane

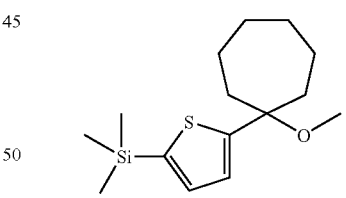

To 1-[5-(trimethylsilyl)-2-thienyl]cycloheptanol (Example 13a) (9.4 g) dissolved in tetrahydrofuran (200 mL) sodium hydride (60% in oil, 2.52 g) was added. The reaction was stirred for 5 minutes and iodomethane (8.05 g) added. The mixture was stirred at 65° C. overnight with a reflux condenser and then further quantities of sodium hydride (60% in oil, 1.0 g) and iodomethane (1 mL) were added and the reaction was stirred at 65° C. for a further 24 hours with a reflux condenser. The reaction mixture was cooled and water (200 mL) was added carefully. The reaction mixture was extracted with isohexane (2×200 mL) and the organic layer was separated, dried (MgSO$_4$) and evaporated to afford the sub-titled compound (10.66 g) containing some oil from the sodium hydride.

¹H NMR (299.946 MHz, CDCl₃) δ 7.08 (d, 1H), 6.98 (d, 1H), 3.05 (s, 3H), 2.17 (dd, 2H), 2.04 (dd, 2H), 1.82-1.40 (m, 8H), 0.30 (s, 9H).

c) Methyl 1-(2-thienyl)cycloheptanecarboxylate

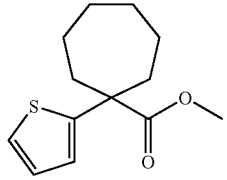

Potassium (1.42 g) and sodium (0.4 g) were heated together at 120° C. in mineral oil under an environment of nitrogen for 30 minutes and then cooled to room temperature. The oil was removed and replaced with ether (100 mL) and [5-(1-Methoxycycloheptyl)-2-thienyl](trimethyl)silane (Example 13b) (5.0 g) was added and the reaction was stirred under nitrogen overnight at room temperature. The reaction was cooled to -78° C. and solid carbon dioxide (~20 g) was added with stirring. The reaction was allowed to warm to room temperature and water (100 mL) was added carefully under an environment of nitrogen. Once the metal was destroyed the reaction was poured into a separating funnel. Three layers formed of which the middle was the salt of the intermediate product. This was evaporated to dryness then refluxed in methanol (125 mL) and concentrated hydrochloric acid (10 mL) overnight. Methanol was removed and water (50 mL) was added and the product was extracted with ether (2×50 mL) which was dried and evaporated. The product was purified on silica eluting with isohexane/2.5% ethylacetate. Relevant fraction were evaporated to afford the sub-titled compound (1.9 g).

¹H NMR (299.946 MHz, CDCl₃) δ 7.18 (dd, 1H), 6.96-6.90 (m, 2H), 3.66 (s, 3H), 2.54 (dd, 2H), 2.10 (dd, 2H), 1.69-1.49 (m, 8H).

d) (3R)-1-Azabicyclo[2.2.2]oct-3-yl 1-(2-thienyl)cycloheptanecarboxylate

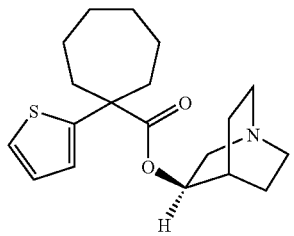

Methyl 1-(2-thienyl)cycloheptanecarboxylate (Example 13c) (0.27 g) and (R)-quinuclidin-3-ol (0.288 g) were refluxed in toluene (100 mL) containing sodium hydride (~10 mg) in a Dean and Stark apparatus for 24 hours. The reaction was partitioned between water (50 mL) and ether (2×50 mL) and the ether layer was separated, dried (MgSO₄) and evaporated. The crude product was purified by column chromatography on silica eluting with ethyl acetate/triethylamine (99/1) to afford the titled compound (0.24 g) as an oil.

m/e 334 [M+H]⁺ e) (3R)-1-[2-(Isoxazol-3-ylamino)-2-oxoethyl]-3-({[1-(2-thienyl)cycloheptyl]carbonyl}oxy)-1-azoniabicyclo[2.2.2]octane Bromide

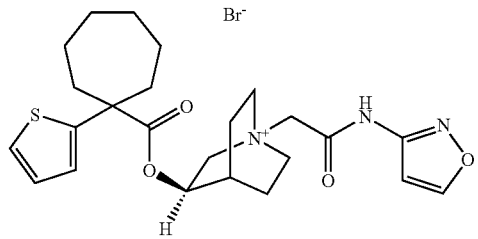

To (3R)-1-Azabicyclo[2.2.2]oct-3-yl 1-(2-thienyl)cycloheptanecarboxylate (Example 13d) (0.12 g) in acetonitrile (5 mL) was added 2-bromo-N-isoxazol-3-yl-acetamide (Example 4a) (73.8 mg). The reaction was stirred at room temperature overnight and the product crystallised. The solid was recrystallised three times with ethyl acetate, filtered and dried to afford the titled compound (103 mg).

m/e 458 [M]⁺

¹H NMR (299.947 MHz, DMSO-D₆) δ 11.79 (s, 1H), 8.90 (d, 1H), 7.44 (dd, 1H), 7.03 (dd, 1H), 6.99 (dd, 1H), 6.91 (s, 1H), 5.16-5.07 (m, 1H), 4.35 (s, 2H), 4.19-3.99 (m, 1H), 3.77-3.56 (m, 4H), 3.56-3.41 (m, 1H), 2.48-2.36 (m, 1H), 2.33-2.10 (m, 2H), 2.09-1.65 (m, 6H), 1.63-1.46 (m, 8H).

EXAMPLE 14

(3R)-1-(2-Oxo-2-pyrrolidin-1-ylethyl)-3-{[(1-phenylcycloheptyl)carbonyl]oxy}-1-azoniabicyclo[2.2.2]octane Bromide

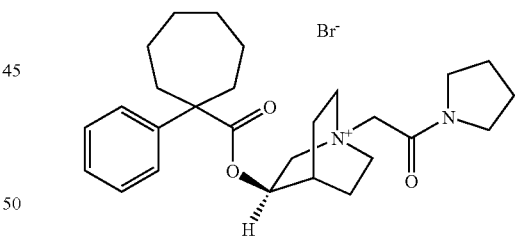

The titled compound was prepared by a procedure analogous to the method of Example 3, using (3R)-3-{[(1-phenylcycloheptyl)carbonyl]oxy}-1-azabicyclo[2.2.2]octane (Example 1) and 1-(bromoacetyl)pyrrolidine.

m/e 439 [M]⁺

¹H NMR (399.826 MHz, DMSO-D₆) δ 7.38-7.30 (m, 4H), 7.24 (tt, 1H), 5.14-5.08 (m, 1H), 4.31-4.21 (m, 2H), 4.12-4.03 (m, 1H), 3.65 (d, 1H), 3.58 (t, 2H), 3.52-3.40 (m, 1H), 3.41-3.29 (m, 4H), 2.42-2.26 (m, 2H), 2.21-2.11 (m, 2H), 2.02-1.86 (m, 5H), 1.85-1.64 (m, 3H), 1.69-1.43 (m, 10H).

EXAMPLE 15

(3R)-1-(2-Morpholin-4-yl-2-oxoethyl)-3-{[(1-phenylcycloheptyl)carbonyl]oxy}-1-azoniabicyclo[2.2.2]octane Bromide

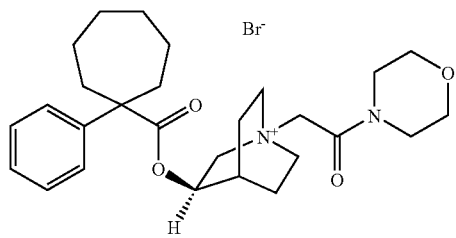

The titled compound was prepared by a procedure analogous to the method of Example 3, using (3R)-3-{[(1-phenylcycloheptyl)carbonyl]oxy}-1-azabicyclo[2.2.2]octane (Example 1) and 1-(bromoacetyl)morpholine.

m/e 455 [M]$^+$ $^1$H NMR (399.826 MHz, DMSO-D$_6$) δ 7.38-7.30 (m, 4H), 7.25 (tt, 1H), 5.15-5.08 (m, 1H), 4.39 (d, 1H), 4.35 (s, 1H), 4.09-4.01 (m, 1H), 3.65-3.50 (m, 8H), 3.46 (t, 2H), 3.37 (t, 2H), 2.42-2.26 (m, 2H), 2.22-2.10 (m, 2H), 2.02-1.87 (m, 3H), 1.74 (m, 1H), 1.65-1.47 (m, 10H).

EXAMPLE 16

(3R)-1-[2-Oxo-2-(pyrazin-2-ylamino)ethyl]-3-{[(1-phenylcycloheptyl)carbonyl]oxy}-1-azoniabicyclo[2.2.2]octane Bromide

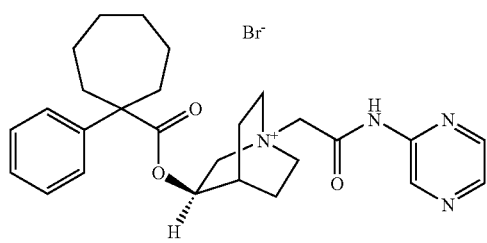

The titled compound was prepared by a procedure analogous to the method of Example 3, using (3R)-3-{[(1-phenylcycloheptyl)carbonyl]oxy}-1-azabicyclo[2.2.2]octane (Example 1) and 2-bromo-N-pyrazin-2-ylacetamide.

m/e 463 [M]$^+$ $^1$H NMR (399.826 MHz, DMSO-D$_6$) δ 11.37 (s, 1H), 9.28 (s, 1H), 8.50-8.46 (m, 2H), 7.39-7.30 (m, 4H), 7.27-7.21 (m, 1H), 5.16-5.08 (m, 1H), 4.33 (s, 2H), 4.17-4.07 (m, 1H), 3.69-3.56 (m, 4H), 3.48-3.38 (m, 1H), 2.44-2.26 (m, 3H), 2.25-2.04 (m, 2H), 2.03-1.87 (m, 3H), 1.85-1.71 (m, 1H), 1.68-1.45 (m, 8H).

EXAMPLE 17

(3R)-1-[2-Oxo-2-(pyridazin-3-ylamino)ethyl]-3-{[(1-phenylcycloheptyl)carbonyl]oxy}-1-azoniabicyclo[2.2.2]octane Bromide

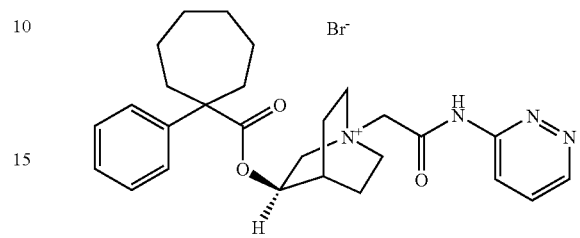

The titled compound was prepared by a procedure analogous to the method of Example 3, using (3R)-3-{[(1-phenylcycloheptyl)carbonyl]oxy}-1-azabicyclo[2.2.2]octane (Example 1) and 2-bromo-N-pyridazin-3-ylacetamide.

m/e 463 [M]$^+$ $^1$H NMR (399.826 MHz, DMSO-D$_6$) δ 11.68 (s, 1H), 9.06 (dd, 1H), 8.25 (d, 1H), 7.79 (dd, 1H), 7.39-7.30 (m, 4H), 7.27-7.21 (m, 1H), 5.15-5.10 (m, 1H), 4.34 (s, 2H), 4.16-4.06 (m, 2H), 3.69-3.56 (m, 4H), 3.46-3.36 (m, 1H), 2.43-2.27 (m, 2H), 2.24-2.10 (m, 2H), 2.04-1.89 (m, 3H), 1.84-1.71 (m, 1H), 1.68-1.45 (m, 8H).

EXAMPLE 18

(3R)-1-{2-Oxo-2-[(2-phenoxyethyl)amino]ethyl}-3-{[(1-phenylcycloheptyl)carbonyl]oxy}-1-azoniabicyclo[2.2.2]octane Bromide

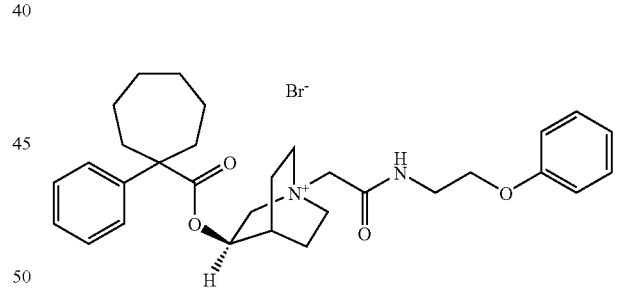

The titled compound was prepared by a procedure analogous to the method of Example 3, using (3R)-3-{[(1-phenylcycloheptyl)carbonyl]oxy}-1-azabicyclo[2.2.2]octane (Example 1) and 2-bromo-N-(2-phenoxyethyl)acetamide.

m/e 505 [M]$^+$ $^1$H NMR (399.826 MHz, DMSO-D$_6$) δ 8.82 (t, 1H), 7.38-7.21 (m, 7H), 6.98-6.91 (m, 3H), 5.12-5.07 (m, 1H), 4.12-3.97 (m, 4H), 3.64-3.46 (m, 4H), 3.37-3.27 (m, 3H), 3.18 (s,

1H), 3.16 (s, 1H), 2.42-2.25 (m, 2H), 2.19-2.10 (m, 2H), 2.00-1.82 (m, 3H), 1.79-1.67 (m, 1H), 1.65-1.44 (m, 8H).

EXAMPLE 19

(3R)-1-[2-(3-Fluorophenyl)-2-oxoethyl]-3-{[(1-phenylcycloheptyl)carbonyl]oxy}-1-azoniabicyclo[2.2.2]octane Bromide

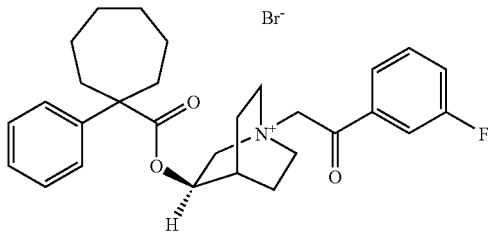

The titled compound was prepared by a procedure analogous to the method of Example 3, using (3R)-3-{[(1-phenylcycloheptyl)carbonyl]oxy}-1-azabicyclo[2.2.2]octane (Example to 1) and 2-bromo-1-(3-fluorophenyl)ethanone.

m/e 464 [M]$^+$ $^1$H NMR (399.826 MHz, DMSO-D$_6$) δ 7.85-7.77 (m, 2H), 7.71-7.59 (m, 2H), 7.40-7.32 (m, 4H), 7.29-7.23 (m, 1H), 5.20-5.14 (m, 3H), 4.16-4.06 (m, 1H), 3.69-3.54 (m, 4H), 3.50-3.37 (m, 1H), 3.30 (d, 1H), 2.44-2.29 (m, 2H), 2.27-2.11 (m, 2H), 2.06-1.92 (m, 3H), 1.89-1.74 (m, 1H), 1.68-1.45 (m, 8H).

EXAMPLE 20

(3R)-1-{2-[(5-Methylisoxazol-3-yl)amino]-2-oxoethyl}-3-{[(1-phenylcycloheptyl)carbonyl]oxy}-1-azoniabicyclo[2.2.2]octane Bromide

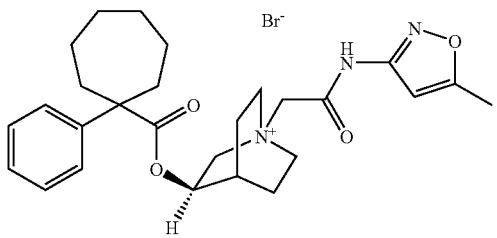

The titled compound was prepared by a procedure analogous to the method of Example 3, using (3R)-3-{[(1-phenylcycloheptyl)carbonyl]oxy}-1-azabicyclo[2.2.2]octane (Example 1) and 2-bromo-N-(5-methylisoxazol-3-yl)acetamide.

m/e 466 [M]$^+$ $^1$H NMR (399.826 MHz, DMSO-D$_6$) δ 11.55 (s, 1H), 7.40-7.28 (m, 4H), 7.28-7.20 (m, 1H), 6.61 (s, 1H), 5.15-5.07 (m, 1H), 4.32 (d, 1H), 4.27 (d, 1H), 4.15-4.06 (m, 1H), 3.67-3.53 (m, 4H), 3.44-3.38 (m, 1H), 3.30-3.28 (m, 1H), 2.41 (s, 3H), 2.39-2.27 (m, 2H), 2.23-2.11 (m, 2H), 2.03-1.87 (m, 3H), 1.82-1.71 (m, 1H), 1.70-1.43 (m, 8H).

EXAMPLE 21

(3R)-1-{2-[(6-Chloropyridazin-3-yl)amino]-2-oxoethyl}-3-{[(1-phenylcycloheptyl)carbonyl]oxy}-1-azoniabicyclo[2.2.2]octane Bromide

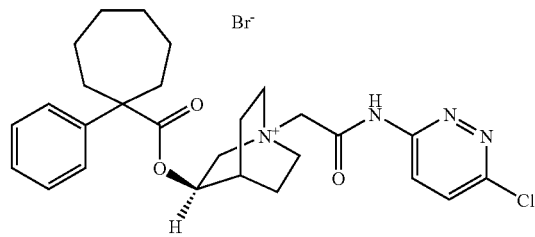

The titled compound was prepared by a procedure analogous to the method of Example 3, using (3R)-3-{[(1-phenylcycloheptyl)carbonyl]oxy}-1-azabicyclo[2.2.2]octane (Example 1) and 2-bromo-N-(6-chloropyridazin-3-yl)acetamide.

m/e 497 [M]$^+$ $^1$H NMR (399.826 MHz, DMSO-D$_6$) δ 11.88 (s, 1H), 8.31 (d, 1H), 8.01 (d, 1H), 7.39-7.30 (m, 4H), 7.28-7.21 (m, 1H), 5.15-5.08 (m, 1H), 4.40-4.31 (m, 2H), 4.15-4.07 (m, 1H), 3.69-3.55 (m, 4H), 3.47-3.30 (m, 2H), 2.42-2.27 (m, 2H), 2.23-2.11 (m, 2H), 2.03-1.86 (m, 3H), 1.82-1.71 (m, 1H), 1.69-1.43 (m, 8H).

EXAMPLE 22

(3R)-1-{2-[(3-Fluorophenyl)amino]-2-oxoethyl}-3-{[(1-phenylcycloheptyl)carbonyl]oxy}-1-azoniabicyclo[2.2.2]octane Bromide

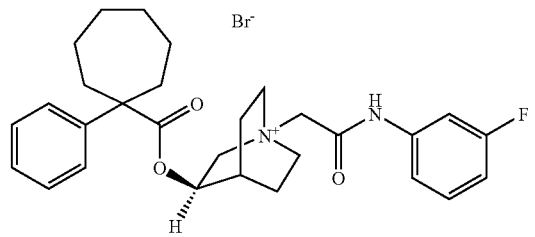

The titled compound was prepared by a procedure analogous to the method of Example 3, using (3R)-3-{[(1-phenylcycloheptyl)carbonyl]oxy}-1-azabicyclo[2.2.2]octane (Example 1) and 2-bromo-N-(3-fluorophenyl)acetamide.

m/e 479 [M]$^+$ $^1$H NMR (399.826 MHz, DMSO-D$_6$) δ 10.86 (s, 1H), 7.59 (d, 1H), 7.42 (dd, 1H), 7.38-7.28 (m, 5H), 7.26-7.20 (m, 1H), 7.03-6.95 (m, 1H), 5.17-5.09 (m, 1H), 4.35-4.23 (m, 2H), 4.16-4.07 (m, 1H), 3.71-3.57 (m, 4H), 3.49-3.36 (m, 1H), 2.42-2.27 (m, 2H), 2.24-2.10 (m, 2H), 2.03-1.85 (m, 3H), 1.84-1.70 (m, 1H), 1.69-1.43 (m, 9H).

EXAMPLE 23

(3R)-1-[2-(2-Naphthyl)ethyl]-3-{[(1-phenylcycloheptyl)carbonyl]oxy}-1-azoniabicyclo[2.2.2]octane Bromide

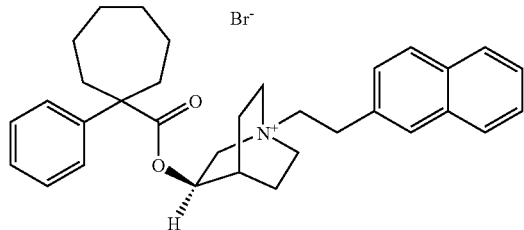

The titled compound was prepared by a procedure analogous to the method of Example 3, using (3R)-3-{[(1-phenylcycloheptyl)carbonyl]oxy}-1-azabicyclo[2.2.2]octane (Example 1) and 2-(2-bromoethyl)naphthalene.

m/e 482 [M]+

$^1$H NMR (399.826 MHz, DMSO-D$_6$) δ 7.40-7.31 (m, 4H), 7.29-7.22 (m, 2H), 6.93 (s, 1H), 6.88 (d, 1H), 6.84 (dd, 1H), 5.12-5.06 (m, 1H), 3.97-3.87 (m, 1H), 3.76 (s, 3H), 3.60-3.36 (m, 6H), 3.26 (d, 1H), 3.14-3.02 (m, 1H), 3.02-2.85 (m, 2H), 2.44-2.27 (m, 2H), 2.23-2.11 (m, 2H), 2.03-1.83 (m, 3H), 1.78-1.65 (m, 1H), 1.66-1.43 (m, 8H).

EXAMPLE 24

(3R)-1-[2-(3-Methoxyphenyl)ethyl]-3-{[(1-phenylcycloheptyl)carbonyl]oxy}-1-azoniabicyclo[2.2.2]octane Bromide

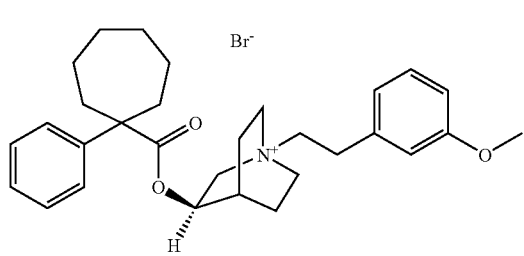

The titled compound was prepared by a procedure analogous to the method of Example 3, using (3R)-3-{[(1-phenylcycloheptyl)carbonyl]oxy}-1-azabicyclo[2.2.2]octane (Example 1) and 1-(2-bromoethyl)-3-methoxybenzene.

m/e 462 [M]+

$^1$H NMR (399.826 MHz, DMSO-D$_6$) δ 7.40-7.31 (m, 4H), 7.29-7.22 (m, 2H), 6.93 (s, 1H), 6.88 (d, 1H), 6.84 (dd, 1H), 5.12-5.06 (m, 1H), 3.97-3.87 (m, 1H), 3.76 (s, 3H), 3.60-3.40 (m, 5H), 3.26 (d, 1H), 3.14-3.02 (m, 1H), 3.02-2.85 (m, 2H), 2.44-2.27 (m, 2H), 2.23-2.11 (m, 2H), 2.03-1.83 (m, 3H), 1.78-1.65 (m, 1H), 1.66-1.43 (m, 9H).

EXAMPLE 25

(3R)-1-[2-(5-Methyl-2-thienyl)ethyl]-3-{[(1-phenylcycloheptyl)carbonyl]oxy}-1-azoniabicyclo[2.2.2]octane Bromide

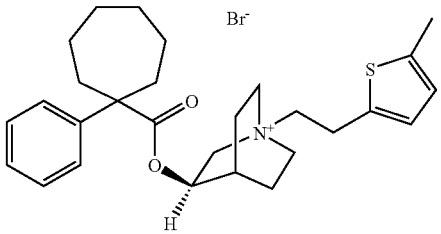

The titled compound was prepared by a procedure analogous to the method of Example 3, using (3R)-3-{[(1-phenylcycloheptyl)carbonyl]oxy}-1-azabicyclo[2.2.2]octane (Example 1) and 2-(2-bromoethyl)-5-methylthiophene.

m/e 452 [M]+

$^1$H NMR (399.826 MHz, DMSO-D$_6$) δ 7.38-7.31 (m, 4H), 7.28-7.22 (m, 1H), 6.76 (d, 1H), 6.67 (dd, 1H), 5.10-5.02 (m, 1H), 3.91-3.82 (m, 1H), 3.52-3.34 (m, 5H), 3.23 (d, 1H), 3.19-2.98 (m, 3H), 2.40 (s, 3H), 2.38-2.27 (m, 2H), 2.22-2.13 (m, 2H), 2.03-1.82 (m, 3H), 1.74-1.41 (m, 10H).

EXAMPLE 26

(3R)-3-{[(1-Phenylcycloheptyl)carbonyl]oxy}-1-(2-phenylethyl)-1-azoniabicyclo[2.2.2]octane Bromide

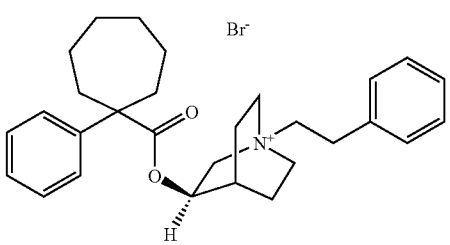

The titled compound was prepared by a procedure analogous to the method of Example 3, using (3R)-3-{[(1-phenylcycloheptyl)carbonyl]oxy}-1-azabicyclo[2.2.2]octane (Example 1) and (2-bromoethyl)benzene.

m/e 432 [M]+

$^1$H NMR (399.826 MHz, DMSO-D$_6$) δ 7.39-7.22 (m, 10H), 5.12-5.06 (m, 1H), 3.94-3.86 (m, 1H), 3.55-3.46 (m, 1H), 3.42 (t, 4H), 3.24 (d, 1H), 3.11-3.01 (m, 1H), 3.01-2.88

(m, 2H), 2.43-2.27 (m, 2H), 2.23-2.13 (m, 2H), 2.05-1.82 (m, 3H), 1.77-1.65 (m, 1H), 1.65-1.42 (m, 9H).

EXAMPLE 27

(3R)-3-{[(1-Phenylcycloheptyl)carbonyl]oxy}-1-{2-[3-(trifluoromethyl)phenyl]ethyl}-1-azoniabicyclo[2.2.2]octane Bromide

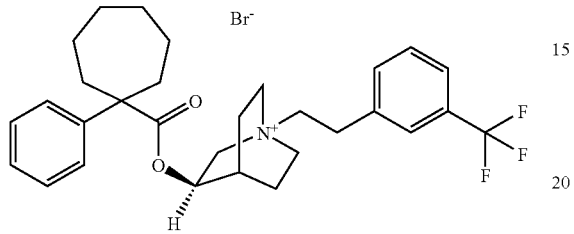

The titled compound was prepared by a procedure analogous to the method of Example 3, using (3R)-3-{[(1-phenylcycloheptyl)carbonyl]oxy}-1-azabicyclo[2.2.2]octane (Example 1) and 1-(2-bromoethyl)-3-(trifluoromethyl)benzene.

m/e 500 [M]+

$^1$H NMR (399.826 MHz, DMSO-D$_6$) δ 7.75 (s, 1H), 7.68-7.57 (m, 3H), 7.40-7.31 (m, 4H), 7.28-7.22 (m, 1H), 5.13-5.08 (m, 1H), 3.95-3.86 (m, 1H), 3.56-3.39 (m, 5H), 3.26 (d, 1H), 3.18-3.00 (m, 3H), 2.44-2.28 (m, 2H), 2.22-2.13 (m, 2H), 2.05-1.82 (m, 3H), 1.79-1.67 (m, 1H), 1.66-1.43 (m, 9H).

EXAMPLE 28

(3R)-1-[2-(1,3-Benzodioxol-5-yl)ethyl]-3-{[(1-phenylcycloheptyl)carbonyl]oxy}-1-azoniabicyclo[2.2.2]octane bBromide

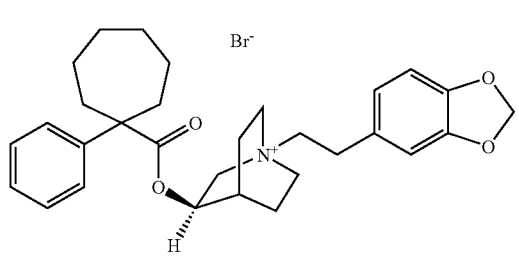

The titled compound was prepared by a procedure analogous to the method of Example 3, using (3R)-3-{[(1-phenylcycloheptyl)carbonyl]oxy}-1-azabicyclo[2.2.2]octane (Example 1) and 5-(2-bromoethyl)-1,3-benzodioxole.

m/e 476 [M]+

$^1$H NMR (399.826 MHz, DMSO-D$_6$) δ 7.39-7.31 (m, 4H), 7.27-7.22 (m, 1H), 6.92 (d, 1H), 6.88 (d, 1H), 6.76 (dd, 1H), 5.99 (s, 2H), 5.12-5.05 (m, 1H), 3.90-3.83 (m, 1H), 3.50-3.42 (m, 1H), 3.41-3.32 (m, 4H), 3.21 (d, 1H), 3.08-2.99 (m, 1H), 2.93-2.79 (m, 2H), 2.43-2.27 (m, 2H), 2.21-2.13 (m, 2H), 2.03-1.80 (m, 3H), 1.75-1.65 (m, 1H), 1.64-1.44 (m, 9H).

EXAMPLE 29

(3R)-1-[2-(4-Cyanophenyl)ethyl]-3-{[(1-phenylcycloheptyl)carbonyl]oxy}-1-azoniabicyclo[2.2.2]octane Bromide

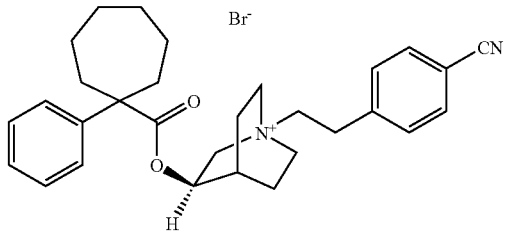

The titled compound was prepared by a procedure analogous to the method of Example 3, using (3R)-3-{[(1-phenylcycloheptyl)carbonyl]oxy}-1-azabicyclo[2.2.2]octane (Example 1) and 4-(2-bromoethyl)benzonitrile.

m/e 457 [M]+

$^1$H NMR (399.826 MHz, DMSO-D$_6$) δ 7.85 (dd, 2H), 7.54 (d, 2H), 7.39-7.31 (m, 4H), 7.25 (td, 1H), 5.12-5.07 (m, 1H), 3.92-3.85 (m, 1H), 3.52-3.37 (m, 5H), 3.23 (d, 1H), 3.14-3.00 (m, 3H), 2.42-2.27 (m, 2H), 2.21-2.13 (m, 2H), 2.03-1.85 (m, 3H), 1.76-1.65 (m, 1H), 1.65-1.46 (m, 9H).

EXAMPLE 30

(3R)-1-[2-(1,3-Dioxo-1,3-dihydro-2H-isoindol-2-yl)ethyl]-3-{[(1-phenylcycloheptyl)carbonyl]oxy}-1-azoniabicyclo[2.2.2]octane Bromide

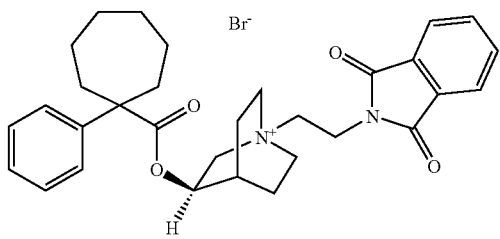

The titled compound was prepared by a procedure analogous to the method of Example 3, using (3R)-3-{[(1-phenylcycloheptyl)carbonyl]oxy}-1-azabicyclo[2.2.2]octane (Example 1) and 2-(2-bromoethyl)-1H-isoindole-1,3(2H)-dione.

m/e 501 [M]+

$^1$H NMR (399.826 MHz, DMSO-D$_6$) δ 7.95-7.85 (m, 4H), 7.38-7.31 (m, 4H), 7.28-7.22 (m, 1H), 5.08-5.02 (m, 1H), 4.01-3.91 (m, 3H), 3.56-3.37 (m, 5H), 3.30-3.27 (m, 1H), 3.23-3.13 (m, 1H), 2.45-2.27 (m, 2H), 2.26-2.12 (m, 2H), 2.01-1.81 (m, 3H), 1.75-1.41 (m, 10H).

EXAMPLE 31

(3R)-1-{2-[(6-Chloropyrazin-2-yl)amino]-2-oxoethyl}-3-{[(1-phenylcycloheptyl)carbonyl]oxy}-1-azoniabicyclo[2.2.2]octane Bromide

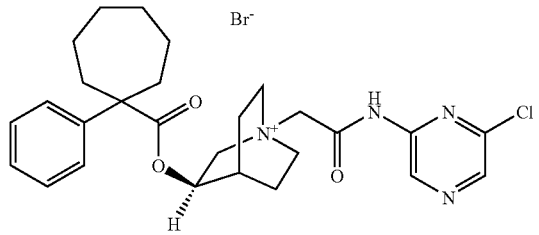

The titled compound was prepared by a procedure analogous to the method of Example 3, using (3R)-3-{[(1-phenylcycloheptyl)carbonyl]oxy}-1-azabicyclo[2.2.2]octane (Example 1) and 2-bromo-N-(6-chloropyrazin-2-yl)acetamide.

m/e 497 [M]$^+$ $^1$H NMR (399.826 MHz, DMSO-D$_6$) δ 11.69 (s, 1H), 9.24 (s, 1H), 8.61 (d, 1H), 7.38-7.31 (m, 4H), 7.271-7.22 (m, 1H), 5.15-5.09 (m, 1H), 4.37-4.27 (m, 2H), 4.16-4.07 (m, 1H), 3.69-3.57 (m, 4H), 3.42 (dd, 1H), 2.43-2.27 (m, 2H), 2.24-2.10 (m, 2H), 2.04-1.85 (m, 3H), 1.84-1.71 (m, 1H), 1.69-1.46 (m, 9H).

EXAMPLE 32

(3R$^5$)-1-{[1-(4-Chlorophenyl)cyclopropyl]methyl}-3-{[(1-phenylcycloheptyl)carbonyl]oxy}-1-azoniabicyclo[2.2.2]octane Bromide

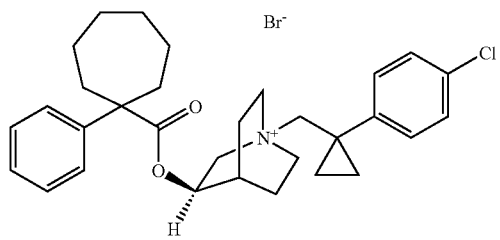

The titled compound was prepared by a procedure analogous to the method of Example 3, using (3R)-3-{[(1-phenylcycloheptyl)carbonyl]oxy}-1-azabicyclo[2.2.2]octane (Example 1) and 1-[1-(bromomethyl)cyclopropyl]-4-chlorobenzene.

m/e 492 [M]$^+$ $^1$H NMR (399.826 MHz, DMSO-D$_6$) δ 7.49 (dd, 2H), 7.42 (dd, 2H), 7.39-7.33 (m, 2H), 7.29-7.23 (m, 3H), 4.98-4.93 (m, 1H), 3.80 (d, 1H), 3.64 (ddd, 1H), 3.56 (d, 1H), 3.34-3.23 (m, 2H), 3.22-3.07 (m, 2H), 2.94-2.81 (m, 2H), 2.37-2.27 (m, 2H), 2.17 (s, 1H), 2.05 (s, 1H), 1.96-1.86 (m, 1H), 1.85-1.77 (m, 1H), 1.77-1.64 (m, 1H), 1.65-1.37 (m, 8H), 1.35-1.21 (m, 1H), 1.16-1.06 (m, 2H), 1.06-0.99 (m, 1H), 0.99-0.92 (m, 1H).

EXAMPLE 33

(3R)-1-{2-[(5-Methylpyrazin-2-yl)amino]-2-oxoethyl}-3-{[(1-phenylcycloheptyl)carbonyl]oxy}-1-azoniabicyclo[2.2.2]octane Bromide

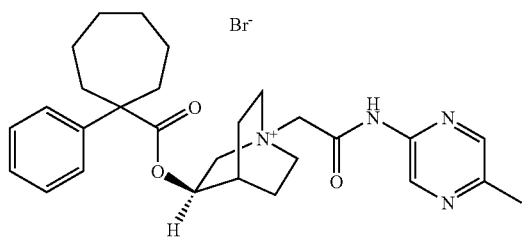

The titled compound was prepared by a procedure analogous to the method of Example 3, using (3R)-3-{[(1-phenylcycloheptyl)carbonyl]oxy}-1-azabicyclo[2.2.2]octane (Example 1) and 2-bromo-N-(5-methylpyrazin-2-yl)acetamide.

m/e 477 [M]$^+$ $^1$H NMR (399.826 MHz, DMSO-D$_6$) δ 11.28 (s, 1H), 9.15 (s, 1H), 8.36 (d, 1H), 7.38-7.31 (m, 4H), 7.27-7.22 (m, 1H), 5.16-5.08 (m, 1H), 4.31 (s, 2H), 4.16-4.08 (m, 1H), 3.69-3.55 (m, 4H), 3.46-3.27 (m, 2H), 2.48 (s, 3H), 2.42-2.29 (m, 2H), 2.23-2.11 (m, 2H), 2.03-1.87 (m, 3H), 1.83-1.72 (m, 1H), 1.70-1.45 (m, 8H).

EXAMPLE 34

(3R)-1-(Carboxymethyl)-3-{[(1-phenylcycloheptyl)carbonyl]oxy}-1-azoniabicyclo[2.2.2]octane Bromide a) (3R)-1-(2-tert-Butoxy-2-oxoethyl)-3-{[(1-phenylcycloheptyl)carbonyl]oxy}-1-azoniabicyclo[2.2.2]octane

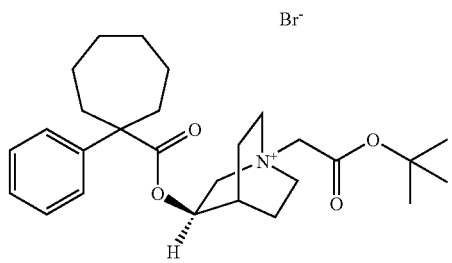

The titled compound was prepared by a procedure analogous to the method of Example 3, using (3R)-3-{[(1-phenylcycloheptyl)carbonyl]oxy}-1-azabicyclo[2.2.2]octane (Example 1) and tert-butyl bromoacetate.

m/e 442 [M]$^+$ $^1$H NMR (399.826 MHz, DMSO-D$_6$) δ 7.38-7.30 (m, 4H), 7.25 (tt, 1H), 5.14-5.09 (m, 1H), 4.31 (d, 1H), 4.27 (d, 1H), 4.07-4.00 (m, 1H), 3.61-3.47 (m, 4H), 3.39-3.28 (m, 1H), 2.42-2.27 (m, 2H), 2.21-2.11 (m, 2H), 2.02-1.86 (m, 3H), 1.81-1.71 (m, 1H), 1.69-1.45 (m, 9H), 1.47 (s, 9H).

b) (3R)-1-(Carboxymethyl)-3-{[(1-phenylcycloheptyl)carbonyl]oxy}-1-azoniabicyclo[2.2.2]octane Bromide

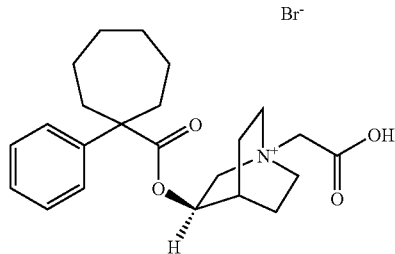

(3R)-1-(2-tert-Butoxy-2-oxoethyl)-3-{[(1-phenylcycloheptyl)carbonyl]oxy}-1-azoniabicyclo[2.2.2]octane (0.950 g) was dissolved in trifluoroacetic acid (2 mL) and left to stand for 3.5 hours. The solution was evaporated to dryness and the residual oil dissolved in acetonitrile (30 mL) and toluene (30 mL). The solution was evaporated to dryness and the procedure repeated. The resulting oil was dissolved in acetonitrile (30 mL) and diethyl ether (80 mL) added. The resulting crystals of (R)-1-(carboxymethyl)-3-(1-phenylcycloheptanecarbonyloxy)-1-azoniabicyclo[2.2.2]octane (0.600 g) were collected by filtration, washed with ether and dried.

m/e 342 [M+H—CO$_2$]$^+$ $^1$H NMR (399.826 MHz, DMSO-D$_6$) δ 7.38-7.29 (m, 4H), 7.27-7.22 (m, 1H), 5.13-5.07 (m, 1H), 4.26-4.16 (m, 2H), 4.07-3.99 (m, 1H), 3.61-3.46 (m, 4H), 3.44-3.34 (m, 1H), 2.41-2.26 (m, 2H), 2.21-2.10 (m, 2H), 2.02-1.83 (m, 3H), 1.81-1.69 (m, 1H), 1.68-1.44 (m, 9H).

EXAMPLE 35

(3R)-1-[2-(3-Chlorophenyl)ethyl]-3-{[(1-phenylcycloheptyl)carbonyl]oxy}-1-azoniabicyclo[2.2.2]octane bromide

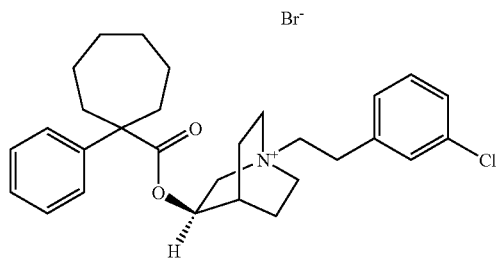

The titled compound was prepared by a procedure analogous to the method of Example 3, using (3R)-3-{[(1-phenylcycloheptyl)carbonyl]oxy}-1-azabicyclo[2.2.2]octane (Example 1) and 1-(2-bromoethyl)-3-chlorobenzene.

m/e 466 [M]$^+$ $^1$H NMR (399.826 MHz, DMSO-D$_6$) δ 7.47-7.43 (m, 1H), 7.41-7.32 (m, 5H), 7.30-7.22 (m, 3H), 5.12-5.06 (m, 1H), 3.92-3.83 (m, 1H), 3.52-3.35 (m, 5H), 3.23 (d, 1H), 3.10-2.90 (m, 3H), 2.43-2.27 (m, 3H), 2.22-2.14 (m, 2H), 2.04-1.82 (m, 3H), 1.78-1.65 (m, 1H), 1.65-1.45 (m, 8H).

EXAMPLE 36

(3R)-1-(2-Amino-2-oxoethyl)-3-{[(1-phenylcycloheptyl)carbonyl]oxy}-1-azoniabicyclo[2.2.2]octane Bromide

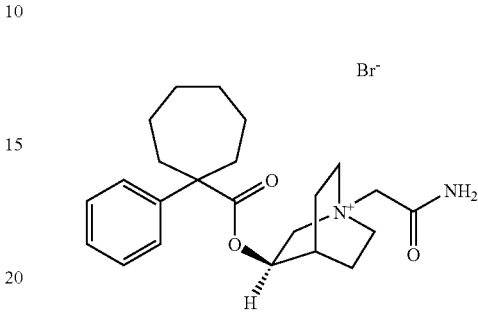

To (3R)-3-{[(1-phenylcycloheptyl)carbonyl]oxy}-1-azabicyclo[2.2.2]octane (Example 1) (0.05 g) in acetonitrile (1 mL) was added 2-bromoacetamide (0.021 g). The reaction was stirred at room temperature for 2 days and the acetonitrile was removed with a stream of nitrogen. The solid was washed with ethyl acetate and put under a high vacuum then stirred with aqueous ammonia (33%, 1 mL) for two days. The ammonia and water were removed with a stream of nitrogen and the last traces removed under high vacuum to afford the titled product (42 mg).

m/e 385 [M]$^+$ $^1$H NMR (399.826 MHz, DMSO-D$_6$) δ 7.93 (s, 1H), 7.71 (s, 1H), 7.39-7.29 (m, 4H), 7.28-7.21 (m, 1H), 5.12-5.05 (m, 1H), 4.11-3.94 (m, 1H), 4.00 (s, 2H), 3.64 (d, 1H), 3.61-3.47 (m, 2H), 3.46-3.29 (m, 1H), 2.42-2.27 (m, 2H), 2.21-2.10 (m, 2H), 2.00-1.83 (m, 3H), 1.80-1.42 (m, 1H).

EXAMPLE 37

(3R)-1-{2-Oxo-2-[(3-phenylpropyl)amino]ethyl}-3-{[(1-phenylcycloheptyl)carbonyl]oxy}-1-azoniabicyclo[2.2.2]octane Bromide

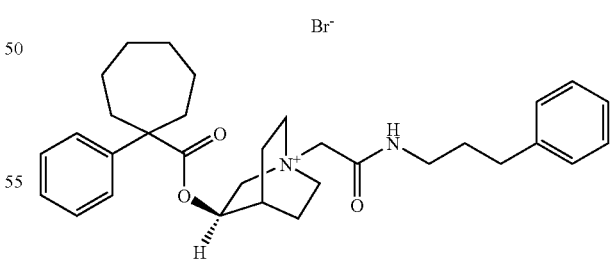

The titled compound was prepared by a procedure analogous to the method of Example 3, using (3R)-3-{[(1-phenylcycloheptyl)carbonyl]oxy}-1-azabicyclo[2.2.2]octane (Example 1) and 2-bromo-N-(3-phenylpropyl)acetamide.

m/e 503 [M]$^+$ $^1$H NMR (399.826 MHz, DMSO-D$_6$) δ 8.60 (t, 1H), 7.37-7.26 (m, 6H), 7.26-7.16 (m, 4H), 5.12-5.06 (m, 1H), 4.08-3.98 (m, 4H), 3.64-3.47 (m, 5H), 3.38-3.28 (m, 2H), 3.14 (d,

1H), 3.11 (d, 1H), 2.60 (t, 1H), 2.41-2.25 (m, 2H), 2.20-2.10 (m, 2H), 2.00-1.83 (m, 3H), 1.73 (quinitet, 2H), 1.67-1.43 (m, 8H).

EXAMPLE 38

(3R)-1-[2-(3-Chloro-4-methoxyphenyl)ethyl]-3-{[(1-phenylcycloheptyl)carbonyl]oxy}-1-azoniabicyclo[2.2.2]octane Bromide

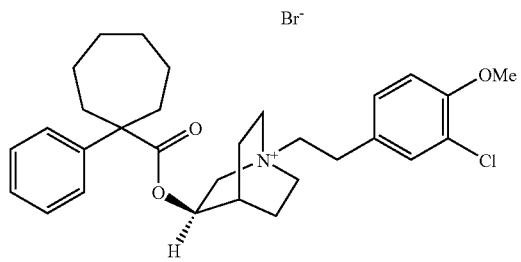

The titled compound was prepared by a procedure analogous to the method of Example 3, using (3R)-3-{[(1-phenylcycloheptyl)carbonyl]oxy}-1-azabicyclo[2.2.2]octane (Example 1) and 4-(2-bromoethyl)-2-chloro-1-methoxybenzene.

m/e 496 [M]+

$^1$H NMR (399.826 MHz, DMSO-D$_6$) δ 7.44 (d, 1H), 7.39-7.32 (m, 4H), 7.28-7.23 (m, 2H), 7.13 (d, 1H), 5.13-5.05 (m, 1H), 3.94-3.81 (m, 1H), 3.84 (s, 3H), 3.55-3.45 (m, 1H), 3.45-3.29 (m, 4H), 3.24 (d, 1H), 3.10-3.00 (m, 1H), 2.99-2.83 (m, 2H), 2.44-2.28 (m, 2H), 2.23-2.13 (m, 2H), 2.04-1.81 (m, 3H), 1.77-1.66 (m, 1H), 1.66-1.40 (m, 9H).

EXAMPLE 39

(3R)-1-{2-[(3-Methylisoxazol-5-yl)amino]-2-oxoethyl}-3-{[(1-phenylcycloheptyl)carbonyl]oxy}-1-azoniabicyclo[2.2.2]octane Bromide a) 2-Bromo-N-(3-methylisoxazol-5-yl)acetamide

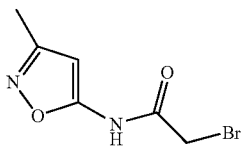

3-Methylisoxazol-5-amine (2.9 g) and potassium carbonate (9.8 g) were suspended in dichloromethane (100 mL) at room temperature 2-bromoacetyl bromide (6 g) was added dropwise. The mixture was allowed to stir overnight. Water (0.3 mL) was added together with a further quantity of potassium carbonate (3 g) and the reaction stirred for a further 30 minutes. The reaction mixture was poured into water (100 mL) and extracted with dichloromethane (2×50 mL). The combined organic extracts were dried over Magnesium Sulfate and then evaporated in vacuo. The crude product was purified by column chromatography on silica eluting with ethyl actetate/isohexane (50:50) to give sub-titled compound (4.8 g).

$^1$H NMR (299.946 MHz, CDCl$_3$) δ 11.97 (s, 1H), 6.16 (s, 1H), 4.09 (s, 2H), 2.19 (s, 3H).

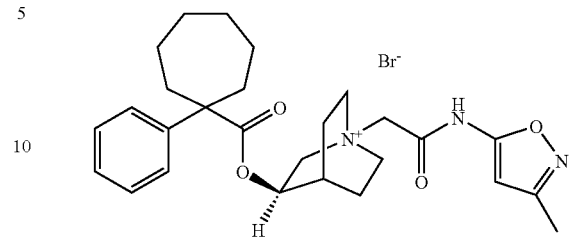

To (3R)-3-{[(1-phenylcycloheptyl)carbonyl]oxy}-1-azabicyclo[2.2.2]octane (Example 1) (0.1 g) in acetonitrile (2 mL) was added 2-bromo-N-(3-methylisoxazol-5-yl)acetamide (Example 39a) (74 mg). The reaction was stirred at room temperature overnight and the acetonitrile was removed under reduced pressure. The residue was purified by column chromatography on silica eluting with methanol/dichloromethane (10:90) to afford the titled compound (75 mg).

m/e 466 [M]+

$^1$H NMR (299.947 MHz, DMSO-D$_6$) δ 7.41-7.29 (m, 4H), 7.29-7.20 (m, 1H), 6.16 (s, 1H), 5.16-5.07 (m, 1H), 4.29 (d, 1H), 4.23 (d, 1H), 4.13-4.04 (m, 1H), 3.68-3.52 (m, 4H), 3.45-3.34 (m, 2H), 2.42-2.27 (m, 2H), 2.24-2.10 (m, 4H), 2.04-1.43 (m, 14H).

Preparation of Comparative Examples 1-9 Referred to in Table 3

COMPARATIVE EXAMPLE 1

(3R)-1-Azabicyclo[2.2.2]oct-3-yl 1-phenylcyclopentanecarboxylate

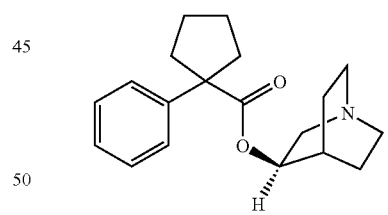

To methyl 1-phenylcyclopentanecarboxylate (1.8 g) and (R)-quinuclidin-3-ol (1.1 g) in toluene (100 mL) was added sodium hydride (100 mg, 80% in oil). The mixture was heated to reflux in a Dean and Stark apparatus for 20 hours. The reaction mixture was allowed to cool to room temperature and water (125 mL) added. The resulting organic layer was separated, dried (MgSO$_4$) and evaporated to an oil which was purified on silica eluting with ethyl acetate containing 2% triethylamine to afford titled compound as a solid (1.2 g).

m/e 300 [M+H]+

$^1$H NMR (399.826 MHz, DMSO) δ 7.29-7.39 (m, 4H), 7.20-7.27 (m, 1H), 4.55-4.62 (m, 1H), 2.98 (ddd, 1H), 2.41-2.68 (m, 4H), 2.19-2.26 (m, 1H), 1.14-1.90 (m, 13H).

COMPARATIVE EXAMPLE 2

(3R)-1-Methyl-3-{[(1-phenylcyclopentyl)carbonyl]oxy}-1-azoniabicyclo[2.2.2]octane Iodide

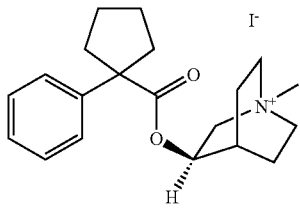

The titled compound was prepared by a procedure analogous to the method of Example 2, using (3R)-1-azabicyclo[2.2.2]oct-3-yl 1-phenylcyclopentanecarboxylate (Comparative Example 1) and iodomethane.

m/e 314 [M]$^+$ $^1$H NMR (399.826 MHz, DMSO) δ 7.31-7.42 (m, 4H), 7.23-7.30 (m, 1H), 4.95-5.01 (m, 1H), 3.80 (ddd, 1H), 3.14-3.43 (m, 5H), 2.94 (s, 3H), 2.56-2.64 (m, 2H), 2.09-2.15 (m, 1H), 1.78-2.02 (m, 4H), 1.63-1.75 (m, 5H), 1.49-1.59 (m, 1H).

COMPARATIVE EXAMPLE 3

(3R)-1-[2-Oxo-2-(pyrazin-2-ylamino)ethyl]-3-{[(1-phenylcyclopentyl)carbonyl]oxy}-1-azoniabicyclo[2.2.2]octane Bromide

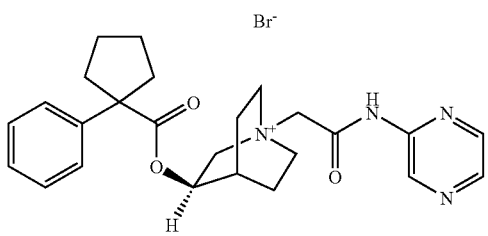

The titled compound was prepared by a procedure analogous to the method of Example 3, using (3R)-1-azabicyclo[2.2.2]oct-3-yl 1-phenylcyclopentanecarboxylate (Comparative Example 1) and 2-bromo-N-pyrazin-2-ylacetamide.

m/e 435 [M]$^+$ $^1$H NMR (399.826 MHz, DMSO) δ 11.36 (s, 1H), 9.28 (s, 1H), 8.45-8.50 (m, 2H), 7.22-7.43 (m, 5H), 5.03-5.10 (m, 1H), 4.29-4.36 (m, 2H), 4.04-4.14 (m, 1H), 3.56-3.72 (m, 4H), 3.42-3.54 (m, 1H), 2.56-2.70 (m, 2H), 2.16-2.25 (m, 1H), 1.57-2.03 (m, 10H).

COMPARATIVE EXAMPLE 4

(3R)-1-Azabicyclo[2.2.2]oct-3-yl 1-phenylcyclohexanecarboxylate

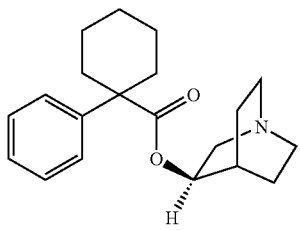

The titled compound was prepared by a procedure analogous to the method of Comparative Example 1, using methyl 1-phenylcyclohexanecarboxylate and (R)-quinuclidin-3-ol.

m/e 314 [M+H]$^+$ $^1$H NMR (399.826 MHz, DMSO) δ 7.42-7.31 (m, 4H), 7.27-7.22 (m, 1H), 4.68-4.62 (m, 1H), 3.01 (ddd, 1H), 2.68-2.35 (m, 6H), 1.82-1.16 (m, 14H).

COMPARATIVE EXAMPLE 5

(3R)-1-Methyl-3-{[(1-phenylcyclohexyl)carbonyl]oxy}-1-azoniabicyclo[2.2.2]octane Iodide

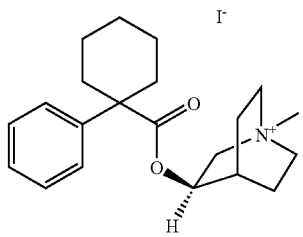

The titled compound was prepared by a procedure analogous to the method of Comparative Example 2, using (3R)-1-azabicyclo[2.2.2]oct-3-yl 1-phenylcyclohexanecarboxylate (Comparative Example 4) and iodomethane.

m/e 328 [M]$^+$ $^1$H NMR (399.826 MHz, DMSO) δ 7.33-7.44 (m, 4H), 7.24-7.30 (m, 1H), 5.00-5.07 (m, 1H), 3.82 (ddd, 1H), 3.11-3.43 (m, 5H), 2.94 (s, 3H), 2.32-2.45 (m, 2H), 2.11-2.17 (m, 1H), 1.22-1.97 (m, 12H).

COMPARATIVE EXAMPLE 6

(3R)-1-[2-Oxo-2-(pyrazin-2-ylamino)ethyl]-3-{[(1-phenylcyclohexyl)carbonyl]oxy}-1-azoniabicyclo[2.2.2]octane Bromide

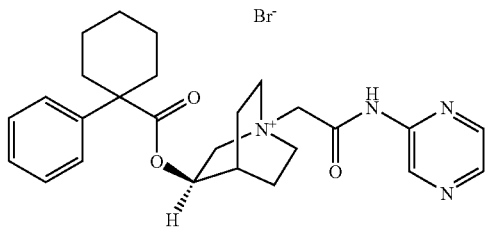

The titled compound was prepared by a procedure analogous to the method of Example 3, using (3R)-1-azabicyclo[2.2.2]oct-3-yl 1-phenylcyclohexanecarboxylate (Comparative Example 4) and 2-bromo-N-pyrazin-2-ylacetamide.

m/e 449 [M]$^+$ $^1$H NMR (399.826 MHz, DMSO) δ 11.37 (s, 1H), 9.27 (s, 1H), 8.44-8.51 (m, 2H), 7.33-7.46 (m, 4H), 7.22-7.30 (m, 1H), 5.07-5.17 (m, 1H), 4.34 (s, 2H), 4.08-4.17 (m, 1H), 3.56-3.72 (m, 4H), 3.44-3.56 (m, 1H), 2.34-2.45 (m, 2H), 2.22 (s, 1H), 1.21-2.02 (m, 12H).

COMPARATIVE EXAMPLE 7

(3R)-1-Azabicyclo[2.2.2]oct-3-yl 1-phenylcyclooctanecarboxylate a) 1-Phenylcyclooctanol

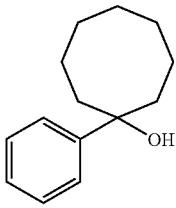

The titled compound was prepared by a procedure analogous to the method of Example 1a) using cyclooctanone (5.04 g) to afford the required compound (8.5 g).

$^1$H NMR (299.946 MHz, CDCl$_3$) δ 7.56-7.47 (m, 2H), 7.39-7.31 (m, 2H), 7.29-7.20 (m, 1H), 2.13-1.82 (m, 4H), 1.83-1.65 (m, 4H), 1.64-1.46 (m, 7H).

b) 1-Methoxy-1-phenylcyclooctane

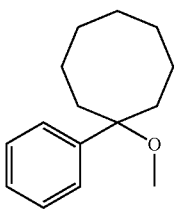

The titled compound was prepared by a procedure analogous to the method of Example 1b) using 1-phenylcyclooctanol (Comparative Example 7a) (8.5 g) to afford the required compound (12 g crude material).

$^1$H NMR (299.946 MHz, CDCl$_3$) δ 7.44-7.38 (m, 2H), 7.38-7.30 (m, 2H), 7.25-7.20 (m, 1H), 2.95 (s, 3H), 2.10 (dd, 2H), 1.96 (dd, 2H), 1.82-1.36 (m, 10H).

c) 1-Phenylcyclooctanecarboxylic Acid

The subtitled compound was prepared by the method of Example 1c using 1-methoxy-1-phenylcyclooctane (Example 2(b)) (8 g) to afford the required compound (1.6 g).

$^1$H NMR (299.946 MHz, CDCl$_3$) δ 7.40 (d, 2H), 7.32 (t, 2H), 7.23 (t, 1H), 2.38 (dd, 2H), 2.18 (dd, 2H), 1.72-1.34 (m, 10H).

d) Methyl 1-phenylcyclooctanecarboxylate

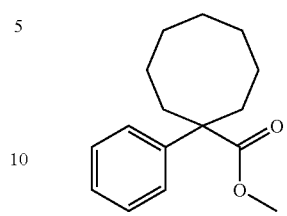

1-Phenylcyclooctanecarboxylic acid (Example 2(c)) (1.6 g) was refluxed in methanol (150 mL) and concentrated hydrochloric acid (10 mL) for 48 hours. The solvent was evaporated and the residue was dissolved in ether (100 mL) which was washed with water (100 mL), saturated sodium bicarbonate (50 mL) and water (100 mL), dried (MgSO$_4$) and evaporated to afford the sub-titled compound (1.6 g) as an oil.

$^1$H NMR (299.946 MHz, CDCl$_3$) δ 7.43-7.18 (m, 5H), 3.62 (s, 3H), 2.44-2.31 (m, 2H), 2.24-2.07 (m, 2H), 1.71-1.39 (m, 10H).

COMPARATIVE EXAMPLE 7

(3R)-1-Azabicyclo[2.2.2]oct-3-yl 1-phenylcyclooctanecarboxylate

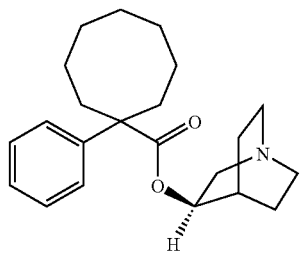

The titled compound was prepared by a procedure analogous to the method of Comparative Example 1, using methyl 1-phenylcyclooctylcarboxylate (Comparative Example 7(d)) and (R)-quinuclidin-3-ol.

m/e 342 [M+H]$^+$ $^1$H NMR (399.826 MHz, DMSO) δ 7.17-7.39 (m, 5H), 4.71-4.77 (m, 1H), 3.12 (ddd, 1H), 2.14-2.86 (m, 10H), 1.06-1.93 (m, 14H).

COMPARATIVE EXAMPLE 8

(3R)-1-Methyl-3-{[(1-phenylcyclooctyl)carbonyl]oxy}-1-azoniabicyclo[2.2.2]octane Iodide

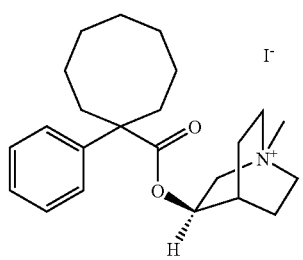

The titled compound was prepared by a procedure analogous to the method of Comparative Example 2, using (3R)-1-azabicyclo[2.2.2]oct-3-yl 1-phenylcyclooctylcarboxylate (Comparative Example 7) and iodomethane.
m/e 356 [M]+

COMPARATIVE EXAMPLE 9

(3R)-1-[2-Oxo-2-(pyrazin-2-ylamino)ethyl]-3-{[(1-phenylcyclooctyl)carbonyl]oxy}-1-azoniabicyclo[2.2.2]octane Bromide

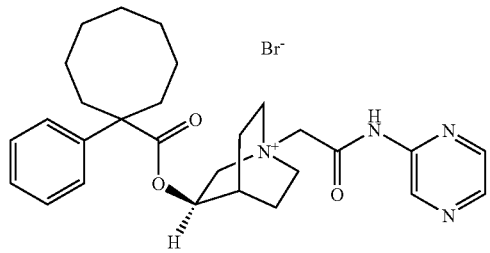

The titled compound was prepared by a procedure analogous to the method of Example 3, using (3R)-1-azabicyclo[2.2.2]oct-3-yl 1-phenylcyclooctylcarboxylate (Comparative Example 7) and 2-bromo-N-pyrazin-2-ylacetamide. m/e 477 [M]+

Pharmacological Analysis
M3 Receptor Activity Assay

The affinity ($pIC_{50}$) of compounds to the $M_3$ receptor was determined by competition binding of [$^3$H]N-methyl scopolamine (NMS) to CHO-K1 (Chinese Hamster Ovary) cell membranes expressing the human muscarinic acetylcholine $M_3$ receptor ($M_3$-ACh) in a scintillation proximity assay (SPA) format.

SPA beads were precoated with membranes and then incubated at 2 mg of beads per well with serial dilutions of the compounds of the invention, [$^3$H]NMS at 0.2 nM, half Kd (experimentally determined dissociation constant) and assay buffer (20 mM HEPES pH 7.4 containing 5 mM $MgCl_2$). The assay was conducted in a final volume of 200 μL, in the presence of 1% (v/v) dimethyl sulphoxide (DMSO). Total binding of [$^3$H]NMS was determined in the absence of competing compound and non-specific binding of [$^3$H]NMS was determined in the presence of 1 μM atropine. The plates were incubated for 16 hours at room temperature and then read on Wallac Microbeta™ using a normalised $^3$H protocol. The $pIC_{50}$, defined as the negative logarithm of the concentration of compound required for 50% reduction in specific [$^3$H]-NMS binding, was determined. Table 1 shows the $pIC_{50}$ figures for some representative Examples.

TABLE 1

| Compound of Example No. | $pIC_{50}$ |
|---|---|
| 1 | 10.2 |
| 2 | 8.5 |
| 3 | 10.3 |
| 4 | 10.2 |
| 10 | 8.5 |
| 16 | 10.1 |

Table 2 gives $IC_{50}$ strengths for the compounds of the examples.

TABLE 2

| Example No. | M3 binding $IC_{50}$ |
|---|---|
| 1 | +++ |
| 2 | ++ |
| 3 | +++ |
| 4 | +++ |
| 5 | + |
| 6 | + |
| 7 | + |
| 8 | + |
| 9 | + |
| 10 | ++ |
| 11 | +++ |
| 12 | +++ |
| 13 | +++ |
| 14 | ++ |
| 15 | ++ |
| 16 | +++ |
| 17 | +++ |
| 18 | +++ |
| 19 | +++ |
| 20 | +++ |
| 21 | +++ |
| 22 | +++ |
| 23 | +++ |
| 24 | +++ |
| 25 | +++ |
| 26 | +++ |
| 27 | +++ |
| 28 | +++ |
| 29 | ++ |
| 30 | + |
| 31 | +++ |
| 32 | ++ |
| 33 | +++ |
| 34 | + |
| 35 | +++ |
| 36 | +++ |
| 37 | ++ |
| 38 | +++ |
| 39 | +++ |

M3 Binding $IC_{50}$ < 2 nM "+++";
$IC_{50}$ 2-10 nM "++";
$IC_{50}$ > 10 nM "+";
NT—Not Tested.

One feature of the compounds of the present invention is that they comprise a cycloheptyl ring (C7 ring). As shown in Table 3, the incorporation of a cycloheptyl ring in the compounds of the present invention gives the compounds significantly higher $pIC_{50}$ $M_3$ activities than otherwise identical compounds comprising cyclopentyl (C5), cyclohexyl (C6) or cyclooctyl (C8) rings.

TABLE 3

M3 pIC50 data for representative examples according to the invention (C7) and comparative examples containing cyclopentyl (C5), cyclohexyl (C6) and cyclooctyl (C8) rings

| pIC$_{50}$ of cycloheptyl (C7) compound | pIC$_{50}$ of comparative compounds containing a cyclopentyl (C5), cyclohexyl (C6) or cyclooctyl (C8) ring in place of cycloheptyl (C7) | | |
| --- | --- | --- | --- |
| C7 | C5 | C6 | C8 |
| 10.2 (Ex. 1) | 8.7 (Comp Ex. 1) | 8.9 (Comp Ex. 4) | 9.1 (Comp Ex. 7) |
| 8.5 (Ex. 2) | 7.4 (Comp Ex. 2) | 7.3 (Comp Ex. 5) | 7.4 (Comp Ex. 8) |
| 10.1 (Ex. 16) | 9.5 (Comp Ex. 3) | 9.7 (Comp Ex. 6) | 9.5 (Comp Ex. 9) |

Measurement of Plasma Protein Binding

The extent of plasma protein binding was determined via equilibrium dialysis of a compound between human plasma and aqueous buffer at 37° C. and determination of the concentration of compound in the plasma and buffer by HPLC-MS/MS.

Method

Dialysis cells (molecular weight cut-off 5000) were prepared by rinsing with water followed by soaking in the dialysis buffer for a minimum of 1 hour. The dialysis buffer was isotonic buffered saline pH 7.4. Stock solutions of compound in dimethylsulphoxide were prepared at a concentration of 0.5 mM. Frozen pooled Human plasma was obtained from volunteers.

The stock DMSO solution of a compound was added to the plasma at a ratio of 10 µl of DMSO to each ml of plasma. This gave a 1% DMSO in plasma solution with each compound at a concentration of 5 µM.

Dialysis cells were then prepared and one half of the cell filled with 750 µl of dialysis buffer and the other half of the cell with 750 µl of plasma solution of compound. Once prepared the cells were sealed and placed in an incubator box at 37° C. These cells were then rotated for a minimum of 4 hours to equilibrate.

After equilibration 500 µl of the buffer samples were removed and added to HPLC vials along with 100 µl of plasma (sample in 6-fold diluted plasma), and 100 µl of the plasma samples were removed and added to HPLC vials along with 500 µl of dialysis buffer (sample in 6-fold diluted plasma).

The samples were then analysed using HPLC-MS/MS. A four point calibration curve was obtained by dilutions of the stock solutions with 6-fold diluted plasma at concentrations of 0.013 µM, 0.05 µM, 0.25 µM and 1.25 µM which were injected in this order followed by the buffer sample and then the plasma sample.

Calculation

The concentration of compound in the samples were determined using MassLynx version 4.1 software (produced by Waters/Micromass) that automatically calculated a calibration curve and the concentration of compound in the cells. Plasma protein binding was determined from the calibration curve as the percentage of compound bound in human plasma (% bound) using the following equation;

$$\% \text{ bound} = 100 - 100 \left( \frac{\frac{\text{buffer peak area}}{\text{buffer injection volume}}}{5 \left( \frac{\text{plasma peak area}}{\text{plasma injection volume}} \right)} \right)$$

For Example 16 the measured human plasma protein binding figure using the procedure described above was 94% bound.

Methacholine Induced Bronchoconstriction in vivo

Dunlkin-Hartley guinea-pigs (300-600 g) were supplied by a designated breeding establishment. Animals were dosed with test compound or vehicle either by inhalation in conscious guinea-pigs or by intratracheal instillation (0.5 ml/kg) under recoverable gaseous anaesthesia (5% halothane). Animals were allowed to recover from the anaesthesia prior to the measurement of bronchoconstriction. Up to 48 hours post-dosing guinea-pigs were terminally anaesthetized with sodium pentobarbitone (60 mg/kg), the trachea cannulated for artificial ventilation and the jugular vein was cannulated for intravenous administration of methacholine. The guinea-pigs were ventilated using a constant volume respiratory pump (Harvard Rodent Ventilator model 683) at a rate of 60 breath/min and a tidal volume of 5 ml/kg during surgical preparation. Lung function (lung resistance and compliance) was measured in anaesthetised and ventilated guinea-pigs using a pulmonary measurement Flexivent system (SCIREQ, Montreal, Canada) connected to the tracheal cannulae. The animals were ventilated (quasi-sinusoidal ventilation pattern) at 60 breaths/min at a tidal volume of 5 ml/kg. A positive end expiratory pressure of 2-3 cmH$_2$O was applied. Respiratory resistance was measured using the Flexivent "snapshot" facility (1 second duration, 1 Hz frequency). Lung resistance and compliance was measured before and after intravenous administration of methacholine (3, 10 and 30 ug/kg). The peak increase in resistance following methacholine challenge was calculated and the effect of the test compound on methacholine-induced lung function changes was calculated.

Percentage inhibition of bronchoconstriction was calculated at each dose of methacholine as follows:

$$\frac{\left[ \begin{array}{l} \text{Change in resistance in vehicle treated group} - \\ \text{Change in resistance in compound treated group} \end{array} \right]}{[\text{Change in resistance in vehicle treated group}]} \times 100$$

Inhibition of Pilocarpine Induced Salivation by i.n. Administered Compounds.

Guinea pigs (450-550 g) supplied by Harlan UK or David Hall, Staffs UK and acclimatised to the in-house facilities for a minimum of three days before use. Guinea pigs were randomly assigned into treatment groups and weighed. Each animal was lightly anaesthetised (4% Halothane) and administered compound or vehicle intranasally (0.5 ml/kg) at up to 24 hours before challenge with pilocarpine. At the test time point, guinea pigs were terminally anaesthetised with urethane (25% solution in H20, 1.5 g/kg). Once sufficient anaesthesia had developed (absence of toe pinch reflex) each animal had an absorbent pad placed in the mouth for 5 minutes to dry residual saliva, this pad was removed and replaced with a new pre-weighed pad for 5 minutes to establish a reading of baseline saliva production. At the end of this 5 minute period the pad was removed and weighed. A new pre-weighed pad was inserted into the mouth before each animal received s.c. pilocarpine administered under the skin at the back of the neck (0.6 mg/kg @ 2 ml/kg). The pad was removed, weighed and replaced with a new pre-weighed pad every 5 minutes up to 15 minutes.

Saliva production was calculated by subtracting the pre-weighed weight of the pad from each 5 minute period post weighed pad and these numbers added together to produce an accumulation of saliva over 15 minutes. Each 5 minute period could be analysed in addition to the whole 15 minute recording period. Baseline production of saliva was assumed to be constant and multiplied by three to produce a reading for baseline saliva production over 15 minutes.

Inhibition of saliva produced by the compound could be calculated by using the following equation: (1−(Test-baseline)/(Veh-baseline))*100.

The invention claimed is:
1. A compound of formula (I):

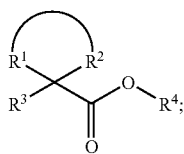

wherein $R^1$ and $R^2$, together with the carbon atom to which they are both directly attached, form a 7-membered aliphatic carbocyclic ring, wherein: the carbocyclic ring may be optionally substituted by one or more substituents independently selected from halogen, hydroxyl, $C_{1-6}$ alkoxy, $NH_2$, $NH(C_{1-6}$ alkyl), $N(C_{1-6}$ alkyl$)_2$, and $C_{1-6}$ alkyl, wherein: the $C_{1-6}$ alkyl may be optionally substituted by one or more substituents independently selected from halogen and hydroxyl;

$R^3$ is phenyl or a 5- to 6-membered heteroaryl ring, wherein: the phenyl or heteroaryl ring may be optionally substituted by one or more substituents independently selected from halogen, cyano, nitro, SH, $S(O)_{0-2}R^9$, $NR^{10}R^{11}$, $S(O)_2NR^{12}R^{13}$, $C(O)NR^{14}R^{15}$, $C(O)_2R^{16}$, $NR^{17}S(O)_2R^{18}$, $NR^{19}C(O)R^{20}$, $NR^{21}C(O)_2R^{22}$, $NR^{23}C(O)NR^{24}R^{25}$, $OR^{26}$, and $C_{1-6}$ alkyl, wherein: the $C_{1-6}$ alkyl may be optionally substituted by one or more substituents independently selected from halogen, hydroxyl, $C_{1-6}$ alkoxy, $NH_2$, $NH(C_{1-6}$ alkyl), and $N(C_{1-6}$ alkyl$)_2$;

$R^4$ is of formula (II):

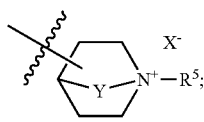

Y is —$CH_2$—, —$CH_2CH_2$—, or —$CH_2CH_2CH_2$—; when $R^4$ is of formula (II), the oxygen to which $R^4$ is directly attached is attached to either the 3- or 4-position of the ring in Formula (II);

$R^5$ is of formula (IV):

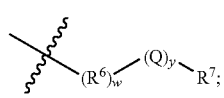

w is zero or 1;

$R^6$ is $C_{1-4}$ alkylene, wherein: the $C_{1-4}$ alkylene may be optionally substituted by one or more substituents independently selected from halogen, hydroxyl, $C_{1-6}$ alkoxy, $NH_2$, $NH(C_{1-6}$ alkyl), and $N(C_{1-6}$ alkyl$)_2$;

as to y: when w is zero, y is zero; and when w is 1, y is zero or 1;

Q is O, $S(O)_{0-2}$, $NR^8$, —$CONR^8$—, —$SO_2NR^8$—, —$NR^8CO$—, —$NR^8SO_2$—, —$OC(O)$—, —$C(O)O$—, —HC=CH—, or ethynylene;

$R^7$ is hydrogen, $Cyc^1$, or $C_{1-4}$ alkyl, wherein: the $C_{1-4}$ alkyl may be optionally substituted by one or more substituents independently selected from halogen, hydroxyl, $C_{1-4}$ alkoxy, $NH_2$, $NH(C_{1-4}$ alkyl), $N(C_{1-4}$ alkyl$)_2$, $Cyc^2$, and —$OCyc^2$; and $R^7$ may be hydrogen only when Q is O, $NR^8$, —$CONR^8$—, —$SO_2NR^8$—, —$C(O)O$—, —HC=CH—, or ethynylene;

each $Cyc^1$ and $Cyc^2$ is independently aryl, heteroaryl, a 3- to 8-membered aliphatic carbocyclic ring, or a 4- to 8-membered aliphatic heterocyclic ring, wherein: the aryl, heteroaryl, aliphatic carbocyclic ring, or aliphatic heterocyclic ring may be optionally substituted by one or more substituents independently selected from halogen, cyano, nitro, SH, $S(O)_{0-2}R^9$, $NR^{10}R^{11}$, $S(O)_2NR^{12}R^{13}$, $C(O)NR^{14}R^{15}$, $C(O)_2R^{16}$, $NR^{17}S(O)_2R^{18}$, $NR^{19}C(O)R^{20}$, $NR^{21}C(O)_2R^{22}$, $NR^{23}C(O)NR^{24}R^{25}$, $OR^{26}$, phenyl, and $C_{1-6}$ alkyl, wherein: the phenyl or $C_{1-6}$ alkyl may be optionally substituted by one or more substituents independently selected from halogen, hydroxyl, $C_{1-6}$ alkoxy, $NH_2$, $NH(C_{1-6}$ alkyl), and $N(C_{1-6}$ alkyl$)_2$;

$R^8$ is hydrogen or $C_{1-6}$ alkyl;

each $R^9$ and $R^{18}$ is independently $C_{1-6}$ alkyl, wherein: the $C_{1-6}$ alkyl may be optionally substituted by one or more substituents independently selected from halogen, hydroxyl, $C_{1-6}$ alkoxy, $NH_2$, $NH(C_{1-6}$ alkyl), and $N(C_{1-6}$ alkyl$)_2$;

each $R^{10}$, $R^{11}$, $R^{12}$, $R^{13}$, $R^{14}$, $R^{15}$, $R^{16}$, $R^{17}$, $R^{19}$, $R^{20}$, $R^{21}$, $R^{22}$, $R^{23}$, $R^{24}$, $R^{25}$, and $R^{26}$ is independently hydrogen or $C_{1-6}$ alkyl, wherein: the $C_{1-6}$ alkyl may be optionally substituted by one or more substituents independently selected from halogen, hydroxyl, $C_{1-6}$ alkoxy, $NH_2$, $NH(C_{1-6}$ alkyl), and $N(C_{1-6}$ alkyl$)_2$; or any of $R^{10}$ and $R^{11}$, $R^{12}$ and $R^{13}$, $R^{14}$ and $R^{15}$, or $R^{24}$ and $R^{25}$, together with the nitrogen atom to which they are both attached, may alternatively form a 4- to 8-membered aliphatic heterocyclic ring, wherein: the heterocyclic ring may be optionally substituted by one or more substituents independently selected from halogen, hydroxyl, and $C_{1-6}$ alkyl, wherein: the $C_{1-6}$ alkyl may be optionally substituted by one or more substituents independently selected from halogen and hydroxyl; and $X^-$ is a pharmaceutically acceptable anion of a mono or polyvalent acid.

2. A compound according to claim 1, wherein $R^3$ is phenyl, wherein: the phenyl may be optionally substituted by one or more substituents independently selected from halogen, hydroxyl, $C_{1-4}$ alkoxy, $NH_2$, $NH(C_{1-4}$ alkyl), $N(C_{1-4}$ alkyl$)_2$, OCF₃, and C₁₋₄ alkyl, wherein: the C₁₋₄ alkyl may be optionally substituted by one or more substituents independently selected from halogen and hydroxyl.

3. A compound according to claim 1, wherein R¹ and R², together with the carbon atom to which they are both directly attached, form a 7-membered cycloalkyl ring, wherein: the cycloalkyl ring may be optionally substituted by one or more substituents independently selected from halogen, hydroxyl, and C₁₋₄ alkyl.

4. A compound according to claim 1, wherein: R¹ and R², together with the carbon atom to which they are both directly attached, form a 7-membered cycloalkyl ring; and R³ is phenyl.

5. A compound according to claim 1, wherein R⁴ is of formula (IIa):

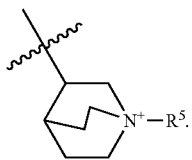

(IIa)

6. A compound according to claim 1, wherein R⁵ is C₁₋₄ alkyl, wherein: the C₁₋₄ alkyl may be optionally substituted by one or more substituents independently selected from halogen, hydroxyl, C₁₋₄ alkoxy, phenyl, naphthyl, furanyl, thienyl, and phenoxy, wherein: the phenyl, naphthyl, furanyl, thienyl, or phenoxy may be optionally substituted by one or more substituents independently selected from halogen, hydroxyl, cyano, C₁₋₄ alkoxy, NH₂, NH(C₁₋₄ alkyl), N(C₁₋₄ alkyl)₂, OCF₃, and C₁₋₄ alkyl, wherein: the C₁₋₄ alkyl may be optionally substituted by one or more substituents independently selected from halogen and hydroxyl.

7. A compound according to claim 1, wherein:
R⁵ is —C₁₋₄ alkylene-Q-R⁷;
Q is O, —CONH—, or —C(O)O—;
R⁷ is hydrogen, Cyc¹, or C₁₋₄ alkyl, wherein: the C₁₋₄ alkyl may be optionally substituted by one or more substituents independently selected from halogen, hydroxyl, phenyl, and phenoxy, wherein: the phenyl and phenoxy may be optionally substituted by one or more substituents independently selected from halogen, hydroxyl, cyano, C₁₋₄ alkoxy and OCF₃; and
Cyc¹ is phenyl, a 5- to 6-membered heteroaryl ring, or a 4- to 8-membered aliphatic heterocyclic ring, wherein: the phenyl, heteroaryl, or aliphatic heterocyclic ring may be optionally substituted with one or more substituents independently selected from halogen, hydroxyl, C₁₋₄ alkoxy, NH₂, NH(C₁₋₄ alkyl), N(C₁₋₄ alkyl)₂, phenyl, and C₁₋₄ alkyl, wherein: the phenyl and C₁₋₄ alkyl may be optionally substituted by one or more substituents independently selected from halogen and hydroxyl.

8. A compound according to claim 1, wherein:
R⁵ is —C₁₋₄ alkylene-Q-Cyc¹;
Q is —CONH—; and
Cyc¹ is a 5- to 6-membered heteroaryl, wherein: the heteroaryl may be optionally substituted with one or more substituents independently selected from halogen, hydroxyl, C₁₋₄ alkoxy, NH₂, NH(C₁₋₄ alkyl), N(C₁₋₄ alkyl)₂, phenyl, and C₁₋₄ alkyl, wherein: the phenyl and C₁₋₄ alkyl may be optionally substituted by one or more substituents independently selected from halogen and hydroxyl.

9. A compound, wherein: the compound is selected from the group consisting of:
(3R)-1-Methyl-3-{[(1-phenylcycloheptyl)carbonyl]oxy}-1-azoniabicyclo[2.2.2]octane X,
(3R)-1-(3-Phenoxypropyl)-3-{[(1-phenylcycloheptyl)carbonyl]oxy}-1-azoniabicyclo[2.2.2]octane X,
(3R)-1-[2-(Isoxazol-3-ylamino)-2-oxoethyl]-3-{[(1-phenylcycloheptyl)carbonyl]oxy}-1-azoniabicyclo[2.2.2]octane X,
(3R)-1-(4-Fluorobenzyl)-3-{[(1-phenylcycloheptyl)carbonyl]oxy}-1-azoniabicyclo[2.2.2]octane X,
(3R)-1-Benzyl-3-{[(1-phenylcycloheptyl)carbonyl]oxy}-1-azoniabicyclo[2.2.2]octane X,
(3R)-3-{[(1-Phenylcycloheptyl)carbonyl]oxy}-1-[3-(trifluoromethoxy)benzyl]-1-azoniabicyclo[2.2.2]octane X,
(3R)-1-(3,4-Difluorobenzyl)-3-{[(1-phenylcycloheptyl)carbonyl]oxy}-1-azoniabicyclo[2.2.2]octane X,
(3R)-3-{[(1-Phenylcycloheptyl)carbonyl]oxy}-1-{[5-(trifluoromethyl)-2-furyl]methyl}-1-azoniabicyclo[2.2.2]octane X,
(3R)-1-(3-Methoxybenzyl)-3-{[(1-phenylcycloheptyl)carbonyl]oxy}-1-azoniabicyclo[2.2.2]octane X,
(3R)-1-(2-Phenoxyethyl)-3-{[(1-phenylcycloheptyl)carbonyl]oxy}-1-azoniabicyclo[2.2.2]octane X,
(3R)-1-[2-(Benzyloxy)ethyl]-3-{[(1-phenylcycloheptyl)carbonyl]oxy}-1-azoniabicyclo[2.2.2]octane X,
(3R)-1-[2-(Isoxazol-3-ylamino)-2-oxoethyl]-3-({[1-(2-thienyl)cycloheptyl]carbonyl}oxy)-1-azoniabicyclo[2.2.2]octane X,
(3R)-1-(2-oxo-2-pyrrolidin-1-ylethyl)-3-{[(1-phenylcycloheptyl)carbonyl]oxy}-1-azoniabicyclo[2.2.2]octane X,
(3R)-1-(2-Morpholin-4-yl-2-oxoethyl)-3-{[(1-phenylcycloheptyl)carbonyl]oxy}-1-azoniabicyclo[2.2.2]octane X,
(3R)-1-[2-oxo-2-(pyrazin-2-ylamino)ethyl]-3-{[(1-phenylcycloheptyl)carbonyl]oxy}-1-azoniabicyclo[2.2.2]octane X,
(3R)-1-[2-oxo-2-(pyridazin-3-ylamino)ethyl]-3-{[(1-phenylcycloheptyl)carbonyl]oxy}-1-azoniabicyclo[2.2.2]octane X,
(3R)-1-{2-oxo-2-[(2-phenoxyethyl)amino]ethyl}-3-{[(1-phenylcycloheptyl)carbonyl]oxy}-1-azoniabicyclo[2.2.2]octane X,
(3R)-1-[2-(3-Fluorophenyl)-2-oxoethyl]-3-{[(1-phenylcycloheptyl)carbonyl]oxy}-1-azoniabicyclo[2.2.2]octane X,
(3R)-1-{2-[(5-Methylisoxazol-3-yl)amino]-2-oxoethyl}-3-{[(1-phenylcycloheptyl)carbonyl]oxy}-1-azoniabicyclo[2.2.2]octane X,
(3R)-1-{2-[(6-Chloropyridazin-3-yl)amino]-2-oxoethyl}-3-{[(1-phenylcycloheptyl)carbonyl]oxy}-1-azoniabicyclo[2.2.2]octane X,
(3R)-1-{2-[(3-Fluorophenyl)amino]-2-oxoethyl}-3-{[(1-phenylcycloheptyl)carbonyl]oxy}-1-azoniabicyclo[2.2.2]octane X,
(3R)-1-[2-(2-Naphthyl)ethyl]-3-{[(1-phenylcycloheptyl)carbonyl]oxy}-1-azoniabicyclo[2.2.2]octane X,
(3R)-1-[2-(3-Methoxyphenyl)ethyl]-3-{[(1-phenylcycloheptyl)carbonyl]oxy}-1-azoniabicyclo[2.2.2]octane X,
(3R)-1-[2-(5-Methyl-2-thienyl)ethyl]-3-{[(1-phenylcycloheptyl)carbonyl]oxy}-1-azoniabicyclo[2.2.2]octane X,
(3R)-3-{[(1-Phenylcycloheptyl)carbonyl]oxy}-1-(2-phenylethyl)-1-azoniabicyclo[2.2.2]octane X, (3R)-3-{[(1-Phenylcycloheptyl)carbonyl]oxy}-1-{2-[3-(trifluoromethyl)phenyl]ethyl}-1-azoniabicyclo[2.2.2]octane X,
(3R)-1-[2-(1,3-Benzodioxol-5-yl)ethyl]-3-{[(1-phenylcycloheptyl)carbonyl]oxy}-1-azoniabicyclo[2.2.2]octane X,
(3R)-1-[2-(4-Cyanophenyl)ethyl]-3-{[(1-phenylcycloheptyl)carbonyl]oxy}-1-azoniabicyclo[2.2.2]octane X,
(3R)-1-[2-(1,3-Dioxo-1,3-dihydro-2H-isoindol-2-yl)ethyl]-3-{[(1-phenylcycloheptyl)carbonyl]oxy}-1-azoniabicyclo[2.2.2]octane X,
(3R)-1-{2-[(6-Chloropyrazin-2-yl)amino]-2-oxoethyl}-3-{[(1-phenylcycloheptyl)carbonyl]oxy}-1-azoniabicyclo[2.2.2]octane X,
(3R)-1-{[1-(4-Chlorophenyl)cyclopropyl]methyl}-3-{[(1-phenylcycloheptyl)carbonyl]oxy}-1-azoniabicyclo[2.2.2]octane X,
(3R)-1-{2-[(5-Methylpyrazin-2-yl)amino]-2-oxoethyl}-3-{[(1-phenylcycloheptyl)carbonyl]oxy}-1-azoniabicyclo[2.2.2]octane X,
(3R)-1-(Carboxymethyl)-3-{[(1-phenylcycloheptyl)carbonyl]oxy}-1-azoniabicyclo[2.2.2]octane X,
(3R)-1-[2-(3-Chlorophenyl)ethyl]-3-{[(1-phenylcycloheptyl)carbonyl]oxy}-1-azoniabicyclo[2.2.2]octane X,
(3R)-1-(2-Amino-2-oxoethyl)-3-{[(1-phenylcycloheptyl)carbonyl]oxy}-1-azoniabicyclo[2.2.2]octane X,
(3R)-1-{2-oxo-2-[(3-phenylpropyl)amino]ethyl}-3-{[(1-phenylcycloheptyl)carbonyl]oxy}-1-azoniabicyclo[2.2.2]octane X,
(3R)-1-[2-(3-Chloro-4-methoxyphenyl)ethyl]-3-{[(1-phenylcycloheptyl)carbonyl]oxy}-1-azoniabicyclo[2.2.2]octane X; and
(3R)-1-{2-[(3-Methylisoxazol-5-yl)amino]-2-oxoethyl}-3-{[(1-phenylcycloheptyl)carbonyl]oxy}-1-azoniabicyclo[2.2.2]octane X; and X is a pharmaceutically acceptable anion of a mono or polyvalent acid.

10. A pharmaceutical composition, wherein the composition comprises: a compound of claim 1; and a pharmaceutically acceptable adjuvant, diluent, or carrier.

11. A process for the preparation of a pharmaceutical composition, wherein the process comprises mixing a compound of claim 1 with a pharmaceutically acceptable adjuvant, diluent, or carrier.

12. A pharmaceutical product comprising: a first active ingredient which is a compound of claim 1, and at least one further active ingredient selected from: a phosphodiesterase inhibitor, a β2 adrenoceptor agonist, a modulator of chemokine receptor function, an inhibitor of kinase function, a protease inhibitor, a steroidal glucocorticoid receptor agonist, and a non-steroidal glucocorticoid receptor agonist.

13. A compound of formula (V), or a pharmaceutically acceptable acid addition salt thereof, wherein:

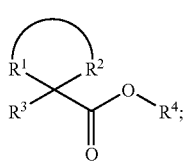

(V)

$R^1$ and $R^2$, together with the carbon atom to which they are both directly attached, form a 7-membered aliphatic carbocyclic ring, wherein: the carbocyclic ring may be optionally substituted by one or more substituents independently selected from halogen, hydroxyl, $C_{1-6}$ alkoxy, $NH_2$, $NH(C_{1-6}$ alkyl), $N(C_{1-6}$ alkyl)$_2$, and $C_{1-6}$ alkyl, wherein: the $C_{1-6}$ alkyl may be optionally substituted by one or more substituents independently selected from halogen and hydroxyl;

$R^3$ is phenyl or a 5- to 6-membered heteroaryl ring, wherein: the phenyl or heteroaryl ring may be optionally substituted by one or more substituents independently selected from halogen, cyano, nitro, SH, $S(O)_{0-2}R^9$, $NR^{10}R^{11}$, $S(O)_2NR^{12}R^{13}$, $C(O)NR^{14}R^{15}$, $C(O)_2R^{16}$, $NR^{17}S(O)_2R^{18}$, $NR^{19}C(O)R^{20}$, $NR^{21}C(O)_2R^{22}$, $NR^{23}C(O)NR^{24}R^{25}$, $OR^{26}$, and $C_{1-6}$ alkyl, wherein: the $C_{1-6}$ alkyl may be optionally substituted by one or more substituents independently selected from halogen, hydroxyl, $C_{1-6}$ alkoxy, $NH_2$, $NH(C_{1-6}$ alkyl), and $N(C_{1-6}$ alkyl)$_2$;

$R^4$ is of formula (VI):

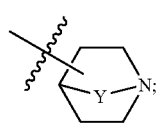

(VI)

Y is —$CH_2$—, —$CH_2CH_2$—, or —$CH_2CH_2CH_2$—; when $R^4$ is of formula (VI), the oxygen to which $R^4$ is directly attached is attached to either the 3- or 4-position of the ring in Formula (VI);

each $R^9$ and $R^{18}$ is independently $C_{1-6}$ alkyl, wherein: the $C_{1-6}$ alkyl may be optionally substituted by one or more substituents independently selected from halogen, hydroxyl, $C_{1-6}$ alkoxy, $NH_2$, $NH(C_{1-6}$ alkyl), and $N(C_{1-6}$ alkyl)$_2$; and each $R^{10}$, $R^{11}$, $R^{12}$, $R^{13}$, $R^{14}$, $R^{15}$, $R^{16}$, $R^{17}$, $R^{19}$, $R^{20}$, $R^{21}$, $R^{22}$, $R^{23}$, $R^{24}$, $R^{25}$, and $R^{26}$ is independently hydrogen or $C_{1-6}$ alkyl, wherein: the $C_{1-6}$ alkyl may be optionally substituted by one or more substituents independently selected from halogen, hydroxyl, $C_{1-6}$ alkoxy, $NH_2$, $NH(C_{1-6}$ alkyl), and $N(C_{1-6}$ alkyl)$_2$; or any of $R^{10}$ and $R^{11}$, $R^{12}$ and $R^{13}$, $R^{14}$ and $R^{15}$, or $R^{24}$ and $R^{25}$, together with the nitrogen atom to which they are both attached, may alternatively form a 4- to 8-membered aliphatic heterocyclic ring, wherein: the heterocyclic ring may be optionally substituted by one or more substituents independently selected from halogen, hydroxyl, and $C_{1-6}$ alkyl, wherein: the $C_{1-6}$ alkyl may be optionally substituted by one or more substituents independently selected from halogen and hydroxyl.

14. A compound of claim 8, wherein $R^5$ is —$CH_2$-Q-$Cyc^1$.

15. A compound of claim 14, wherein $Cyc^1$ is a 5- to 6-membered heteroaryl optionally substituted by $C_{1-4}$ alkyl.

* * * * *